United States Patent
Chaiken

(10) Patent No.: US 8,538,499 B2
(45) Date of Patent: Sep. 17, 2013

(54) PROCESS AND APPARATUS FOR NON-INVASIVE, CONTINUOUS IN VIVO MEASUREMENT OF HEMATOCRIT

(75) Inventor: Joseph Chaiken, Fayetteville, NY (US)

(73) Assignee: LighTouch Medical, Inc., Bryn Athyn, PA (US)

(*) Notice: Subject to any disclaimer, the term of this patent is extended or adjusted under 35 U.S.C. 154(b) by 304 days.

(21) Appl. No.: 12/889,396

(22) Filed: Sep. 23, 2010

(65) Prior Publication Data

US 2011/0077496 A1 Mar. 31, 2011

Related U.S. Application Data

(60) Provisional application No. 61/245,020, filed on Sep. 23, 2009.

(51) Int. Cl.
*A61B 5/00* (2006.01)

(52) U.S. Cl.
USPC .......................................... 600/322

(58) Field of Classification Search
USPC .......................... 600/476, 316–322
See application file for complete search history.

(56) References Cited

U.S. PATENT DOCUMENTS

| | | | |
|---|---|---|---|
| 6,044,285 A | 3/2000 | Chaiken et al. | |
| 6,223,063 B1 | 4/2001 | Chaiken et al. | |
| 6,289,230 B1 * | 9/2001 | Chaiken et al. | 600/322 |
| 6,292,686 B1 | 9/2001 | Chaiken et al. | |
| 6,352,502 B1 | 3/2002 | Chaiken et al. | |
| 6,377,828 B1 | 4/2002 | Chaiken et al. | |
| 6,389,306 B1 | 5/2002 | Chaiken et al. | |
| 6,503,478 B2 | 1/2003 | Chaiken et al. | |
| 6,524,858 B1 * | 2/2003 | Zelmanovic et al. | 436/10 |
| 6,681,133 B2 | 1/2004 | Chaiken et al. | |
| 7,050,842 B2 | 5/2006 | Chaiken et al. | |
| 7,664,605 B2 | 2/2010 | Chaiken et al. | |
| 2007/0177143 A1 | 8/2007 | Chaiken et al. | |
| 2008/0306363 A1 | 12/2008 | Chaiken et al. | |

OTHER PUBLICATIONS

Barman, I. et al., "Turbidity-Corrected Raman Spectroscopy for Blood Analyte Detection", *Anal. Chem*, 2009, 81(11):4233-4240.

Chaiken, J. et al., "Simultaneous, noninvasive observation of elastic scattering . . . ", *J. of Biomedical Optics*, Sep. /Oct. 2009, 14(5):050505-1-3.

Chaiken, J. et al., "On probing human fingertips in vivo using near-infrared . . . " *J. of Biomedical Optics*, May/Jun. 2010, 15(3):037007-1-15.

Deng, Bin et al., "Direct noninvasive observation of near infrared photobleaching . . . " *Proc. of SPIE*, 7560: 75600P-1-11.

Lipson, J. et al., "Requirements for Calibration in Noninvasive Glucose Monitoring by Raman Spectroscopy", *J. of Diabetes Science and Technology*, 2009, 3(2):233-241.

\* cited by examiner

*Primary Examiner* — Tse Chen
*Assistant Examiner* — Hien Nguyen
(74) *Attorney, Agent, or Firm* — Karen S. Canady; canady + lortz LLP

(57) ABSTRACT

The invention provides a method and apparatus obtaining a hematocrit from a sample of in vivo tissue. The method comprises irradiating the sample with a single incident wavelength on a sample of tissue, simultaneously measuring wavelength shifted (IE) and unshifted (EE) light emitted from the tissue, and determining a relative volume of light emitted from two phases, wherein the two phases comprise a first Rayleigh and Mie scattering and fluorescent phase associated with red blood cells, and a second, non-scattering phase associated with plasma. The hematocrit is calculated from the volume of light emitted by the first phase relative to the total volume of light emitted from the first and second phases.

27 Claims, 20 Drawing Sheets

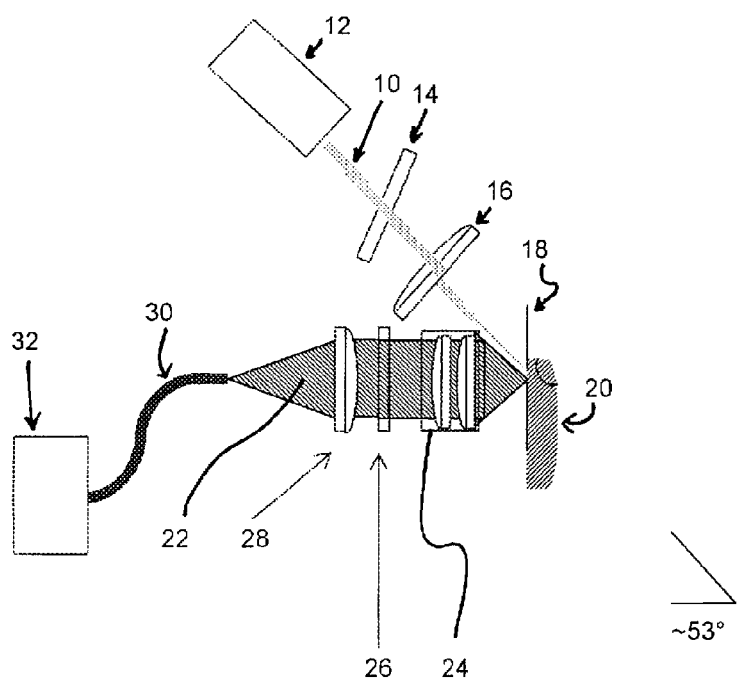
Figure 23
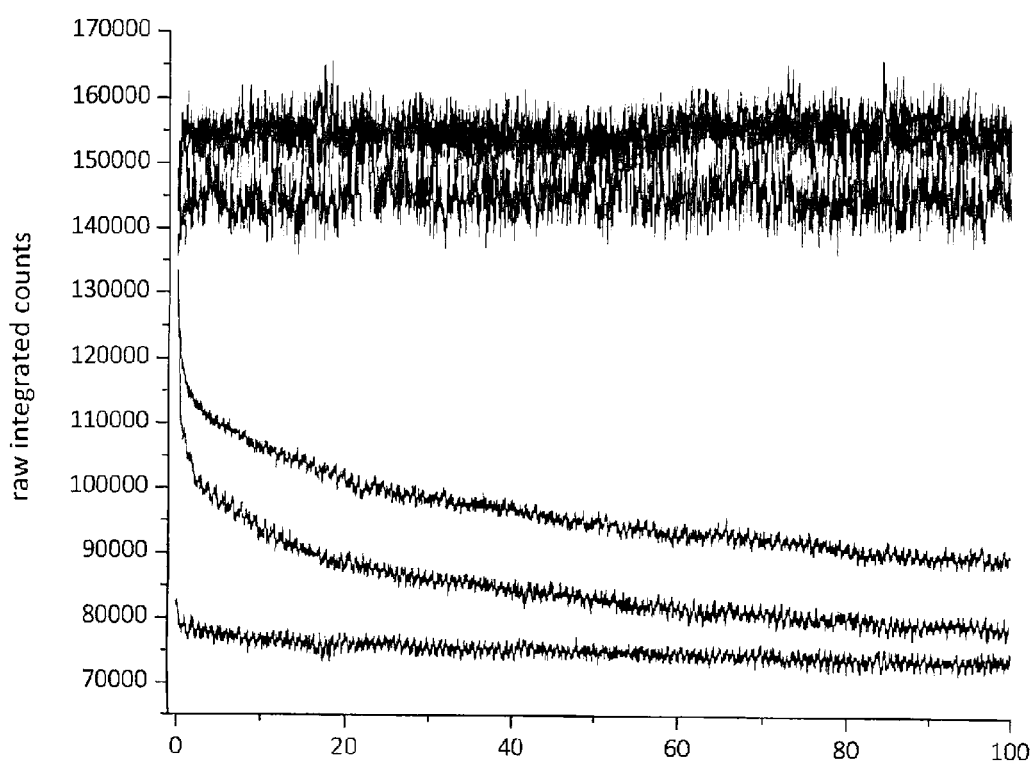
Figure 24 time (sec)

PROCESS AND APPARATUS FOR NON-INVASIVE, CONTINUOUS IN VIVO MEASUREMENT OF HEMATOCRIT

This application claims benefit of U.S. provisional patent application No. 61/245,020, filed on Sep. 23, 2009, the entire contents of which are incorporated herein by reference. Throughout this application various publications are referenced. The disclosures of these publications in their entireties are hereby incorporated by reference into this application in order to more fully describe the state of the art to which this invention pertains.

BACKGROUND OF THE INVENTION

The leading cause of death for people aged 18-45, civilian and military, is hemorrhagic shock following traumatic blood loss. Early detection of hemorrhage is essential to give medical staff an opportunity to intervene. When there are no external signs of trauma, however, autonomic compensatory changes cause internal bleeding to be very difficult to detect. Undetected internal blood loss can be manifest by compartment scale fluid shifts, surface fluid redistribution and a change in blood composition as the body compensates for net blood volume loss. The absolute blood hematocrit changes but other physiological measures also change and, depending on the measurement site and primary hemorrhage site, some change earlier. The earliest indicators of hemorrhage are well known but there are no means to obtain a continuous real-time record in order to log temporal changes and reactions to external probing/examination. There remains an urgent need for a process to allow determination of hematocrit noninvasively and in vivo. This invention teaches a noninvasive method and apparatus for obtaining a continuous time record of relative blood hematocrit, particularly in humans.

SUMMARY OF THE INVENTION

The invention provides a method of obtaining a hematocrit from a sample of in vivo tissue. The method comprises irradiating the sample with a single incident wavelength on a sample of tissue, and simultaneously measuring wavelength shifted (IE) and unshifted (EE) light emitted from the tissue. The method further comprises determining a relative volume of light emitted from two phases, wherein the two phases comprise a first Rayleigh and Mie scattering and fluorescent phase associated with red blood cells, and a second, non-scattering phase associated with plasma. The hematocrit is calculated from the volume of light emitted by the first phase relative to the total volume of light emitted from the first and second phases.

In a typical embodiment, the incident wavelength is 580-2500 nm. In some embodiments, the incident wavelength is 785, 805 or 830 nm. The measuring is typically at 500-1800 cm$^{-1}$ for shifted light, and at $-30-+10$ cm$^{-1}$ for unshifted light.

In one embodiment, the determining comprises calculating the hematocrit as:

$$\phi_r / (\phi_r + \phi_p) \tag{5}$$

$$\text{wherein } \phi_r = a + \left(b \frac{EE}{EE_0}\right) + \left(c \frac{IE}{IE_0}\right) \tag{8}$$

$$\phi_p = d + \left(e \frac{EE}{EE_0}\right) + \left(f \frac{IE}{IE_0}\right) \tag{9}$$

$$EE = \aleph_1 + \aleph_2 \phi_p + \aleph_3 \phi_r \tag{6}$$

$$IE = \aleph_4 + \aleph_5 \phi_p + \aleph_6 \phi_r \tag{7}$$

and wherein EE is total elastically (unshifted) emitted light, IE is total inelastically (shifted) emitted light, $\aleph_1$ and $\aleph_4$ are the fractions of EE and IE, respectively, from static tissue; $\aleph_2$ and $\aleph_5$ are the fractions of EE and IE, respectively, from plasma; $\aleph_3$ and $\aleph_6$ are the fractions of EE and IE, respectively, from red blood cells (rbcs); and $\aleph_{1-6}$ are calculated numerically using the radiative transport equation (RTE) using optical and geometric parameters appropriate to the tissue and instrumentation appropriate to the specific probing, to determine EE and IE as a function of $\phi_r$ and $\phi_p$; wherein $EE_0$ and $IE_0$ are calculated or measured average values of EE and IE over a calibration time period that depends on the laser power and volume of tissue probed under a reference condition. Values for a-f can be obtained by inverting equations [6] and [7] to express $\phi_r$ and $\phi_p$ in terms of EE and IE.

Where values for $\aleph_{1-6}$ are not available, $EE/EE_0$ and $IE/IE_0$ can be obtained by quantitative estimation using, for example, ventricular ejection volume averaged over entire circulation volume. In another example, the values are estimated using the modulated spectra obtained during a blood depleted state in the tissue and spectra obtained in a blood replete state. For example, values for a-f can be obtained from estimated values for $\phi_r$ and $\phi_p$ derived from a calibration condition during which $EE=EE_0$ and $IE=IE_0$ and/or another calibration condition in which IE and EE can be associated with the cardiac pulse. This can be a moving average in some situations, e.g. when analyzing the AC components of the EE and IE. In a typical embodiment, the tissue is fingertip, and a+b+c=0.004 and d+e+f=0.036. This follows from evaluating [8] and [9] under conditions in which e.g. for skin, $\phi_r$=0.004 and $\phi_p$=0.036

Another example of determining parameters from empirical comparisons is the ventricular ejection volume example, wherein with each cardiac pulse ≈75 ml of homeostatic hematocrit blood is ejected into the ≈4000 ml total supply. This ≈1.9% transient increase in blood volume, i.e. for both $\phi_r$ and $\phi_p$, constitutes the pressure wave of the pulse, and corresponds a 2.626% and −2.08% change in EE and IE, respectively, with each cardiac driven pulse, i.e. systoli EE and IE minus diastoli EE and IE. These two conditions can be inserted into [8] and [9] to generate two constraints on the values of the parameters a-f. For example, one can assume that with each pulse the $\phi_r$ and $\phi_p$ increase by 0.00008 and 0.00072 respectively. One can combine this with the observed fractional changes in IE and EE to write:

b=(0.00008−0.02626)c/(−0.0208) and e=(0.00072−0.02626)f/(−0.0208)

These estimations can be used in embodiments in which the tissue is a fingertip and other tissues involving similar parameters.

As another example, a test subject fingertip was tissue modulated between 83 g-force/cm$^2$ and 276 g-force/cm$^2$, and the IE increased by 3.03% and the EE decreased by 9.6%. These corresponded to an estimated decrease of the $\phi_r$ to 0.00024 and the $\phi_p$ to 0.00376, both based on the 3 and 4 times the amount of red blood cells and plasma moved by a single pulse. Under such externally applied pressure more plasma is expected to move than red blood cells, due to the well known microcirculation phenomena of plasma skimming, Fahraeus and Fahraeus-Lindquist effects. Putting these values into [8] and [9] above, gives for the $\phi_r$ equation:

$$0.00376 = a + 1.0303b + 0.90407c.$$

This can be combined with the corresponding equation for $\phi_r$, $0.004 = a + b + c$ to eliminate the parameter a to then solve for b in terms of c:

$$b = -0.00792 - 3.657c.$$

A similar equation can be obtained from the IE variation and the estimated values for $\phi_p$ to produce 2 more constraints. Note that in this case the final hematocrit was 0.0769.

$$e = -0.09504 - 3.657f.$$

Using any guess for the 6 parameters in [8] and [9], e.g. from the RTE equation approach described above, IE and EE can be calculated using [6] and [7] and this can be inverted numerically to produce the two equations of the form of [8] and [9] and simultaneously the parameters a through f needed to calculate the and $\phi_r$ and $\phi_p$. Many available spread sheet programs, e.g. the Solver in Microsoft Excel™, can be used to do this calculation and then vary any two parameters, e.g. c and f, subject to the four constraints just given, so as to minimize the standard deviation of the hematocrit over a time series.

The exact choice of c and f needed to initialize the nonlinear least squares routine is not particularly important so, as a practical matter, they can be chosen initially to be equal to any of the other parameters. Regardless of the exact choice, the least squares routine converges to the same quantitative result for c and f. Furthermore, the Hct value consistent with the initial choice of $\phi_r$ and $\phi_p$ is maintained until or unless the EE and IE start to deviate from the reference values.

A full set of optimized parameters so obtained can be used later for the same person or different people to monitor any changes of the hematocrit in time.

The tissue modulation process can be used to produce different and reproducible phase fractions for purposes of generating unusual distributions of the phases and the corresponding EE and IE data to input into the calibration process just described.

In particular, pressing harder than the systolic pressure for several seconds is effective. For example, one can use a particular applied pressure relative to the test subject's diastolic and systolic blood pressures, or perhaps a particular temporal position with respect to the cardiac pulse. Any choice should be based on measurement conditions that actually produce the assumed set of volume fractions defining the model calculation.

In a typical embodiment, the tissue is human. Other species, particularly primates and other vertebrates, can also be subjects for whom the method is useful. Typically, the tissue is a fingertip, although those skilled in the art will appreciate the applicability of the method to other areas of the body, including forearm and ear lobe, for example. In one embodiment, the fingertip is pressed against an aperture of an apparatus that emits light directed at the fingertip through the aperture. In a typical embodiment, the pressure at which the fingertip is initially pressed is approximately the average of the prevailing systolic and diastolic blood pressures of the subject.

The EE and IE can be the AC components of the time dependent EE and IE signals, for example, in the bandpass of 2.5 Hz to 0.25 Hz. The method EE and IE can alternatively be the DC components of the time dependent EE and IE signals, e.g., in the bandpass of $0\pm10$ Hz.

The invention additionally provides an apparatus for obtaining a hematocrit from a sample of tissue. The apparatus comprises a means for irradiating the sample with a single incident wavelength on a sample of tissue; a means for simultaneously measuring wavelength shifted and unshifted light emitted from the tissue; and means for determining a relative volume of light emitted from two phases, wherein the two phases comprise a first predominantly Rayleigh and Mie scattering and fluorescent phase associated with red blood cells, and a second, non-scattering phase associated with plasma. Typically, the apparatus also includes means for calculating a volume fraction of red blood cells relative to the total volume of red blood cells and plasma.

BRIEF DESCRIPTION OF THE FIGURES

FIGS. 1A and 1B both show same data, but at different temporal resolution.

The sections used to calculate inelastic scattering intensity IE ($\approx 500\text{–}1750$ cm$^{-1}$) and elastic scattering intensity EE ($-30\text{–}+10$ cm$^{-1}$) are shown. The low shift integration limit for obtaining IE was chosen by reference to the output obtained when the sample is a non-fluorescent metal and requiring that no EE is included in the IR integral.

Figure 10:
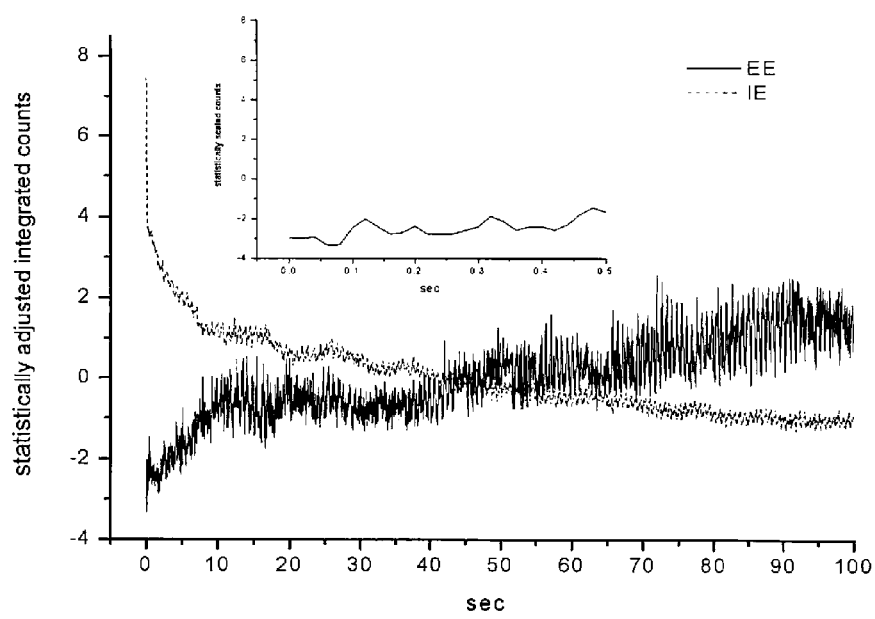

FIG. 10 shows integrated total inelastic scattered light+ fluorescence, i.e. IE, and integrated total elastic scattered light, i.e. EE, as a function of time for a single very short and weak mechanical impulse; i.e. transition from $\approx 0$ g/cm$^2$ to $\approx 25$ g/cm$^2$ in 0.1 sec starting at time t=0 sec, followed by active pressure maintenance at 50 g/cm$^2$. Inset: same data at shortest times.

Figure 11:
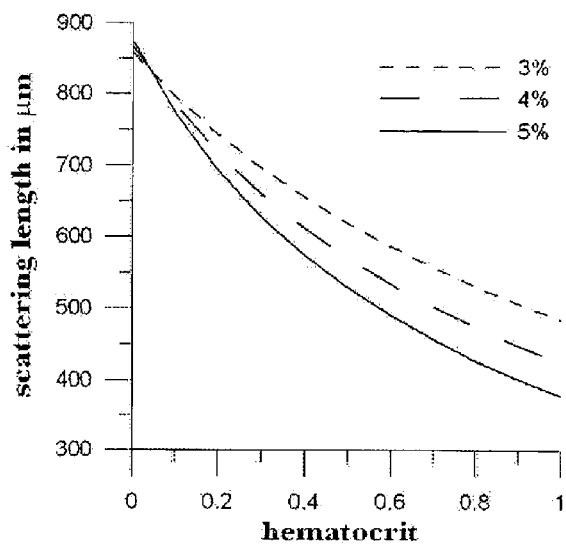

FIG. 11 depicts the calculated scattering length of 830 nm radiation in medium having total blood volume of 3-5% and hematocrit shown on abscissa, with remainder of volume filled with epidermis. Scattering coefficients are taken from Tuchin, 2007, *Tissue Optics*, SPIE Press, Bellingham, Wash.; and Zhang et al., 2005, *J. Biomed. Optics*, 10, 024030.

Figure 12A:
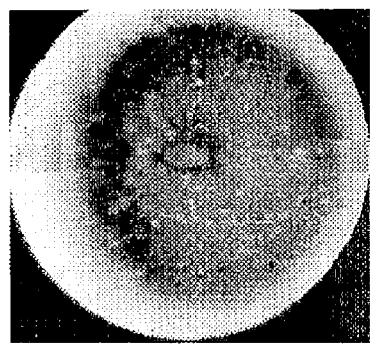
Figure 12B:
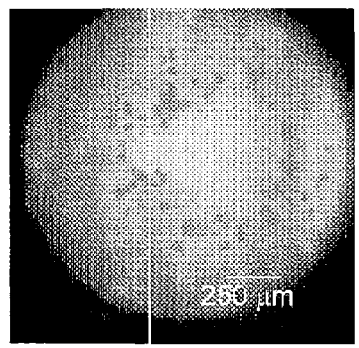
Figure 12C:
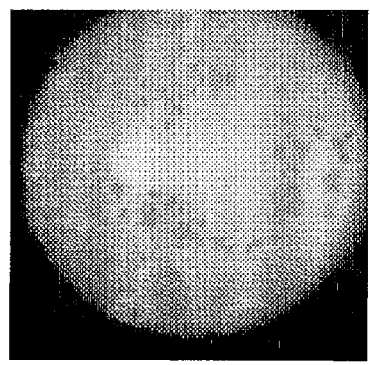
Figure 12D:
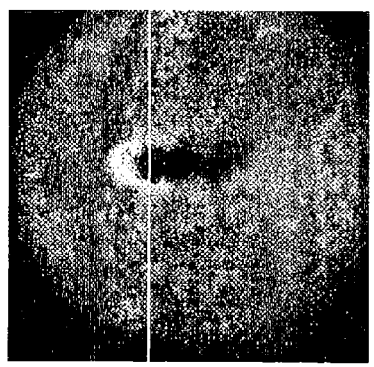

FIGS. 12A-12D are images taken through the aperture of an apparatus of the invention. FIG. 12A depicts a backlit flat Delrin™ block; FIG. 12B shows an unpressed fingertip (pressure~45 g/cm$^2$), showing illumination at center; FIG. 12C shows a fingertip pressed hard (pressure>140 g/cm$^2$), showing displacement of illuminated area; and FIG. 12D shows the difference between the images of pressed (12C) and unpressed (12B) fingertips.

Figure 13:
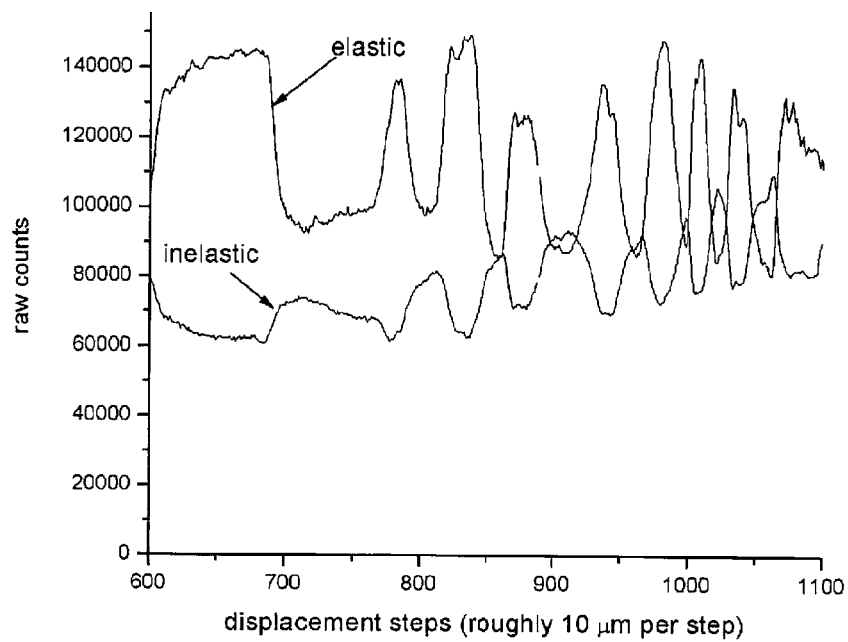

FIG. 13 is a shows raw counts versus displacement steps for EE (elastic) and IE (inelastic) scattered light integrals from scan of laser and detector across fingerprint ridges plotted against displacement of fingertip alone across a stationary aperture.

Figure 14:
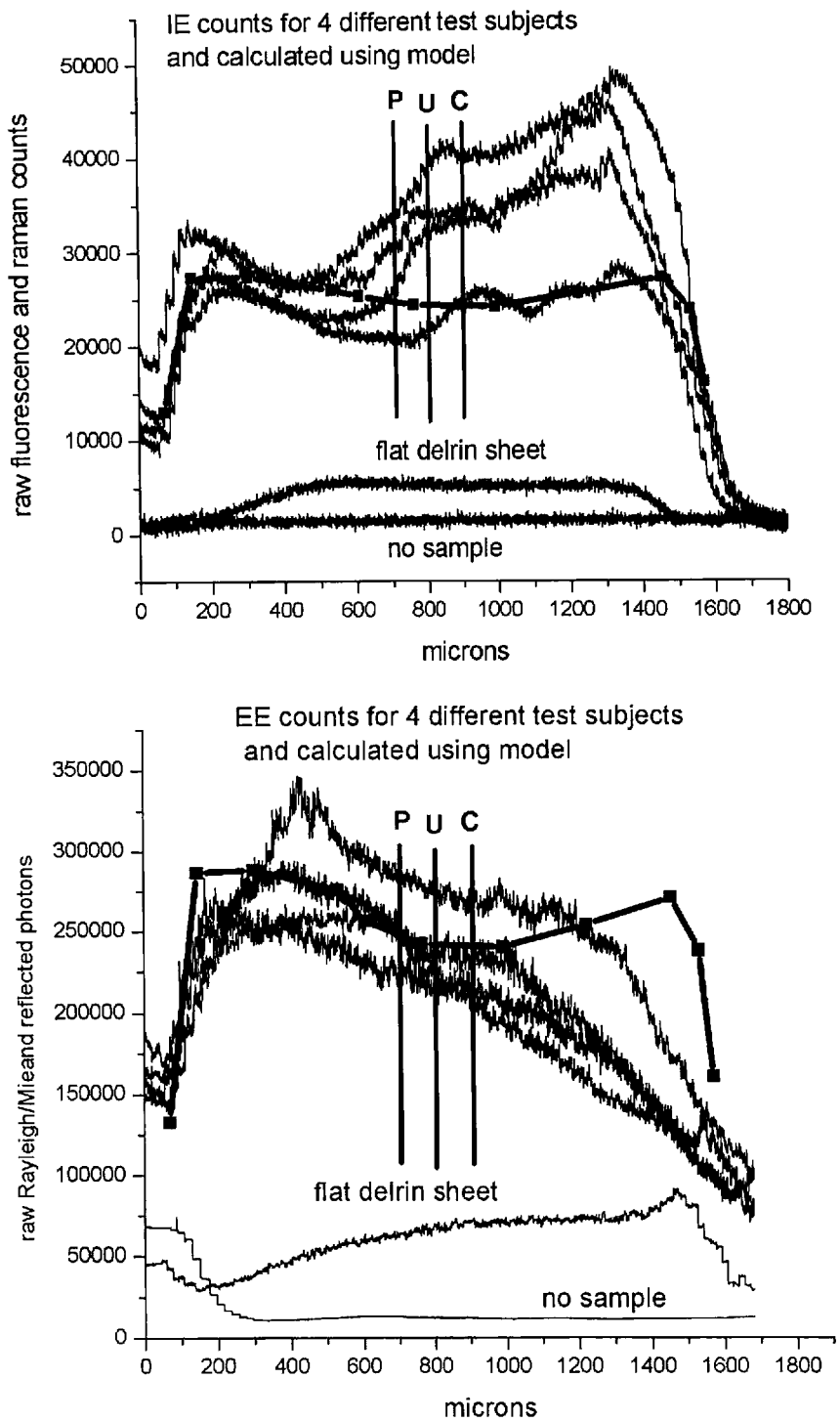

FIG. 14 shows elastic and inelastic scattering integrals (EE and IE) for four human subjects, plotted vs. displacement of the fingertip and aperture relative to the laser beam and the detector (fingertip stationary with respect to the aperture, laser beam stationary with respect to detector). Also shown are the EE and IE for a flat Delrin™ sheet and for a blank (no sample). The calculated EE includes specularly reflected light that increases when the reflected beam scans across the aperture with changing $x_s$. The calculated IE is the EE result without the a specular reflection contribution. Results of calculations described in the text are indicated by thick black lines joining black squares. The positions of the laser entrance point at the different times of a tissue modulation sequence are shown at U, C, and P, as described in the Example.

Figure 15:
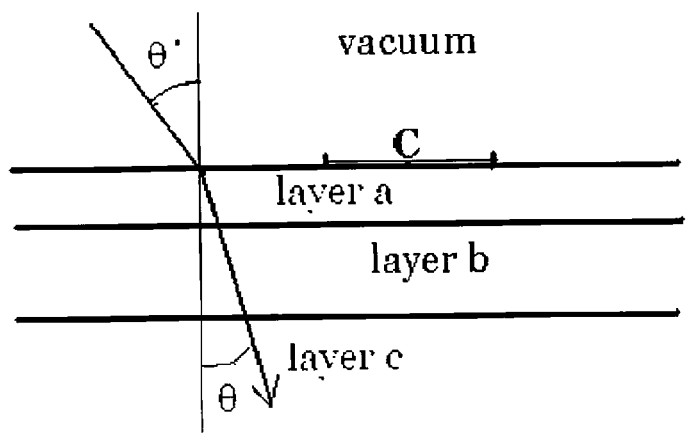

FIG. 15 depicts the geometry of the experiment: radiation is incident on the skin, modeled as three planar layers. The incident beam makes an angle θ' with the outward normal, which is changed to θ inside the skin by Snell's-Law refraction.

Figure 16:
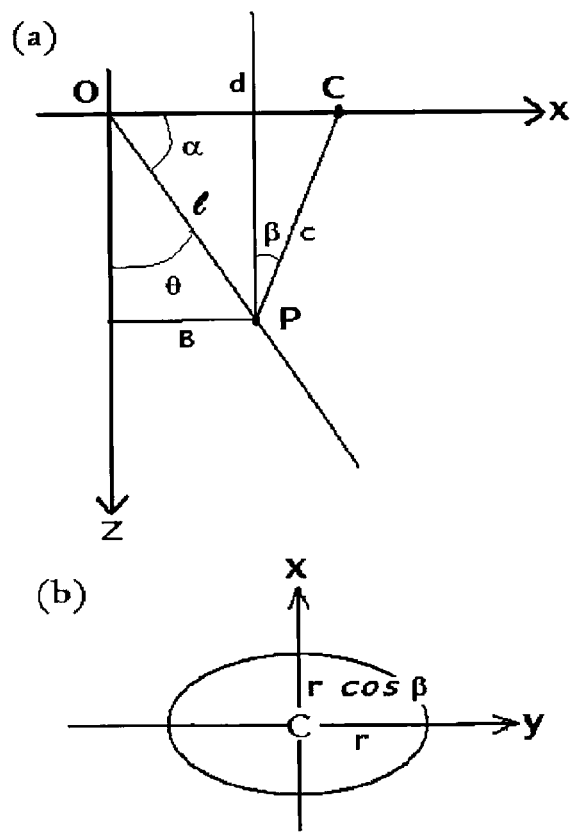

FIGS. 16A-16B depict the geometry of the experiment inside the skin: z=0 is top boundary of layer a, and beam inside skin makes an angle θ with the z-axis. The center of the beam enters the skin at the origin O and propagates a length I to P, where scattering occurs. FIG. 16B provides the top view, showing the projection of the collection circle in a plane perpendicular to PC.

Figure 17:
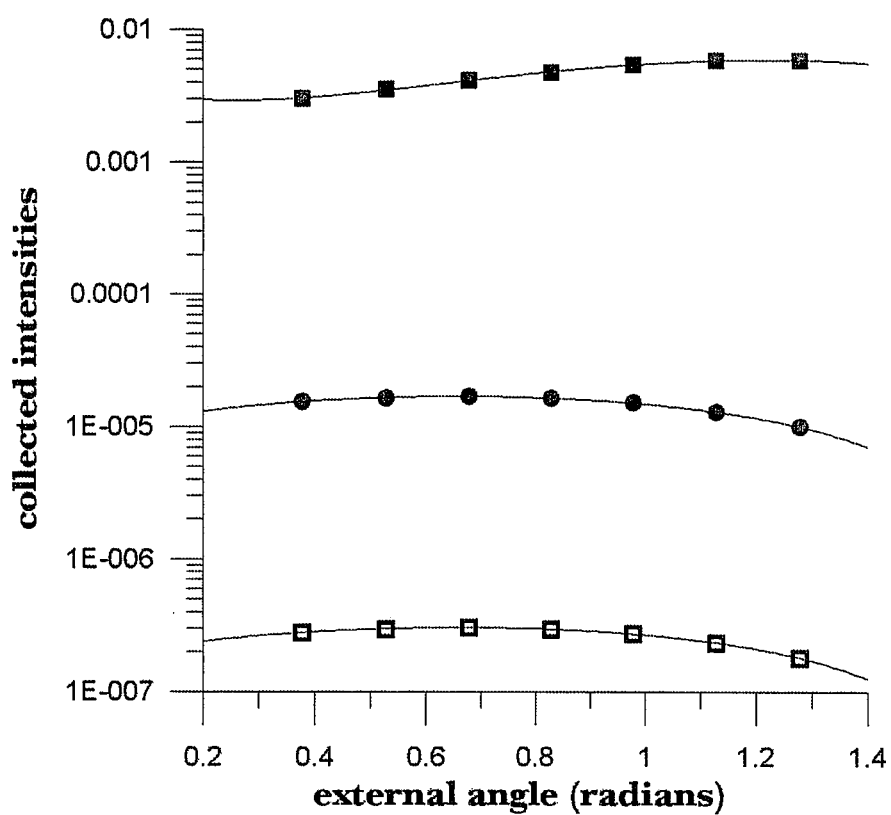

FIG. 17 shows collected intensities as a function of angle between incoming beam and external normal, with distance between beam center and center of collection circle fixed at 100μ. ■=static tissue, ●=red blood cells, □=plasma.

Figure 18:
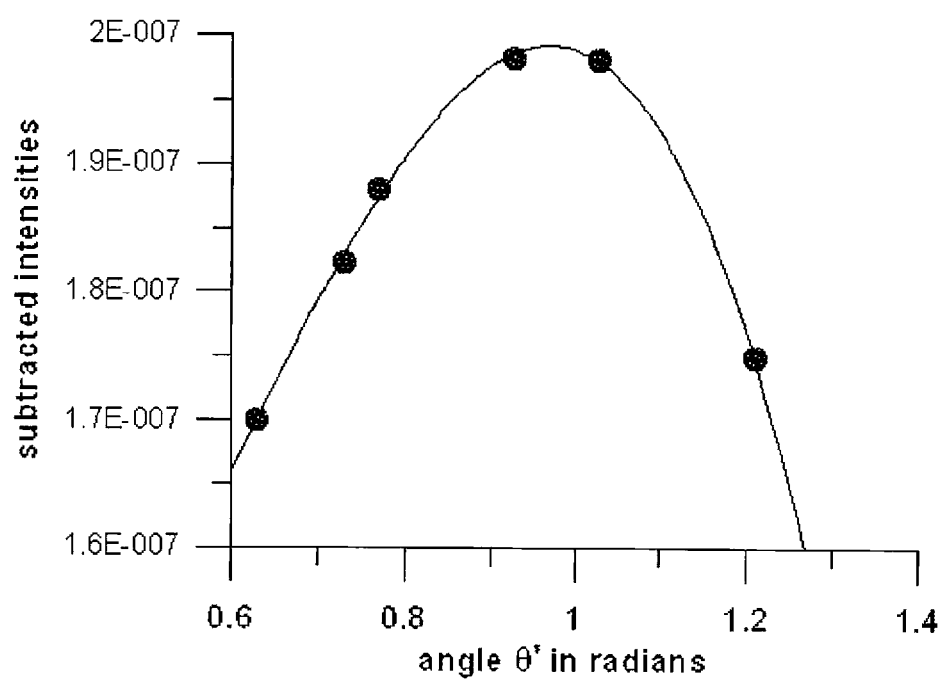

FIG. 18 shows modulated (difference between unpressed and pressed) total intensities plotted against the angle θ', with distance between center of beam and center of detector circle fixed at 200μ. The curve in the figure is a cubic fit, for clarity. The optimum value of θ' is 56.5°.

Figure 19:
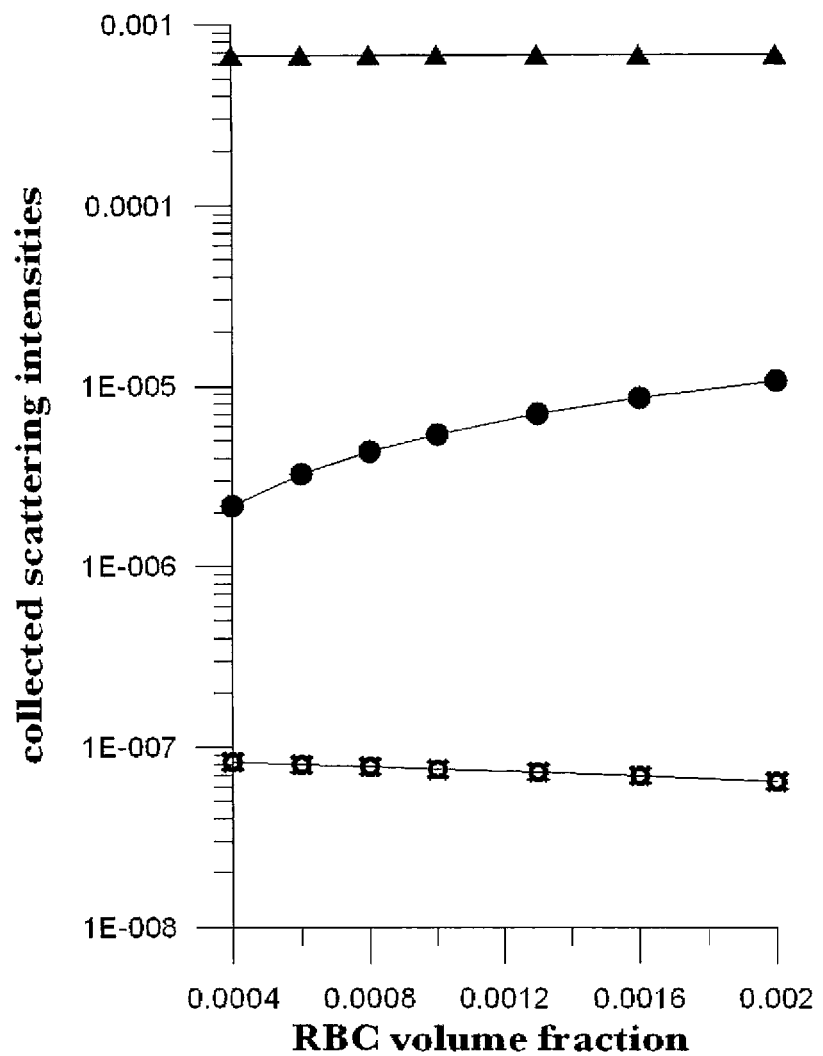

FIG. 19 shows scattering intensities entering collection circle for static tissue (filled triangles), red blood cells (filled circles) and plasma (empty squares), plotted against $\phi_{rb}$. The volume fraction of plasma in layer b in each case is $\phi_{pb}=0.0080-\phi_{rb}$, $\phi_{rc}=\phi_{rb}/6$, and $\phi_{pc}=\phi_{pb}/6$. Collected intensities for static tissue and for plasma decrease linearly with $\phi_{rb}$.

FIG. 20 shows cross-section of spherical dome formed by pressing fingertip into circular hole of diameter D, centered at $x=-x_0$, y=0, z=0. From the maximum height of the dome above the x-y plane, $h_0$, one can calculate the radius of the sphere, $R_m$ (upper panel). The angles θ' and θ indicate the path the beam would take in the absence of doming. Path of beam of scattered radiation from (x,y) to the center of the detector, $(x_d, y_d)$ is shown in lower panel. The angles the beam makes with the normal to the surface are θ (inside skin) and θ' (outside skin), where θ and θ' obey Snell's Law.

Figure 21:
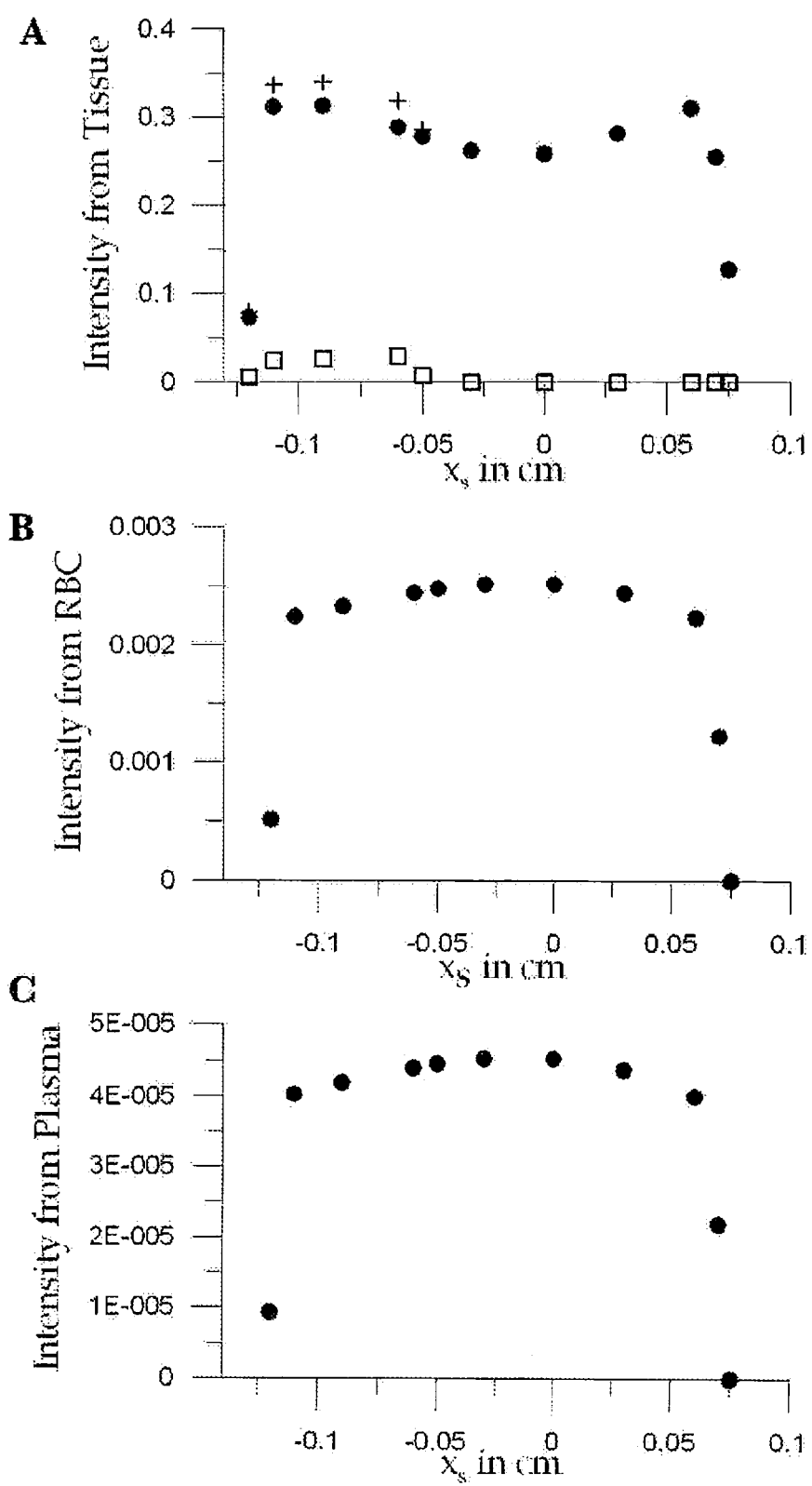

FIG. 21 shows scattered intensity into detector as a function of position of beam source $x_s$, with detector centered at $x_d=x_s+0.022$ cm. Source and detector are at 0.013 cm above z=0. The beam enters at an angle relative to the normal of 0.980 radians. The aperture is at z=0, $0.1 \text{ cm} \leq x \leq 0.1$ cm. Panels A, B and C show scattered intensity from static tissue, red blood cells, and plasma. The empty squares in Panel A give the calculated intensity of specularly reflected light and the x's give the sum of the specular reflected light and the calculated intensity.

FIG. 22A is a profile representing fingertip ridges: double-Gaussian functions with spacing 600μ, width 450μ, shape 30μ, and alternating heights of 120μ, and 60μ.

FIG. 22B: Calculated transmission coefficient averaged over width of beam (/ and error bars) plotted against starting x-value for center of beam above profile (left scale), superposed on the profile.

FIG. 23 is a schematic diagram of an in-vivo LighTouch® measurement device optical layout. Incident light 10 emitted by the laser 12 passes through a clean-up filter 14 and planoconvex focusing lens 16 through an aperture in a steel sheet 18 against which the fingertip 20 to be probed is positioned. Collected light 22 passes through a compound collection lens 24, "razor edge" filter 26, and a refocusing lens 28, to a fiber optic bundle 30 that leads to the spectrograph 32.

FIG. 24 shows results of photobleaching and hydrostatic relaxation study. Condition: A) initial 100 s w/exposure and hydrostatic relaxation; B) second consecutive 100 s w/exposure and hydrostatic relaxation; C) 100 s w/exposure and hydrostatic relaxation following initial 100 s hydrostatic relaxation only, i.e. no laser exposure.

Figure 25:
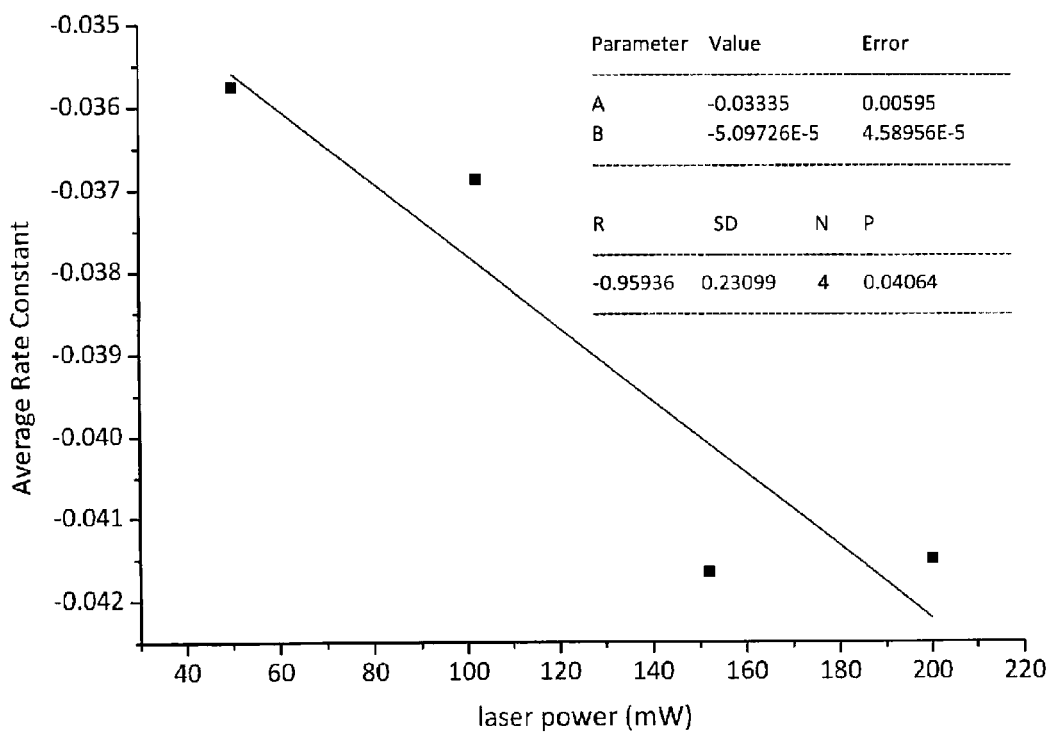

FIG. 25 illustrates a linear fit of averaged decay constants vs. laser powers from 12 data points of two individuals. The applied pressure for an individual was the average of his diastolic and systolic blood pressure regardless of which fingertip was tested.

Figure 26:
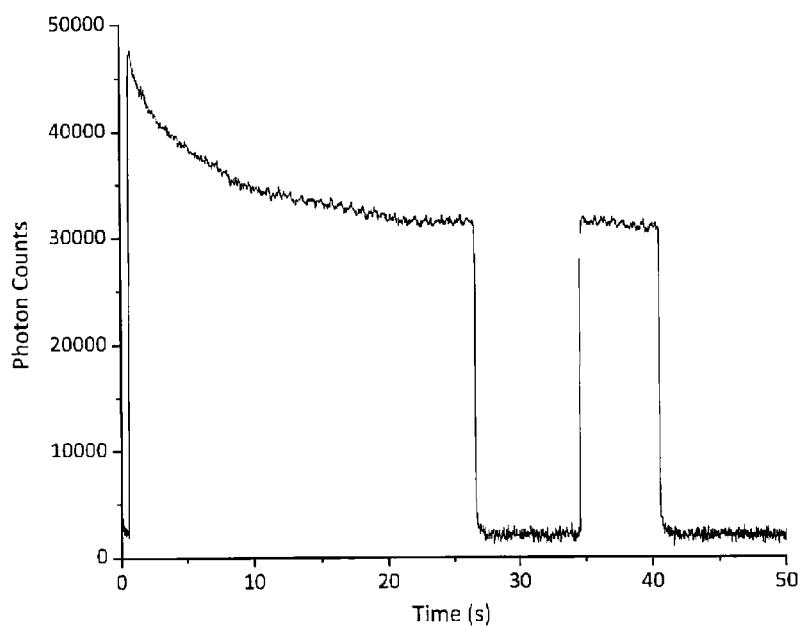

FIG. 26 shows an in-vivo IE profile of a human fingertip, attempting to observe fluorescence recovery by allowing blood to flow into previously probed volume but with laser blocked. If all fluorescence observed at beginning of laser exposure were recoverable due to new blood flowing into probed volume without pervious laser exposure, the fluorescence should return to original value.

Figure 27:
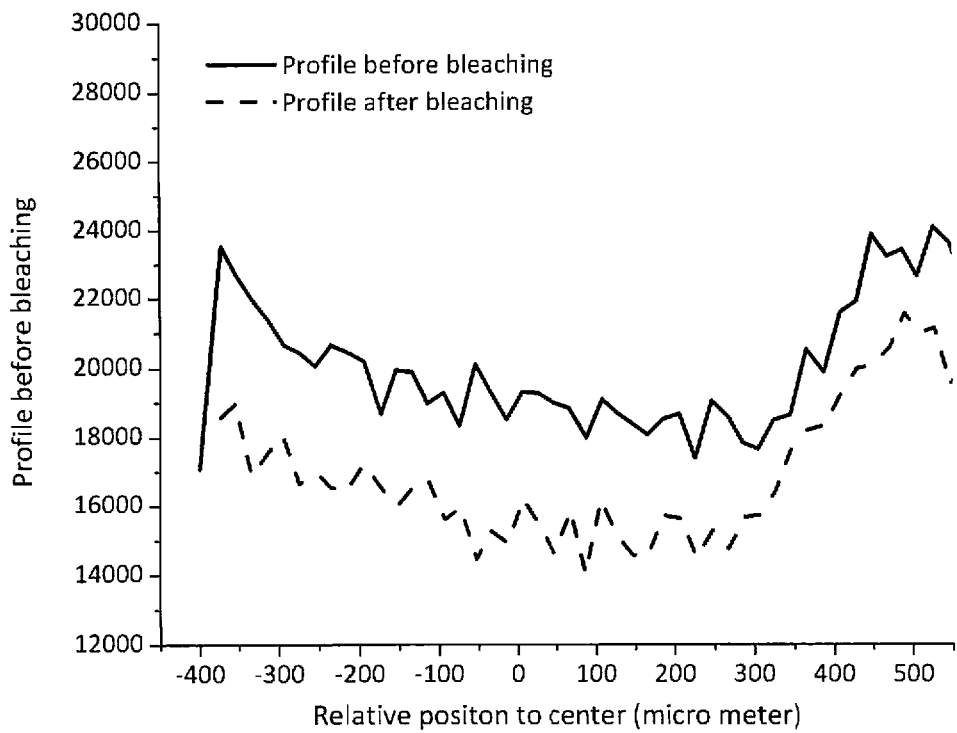

FIG. 27 is an IE profile of two individual in-vivo fingertip scans performed on the same subject without moving hand out in between. The second scan (dotted line) is performed after 50 s bleaching under 200 mW laser exposure at the end of the first scan (solid line).

Figure 28A:
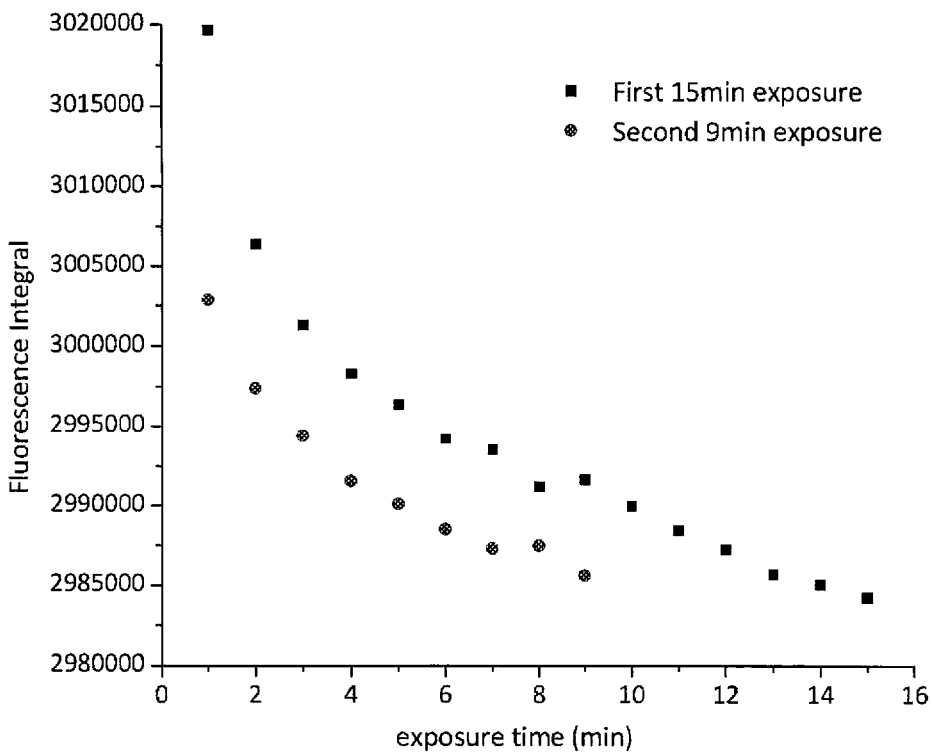

FIG. 28A is a fluorescence profile of in-vitro hemoglobin solution (4.5 g/dL) under 450 mW 785 nm laser exposure.

The sample is left in darkness without extra laser exposure for 1.5 hrs for recovery before the collection of the second series of data.

Figure 28B:
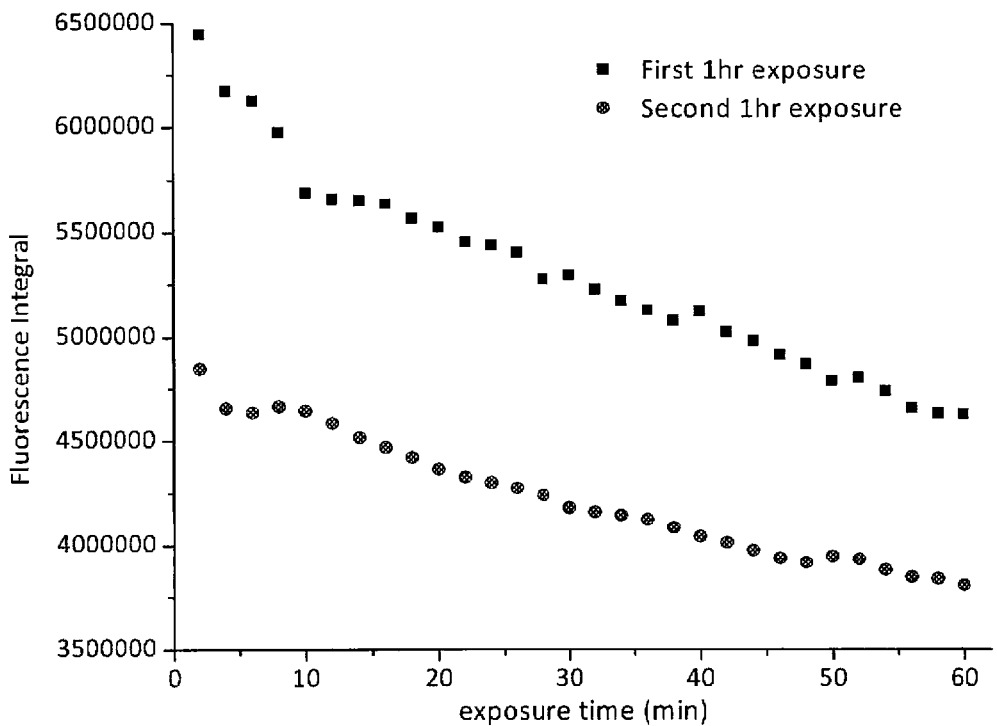

FIG. 28B is a fluorescence profile of in-vitro melanin solution after 200 nm syringe filtration under 450 mW 785 nm laser exposure. The second profile (round dots) is collected after leaving the sample in dark for 2 hrs to recover if there is any. Similar experiments but allowing more than 12 his overnight recovery show comparable results.

Figure 29:
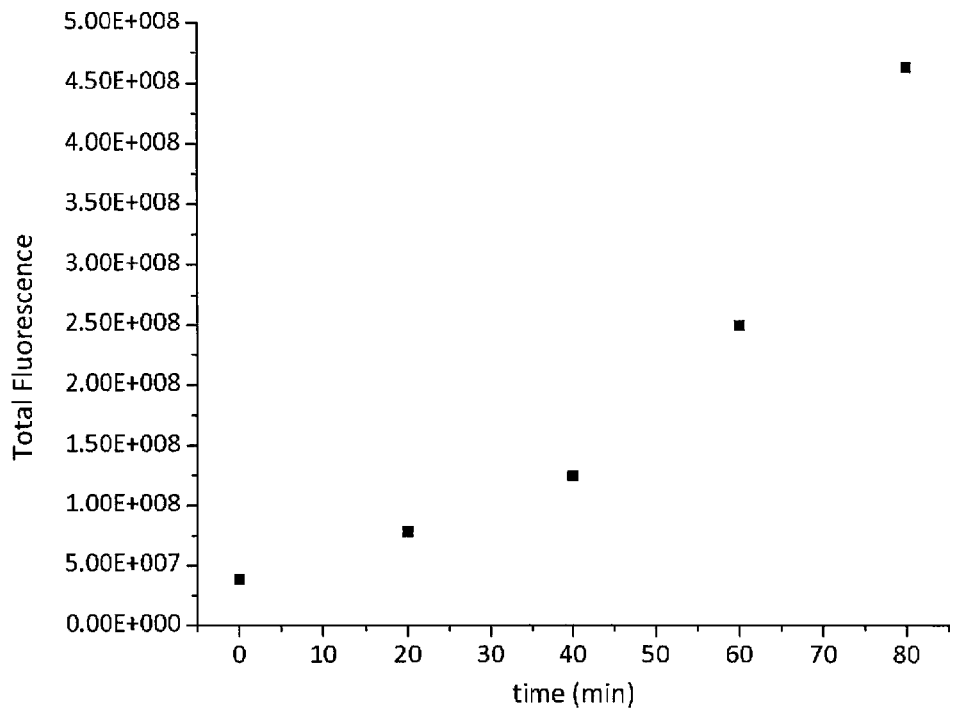

FIG. 29 is a plot of total fluorescence yield across 400-1900 cm−1 Raman shift range for Maillard reaction product at various time points (0 min, 20 min, 40 min, 60 min, and 80 min respectively) along the course.

DESCRIPTION OF THE INVENTION

The invention is based on the development of an algorithm that gives the ratio of the volume of the red blood cells to that of the plasma, allowing direct calculation of hematocrit. A single color of light is incident on vascularized tissue containing phases for which the absorption and scattering coefficients are known, e.g. plasma, red blood cells and static tissue. The elastically emitted (EE) light, with wavelength equal to incident wavelength, and the inelastically produced light, (IE), the wavelength shifted light, are collected simultaneously. These two measurements of light originate from orthogonal processes such that they can be combined using the algorithm.

The method of the invention is advantageous in numerous respects. It is not necessary to separate Raman from fluorescent emissions, as one might expect from other spectral analysis systems. The method of the invention does not require use of a spectrograph, as it can be carried out using filters. In addition to being noninvasive, the method can be practiced anywhere on the body. The method can be performed using fiber optics, allowing one to bring the measurement system to the relevant body part. It allows for the detection of internal hemorrhage without exploratory surgery, as well as monitoring of blood flow in the extremities, making it relevant to a wide range of medical conditions and assessments.

The invention provides a method of using a single incident wavelength on a sample of tissue, in vivo or in vitro, and simultaneously measuring the wavelength shifted and unshifted light that is emitted from the tissue, in order to simultaneously estimate the relative volume of two phases, a predominantly scattering phase (associated with red blood cells) and another phase (associated with plasma), existing in the same probed volume. Provided are the equation and relevant scale factors necessary to measurement of hematocrit in both static and modulated environments. Modulation of tissue to vary blood content occurs via the natural pulse of blood flow or can be effected through application of pressure to create blood depleted and blood replete states in the tissue.

Definitions

All scientific and technical terms used in this application have meanings commonly used in the art unless otherwise specified. As used in this application, the following words or phrases have the meanings specified.

As used herein, "hematocrit" (Ht, Hct or HCT) or packed cell volume (PCV) or erythrocyte volume fraction (EVF) refers to the proportion of blood volume that is occupied by red blood cells. It is normally about 46% for men and 38% for women. It is considered an integral part of a person's complete blood count results, along with hemoglobin concentration, white blood cell count, and platelet count.

As used herein, "phase" refers to materials that occupy volume in the tissue, such as plasma, red blood cells, static tissues.

| Phase | Absorption coefficient | Elastic (Rayleigh) scattering coefficient | Inelastic (fluorescence) scattering coefficient |
|---|---|---|---|
| r = rbc | $\alpha_r = 4.5$ cm$^{-1}$ | $\mu_r = 300$ cm$^{-1}$ | 4.5 cm$^{-1}$ |
| p = plasma | $\alpha_p = 0.3$ cm$^{-1}$ | $\mu_p = 0.60$ cm$^{-1}$ | 0.30 cm$^{-1}$ |
| t = static tissue | $\alpha_t = 5$ cm$^{-1}$ | $\mu_t = 12$ cm$^{-1}$ | 5 cm$^{-1}$ |

As used herein, "Mie limit" refers to electromagnetic radiation interacting with materials having a characteristic size about equal to the wavelength of the electromagnetic radiation. Mie limit scattering typically occurs in the presence of scattering bodies that are approximately 50% of the size of an incident laser wavelength.

As used herein, the "RTE" refers to the radiative transfer equation, which mathematically models the transfer of energy as photons move inside a tissue. The flow of radiation energy through a small area element in the radiation field can be characterized by radiance. The RTE is a differential equation describing radiance, defined as energy flow per unit normal area per unit solid angle per unit time. It can be derived via conservation of energy. Briefly, the RTE states that a beam of light loses energy through divergence and extinction (including both absorption and scattering away from the beam) and gains energy from light sources in the medium and scattering directed towards the beam. Coherence, polarization and non-linearity are neglected. Optical properties such as refractive index, absorption coefficient, scattering coefficient, and scattering anisotropy are taken as time-invariant but may vary spatially. Scattering is assumed to be elastic.

As used herein, "aperture" refers to an opening in a device through which light passes. The opening can be a physical opening, such as a hole in the device, or it can be merely an area that is sufficiently transparent to allow light to pass through. The aperture permits the direction of light onto a target or sample to be probed.

As used herein, "tissue modulation" refers to the modulation of blood flow within a target tissue. The modulation achieves blood replete and blood depleted states within the target tissue.

As used herein, "blood replete" refers to a state in which blood flow through a tissue is unobstructed by, for example, vasoconstriction induced by cooling or the application of pressure. The blood replete state can be enhanced by conditions that increase vasodilation, such as warming.

As used herein, "blood depleted" refers to a state in which blood flow through a tissue is substantially restricted and blood volume is minimized. A blood depleted state can be achieved by, for example, cooling and/or applying pressure to the tissue.

As used herein, "tissue" means any portion of an organ or system of the body, including, but not limited to, skin, capillary beds, blood, muscle, breast and brain.

As used herein, "portion of tissue" refers to an area of tissue that light penetrates, and from which a signal is collected. A "target tissue" refers to an area of tissue that is to be probed for signal collection.

As used herein, "Raman spectra associated with" a given component refers to those emitted Raman spectra that one skilled in the art would attribute to that component. One can determine which Raman spectra are attributable to a given component by irradiating that component in a relatively pure form, and collecting and analyzing the Raman spectra emitted by the component in the relative absence of other components.

Experimental Details

The Examples hereinbelow, particularly Example 1, provide sufficient details to obtain the necessary raw measurements (published as Chaiken et al., 2009, J. Biomed. Opt. 14(5):050505). Those skilled in the art will appreciate variations on the process that would allow incorporation of different parameters as appropriate to adaptation of the process and apparatus to differing tissues and materials.

Additional examples provided below elaborate in detail on how the theory and algorithm disclosed herein can be applied to a specific exemplary embodiment, the volar-side fingertip capillary beds, and how one can identify the contributions of various tissue sources to observed fluorescence.

Theory and Algorithm

In vivo, any volume of viable tissue naturally experiences spatial and temporal fluctuations of blood plasma and red blood cell (RBC) content and so it is useful to think of tissue as a three phase system, i.e. plasma and RBC volume fractions that are mobile and a static tissue volume fraction that is not. Probing tissue with near infrared (NIR) light simultaneously produces remitted fluorescence and Raman scattering (IE) and Rayleigh/Mie light scattering (EE) that noninvasively reveal chemical and physical information respectively about the materials and objects within. The IE and EE obtained by NIR probing yields useful information because the relevant set of optical coefficients describing propagation and attenuation of NIR is such that two of the fractions may be discriminated from each other on the basis of physical and chemical optical properties. Assuming there is no void volume in viable tissue, or at most that there is a constant void volume, permits the calculation of two relative volume fractions, for plasma and red blood cells, from simultaneous measurements of two observables, namely the EE and IE. The numerical analysis provided in Example 1 below shows the underlying phenomenology, whereas the following provides detailed guidance for calculating volume fractions of phases from that kind of raw data. This simple analysis allows a rational calculation of hematocrit and related fluid and tissue fractions from simultaneous measurements of IE and EE.

Figure 1A:
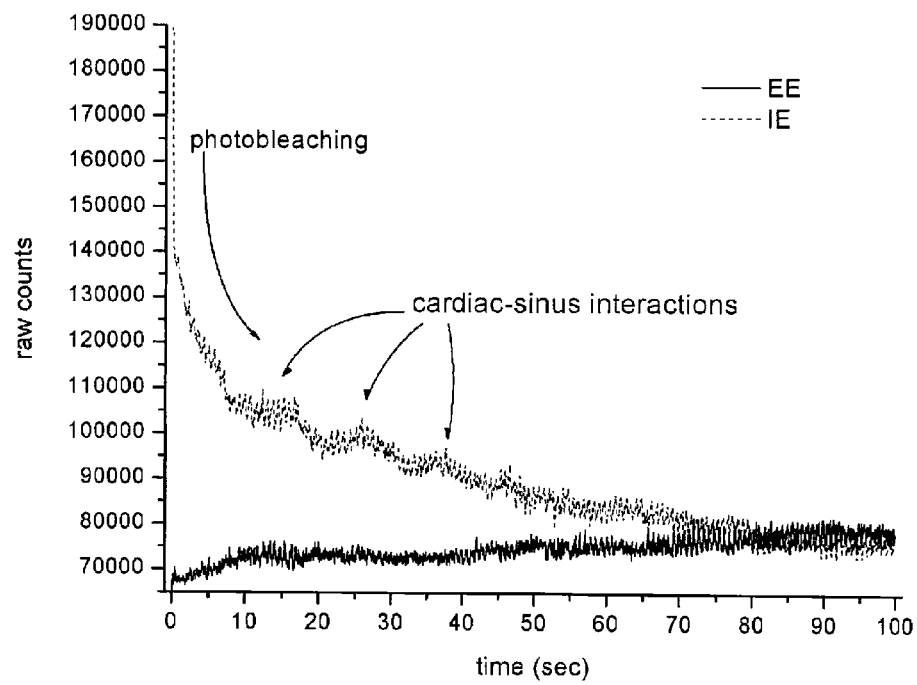
FIGS. 1A-1B depict a typical set of CCD frames integrated to show how the total wavelength shifted remitted light (IE) varies in time relative to the elastically scattered light (EE). The raw IE and EE are obtained by integrating 20 msec CCD frames over Raman shift, i.e. 650 $cm^{-1}$ to 1800 $cm^{-1}$ for IE, and between $-10$ $cm^{-1}$ and $+10$ $cm^{-1}$ for EE. The fingertip was probed with 200 mW of 830 nm excitation while applying constant pressure of halfway between instantaneous diastolic and systolic pressures in order to maintain the skin in registration with the optical system. There was no laser light present on skin while skin was placed in registration, i.e. laser was un-shuttered at t=0 sec.

To appreciate the kind of raw information that is available in real time it will be useful to consider some particular data as in FIG. 1. With details explained in the experimental section, FIG. 1 depicts a typical set of 20 msec CCD frames that have been integrated to show how the total wavelength shifted remitted light, that is, the IE varies in time relative to the elastically scattered light, the EE.

Unlike the EE, the short time behavior, i.e. time<100 msec, of the IE is dominated by photobleaching of the static tissues. On a longer timescale, sinus-cardiac interactions can be seen and generally there is complementary behavior of elastically scattered light (EE) versus in-elastically produced light, (IE) during cardiac pulses. Perhaps owing to the fact that the observed EE is dominated by physical optics, i.e. propagation effects that can be dealt with classically, and the IE is dominated by spectroscopic interactions that can only be properly handled using quantum mechanics, they present complementary information.

It is useful to consider the skin as being composed of only a static phase and a two component mobile phase without void volume, and that it is also possible to calculate the hematocrit for each CCD frame. This produces an essentially continuous record that one can experiment with for early detection of internal hemorrhage or other conditions. Simultaneous observation of fluorescence and elastically scattered light has not been previously used to monitor blood flow.

Much of the approach is dictated by empirical observation and the results of modeling, using the radiation transfer equation (RTE), of propagation of near infrared radiation (NIR) in volar side fingertip skin. Understanding the observed elastically (EE) and inelastically (IE) remitted NIR when probing tissue in vivo required adequately accounting for the blood content and flow, including well known microcirculation anomalies. This includes both what occurs as a part of homeostasis, e.g. the cardiac pulse, and also what may occur due to externally applied stimulus, e.g. cold-induced vasodilation, or just the application of the minimum external pressure needed to establish and maintain mechanically stable registration of the tissue to an optical system.

The Model

The present model for the structure of skin is consistent with empirical observations of the importance of blood mobility. It includes a relatively thin (100$\Box$m), static, bloodless outer layer (a), covering a somewhat thicker (200$\Box$m) relatively blood rich layer (b), that is bounded from below by a less blood rich layer (c) whose depth is essentially infinite. In applying the RTE, the single scattering limit and homogeneous distributions of the materials in each layer are employed. The physical presence or absence of capillaries is not as important as the mobility they extend to the blood; it is essential that, the motion of RBCs and plasma be accounted for separately.

The fraction of the skin that is not blood, i.e. not RBCs and plasma, is considered "static" in that it deforms under external pressure and does not move. Note that this idea has essentially nothing to do with specific cell types in skin, e.g. melanocytes, keratinocytes, etc. The optical transport coefficients (the set of $\Box_s$ and $\Box_a$) of dermis, epidermis, and even stratum corneum are not very different from each other. The different cell types may have significantly different fluorescence and Raman contributions but with respect to attenuation of the NIR light by elastic scattering and absorption, the particular type of static tissue is a less important distinction. These comments apply specifically to low spatial resolution ($\approx 10^2 \Box$m) probing without the spatial resolution afforded by microscopy or confocal methods for which greater detail may be justified.

The need to account for the effect of blood flow in probing tissue with NIR light becomes even clearer when one considers the composition of each layer as shown in Table 1 and the optical coefficients of plasma, RBCs and static tissue as shown in Table 2. Although the static tissue occupies by the far the largest volume fraction of the probed tissue and so the vast majority of collected EE and IE originates from processes in static tissue, the RBC scattering coefficient is much larger than plasma and static tissue with the result that even small movements of RBCs result in large relative changes in total collected EE, i.e. the greater the RBC volume fraction, the less the total remitted EE. There are related effects on the remitted Raman scattered light but that will be beyond the scope of this paper.

In fact, the contribution to the integrated IE of fluorescence is substantially greater than the contribution of Raman, so unless stated otherwise, only the fluorescence component is considered when referring to the IE in what follows. IE is produced subsequent to an absorption event but also reflects the fluorescence quantum yield so, although the absorption coefficients of static tissue and RBCs are nearly equal and substantially greater than that for plasma, the greater the RBC content the greater the observed fluorescence.

The hematocrit is the ratio of the RBC volume fraction to the sum of the RBC and plasma volume fractions that is, the fraction of the mobile tissues that is RBCs. The two volume fractions can be calculated from the two observables, IE and EE. In order to do this, values for eight scattering coefficients, four for elastic scattering and four for inelastic, must be estimated. How this is done is shown in the next section, in which the algorithm for calculating hematocrit from IE and EE is also presented. In the final section, some recent in vivo human clinical results are presented that illustrate the use of this algorithm.

The Algorithm

The model permits calculation of the intensity of scattered radiation from all three phases that is detected outside the skin, given volume fractions, absorption coefficients, and scattering coefficients for the three phases. It accounts for the variation in detected intensity with geometric parameters (placement of source and detector, etc.) and changes in volume fractions. A base calculation must be performed using the model in order to obtain some relations between the coefficients that enter the algorithm. Of course the parameters that enter the calculation differ somewhat between individuals, excessive emphasis is not placed on their exact values; the numerical relations derived are only slightly affected by the variation.

Based on earlier experiences with a range of actual skin types and a specific experimental apparatus, for the base calculation, geometric parameters are used as follows: The dome formed when the fingertip is brought into registration with the 0.21 mm diameter optical aperture is assumed to be a spherical cap with radius 0.1 cm and height 0.005 cm. The origin of coordinates is in the center, 0.005 cm below the top of the dome. The angle between the direction of the incoming beam and the vertical is 0.980 radians, and the origin of the beam is chosen so that the center of the beam crosses the skin surface at the top of the dome (actually at x=0.0025404 cm, y=0.004997 cm). The detector center is at x=0.015 cm, y=0.013 cm.

The values of the parameters characterizing the skin for the simulations are given in Tables 1 and 2. The parameters used in calibrating the algorithm in this paper are given in Table 3 and are somewhat different from those in Table 2. The differences were based on the original authors' indications of the effect of isolating the tissues from their normal in vivo setting and were needed to obtain agreement with empirical observations. It should not be assumed that the parameters given are necessarily optimized.

The volume fractions in Table 1 are based on estimates of the average capillary density, dimensions and a hematocrit of 0.10 for the blood in the most vascularized second layer. The third layer was given 10% of the total blood fraction of the second layer, i.e. from the top of the capillary loops down to the superficial dermal plexus, consistent with medium to deep dermis. The calculations show that, for all three phases, the contribution of layer c is much less than that of layers a and b, so that the assumptions made for layer c are not critical. Even if the total blood fraction is assumed to be as high as 0.05, the scattering length is very long compared with the dimensions of the layers and the single scattering limit is appropriate. For the calibration of the algorithm given below, volume fractions used were consistent Jacques' estimates for well perfused skin, as would be appropriate to fingertips. The estimates in Table 1 are more appropriate of forearm skin.

TABLE 1

Assumed volume fractions of the three phases in the three layers

| Phase | Layer a | Layer b | Layer c |
|---|---|---|---|
| p = plasma | 0.00 | 0.0072 | 0.001200 |
| r = red blood cells | 0.00 | 0.0008 | 0.000133 |
| t = static tissue | 1.00 | 0.9920 | 0.998667 |

TABLE 2

Absorption and scattering coefficients for the three phases

| Phase | Absorption coefficient | Elastic (Rayleigh) scattering coefficient | Inelastic (fluorescence) scattering coefficient |
|---|---|---|---|
| r = rbc | $\alpha_r = 4.5$ cm$^{-1}$ | $\mu_r = 300$ cm$^{-1}$ | 4.5 cm$^{-1}$ |
| p = plasma | $\alpha_p = 0.3$ cm$^{-1}$ | $\mu_p = 0.60$ cm$^{-1}$ | 0.30 cm$^{-1}$ |
| t = static tissue | $\alpha_t = 5$ cm$^{-1}$ | $\mu_t = 12$ cm$^{-1}$ | 5 cm$^{-1}$ |

In the present model, the sum of the absorption and inelastic scattering coefficients, weighted by phase volume fractions, are added to give the attenuation coefficient for each layer. The calculated elastic scattering intensity from each phase is proportional to the corresponding elastic scattering coefficient, and the inelastic scattering intensity is proportional to the inelastic scattering coefficient times a quantum yield. The volume fractions (see Table 1) add up to unity, implying that there are no voids.

This is summarized in equations [1] and [2] using $\phi$ for each of the volume fractions, i.e. RBCs, plasma and static tissue.

$$1 = \phi_r + \phi_p + \phi_s \quad [1]$$

$$0 = d\phi_r + d\phi_p + d\phi_s \quad [2]$$

in any phase. Good agreement between theory and experiment was obtained by summing the contributions from each phase and each layer. Obviously, one can measure only the total elastic and inelastic scattering, but one can calculate the separate contributions, as shown below. It is clear that, because of the increased path length and attenuation, the contribution of layer c is unimportant. The calculations show that the scattering from any phase is a linear function of the volume fraction of that phase in layer b. Thus, it is the blood volume fractions in layer b that are measured; the hematocrit involves volume fractions in layer b.

$$Hct = \phi_r / (\phi_r + \phi_p) \quad [3]$$

Based on the results of many calculations with the model, it is assumed that the observed elastic and inelastic scattering intensities are linear functions of the volume fractions of the three phases in layer b. Using [1], one may write this as $$EE = \aleph_1 + \aleph_2 \phi_p + \aleph_3 \phi_r \quad [4]$$

$$IE = \aleph_4 + \aleph_5 \phi_p + \aleph_6 \phi_r \quad [5]$$

The linear dependence is both direct (the amount of scattering from any phase at any point is proportional to the volume fraction of that phase at that point) and indirect (the scattering is proportional to the incident light intensity, which is determined by the attenuation, and the light reaching the detector is attenuated as well). It is important to note that the observed values of EE and IE depend on how they are measured and geometrical parameters of the system. In particular, the yield of measured scattered photons depends on the probed volume, the frequency range considered, and the incident laser flux. However, relations between the first three $\aleph_j$ and relations between the second three $\aleph_j$ can be obtained from the model calculations.

A series of calculations using the model were performed to obtain elastic and inelastic scattering with values of $\phi_r$ and $\phi_p$ centered around 0.004 and 0.036 respectively. ($\mu_t$=25, $\alpha_r$=150, quantum yield=1E−5). It was verified that both calculated elastic and calculated inelastic scatterings were linear in the volume fractions ($r^2 \geq 0.999$). The best bilinear fits were (C indicates calculated quantities):

$$EC = 0.313583 - 0.108563\phi_r + 0.045209\phi_p$$

$$IC = (0.631030 + 14.83102\phi_r + 0.263197\phi_p) \times 10^{-5}$$

Since EE is proportional to EC and IE is proportional to IC, the ratios of $\aleph_2$ and $\aleph_3$ to $\aleph_1$, and the ratios of $\aleph_5$ and $\aleph_6$ to $\aleph_4$ are now known. One can thus write;

$$EE = \aleph_1(1 + 0.144427346202\phi_p - 0.346202\phi_r) \quad [6]$$

$$IE = \aleph_4(1 - 2.298501\phi_p + 20.889993\phi_r) \quad [7]$$

And that leaves only two parameters to be determined. These are essentially normalizing parameters. Since the calculations refer to $\phi_r$=0.0040 and $\phi_p$=0.0360, $\aleph_1 = EE_0/1.003815$ and $\aleph_4 = IE_0/1.000814$, where $EE_0$ and $IE_0$ are measured at some reference point with respect to the measurement conditions, i.e. a particular applied pressure relative to the test subject's diastolic and systolic blood pressures or perhaps a particular temporal position with respect to the cardiac pulse. Any choice should be based on measurement conditions that actually produce the assumed set of volume fractions defining the model calculation.

Possibly, future experiments can be done in which the volume fractions can be measured independently and associated with particular values of $EE_0$ and $IE_0$, thereby providing independent absolute calibration for this measurement approach. The stated goal was a continuous real-time record of hematocrit (or some other rational function of the relevant blood fractions), in order to log temporal changes and reactions to external probing/examination. Differences in the skin optical properties across individuals are expected to affect the absolute values of the measured volume fractions but this does not diminish the value in monitoring their relative variation in time.

Solving [6] and [7] for the volume fractions gives $$\phi_r = 1.034740\left(1.003815\frac{EE}{EE_0} - 1\right) + 0.065018\left(1.000814\frac{IE}{IE_0} - 1\right) \quad [8]$$

$$\phi_p = 9.404260\left(1.003815\frac{EE}{EE_0} - 1\right) + 0.1558538\left(1.000814\frac{IE}{IE_0} - 1\right) \quad [9]$$

The Hct is then given by [3]. Note that if $IE=IE_0$ and $EE=EE_0$ these equations yield $\phi_r$=0.0040, $\phi_p$=0.0360. Thus one can calculate the two volume fractions, $\phi_r$ and $\phi_p$, from measured quantities, and then obtain the hematocrit.

Representative Results

The apparatus and methods are detailed in the Examples hereinbelow. The most salient details are included here only as needed in the context of particular data. Saturation of the CCD response, particularly by the EE is to be completely avoided both for the safety of the CCD and because some CCDs produce an insidious artifact where the EE and IE move in opposite directions much as is displayed in FIG. 1 and elsewhere, when the EE is very saturated at even just a few pixels. Care has been taken to avoid this artifact in the work presented here.

Figure 1B:
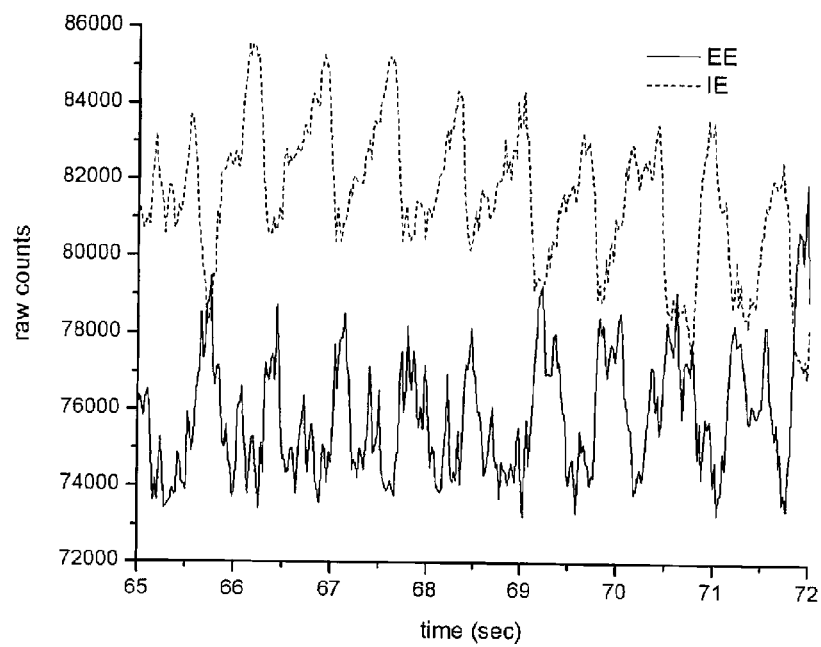
Figure 2:
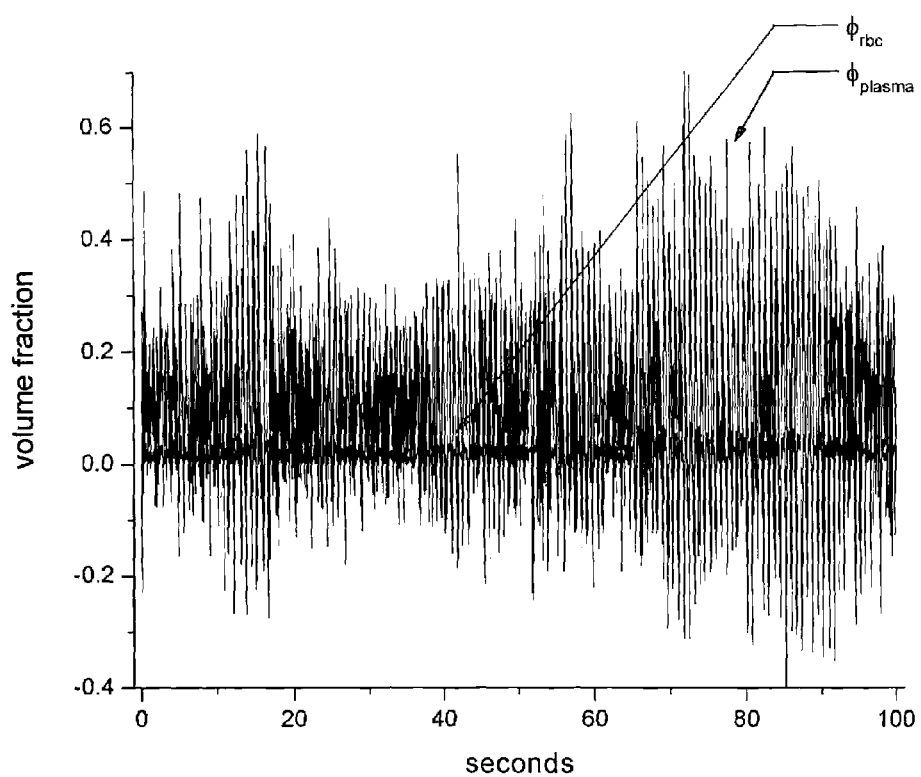
FIG. 2 depicts calculated volume fractions for RBCs and plasma using data in FIG. 1 and equations [8] and [9], and 51 pt adjacent averaged data as reference $IE_0$ and $EE_0$ levels.
Figure 3:
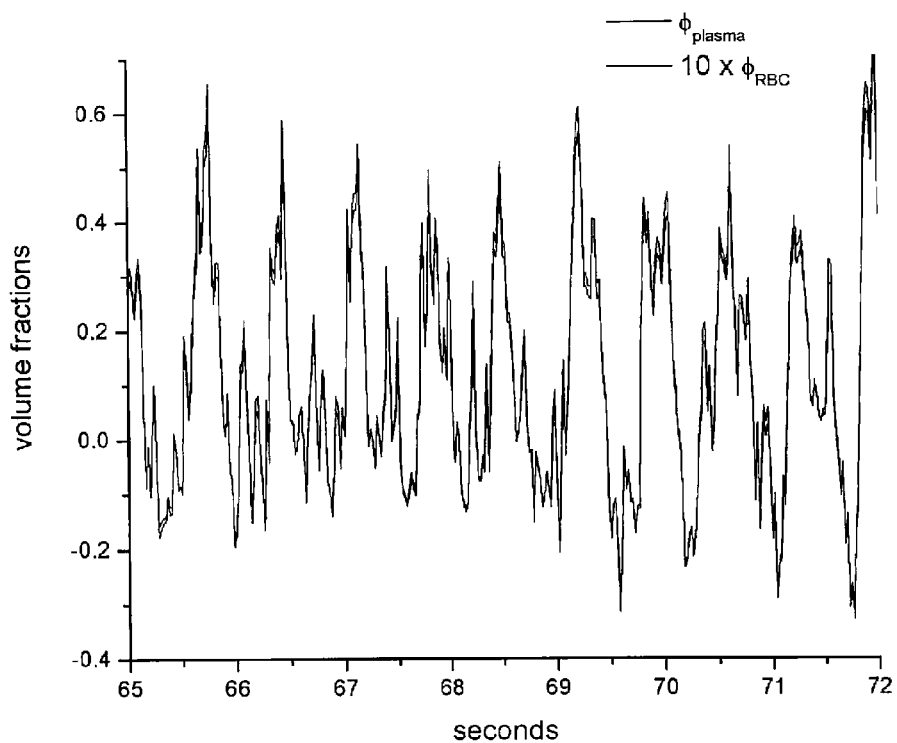
FIG. 3 depicts the same calculation results as FIG. 2, but showing data on same timescale as FIG. 1B. The RBC fraction is multiplied by 10 nearly accounting for the Hct value, to facilitate visual comparison of the time dependence of the two fractions. Note that the volume fractions are nearly coincident in time.

In FIGS. 2 and 3, the measured set of EE and corresponding IE in FIG. 1 were combined using [8] and [9] to calculate the RBC and plasma volume fractions. To minimize the effect of the photobleaching on the calculations, $IE_0$ and $EE_0$ were calculated as a function of time by performing a 51 pt adjacent averaging smoothing on the IE and EE respectively. For each data point in the IE and EE, a corresponding set of $IE_0$ and $EE_0$ could be assigned from the corresponding smoothed data.

If one uses the same attenuation coefficients and volume fractions as were used for the original model and appropriate for forearm skin, values of the volume fractions have more negative values and/or are unrealistically large. Adjusting the total blood volume fraction to 4% and changing the scattering coefficients in a manner consistent with the cited literature authors' expectation of possible error gave the results shown in FIGS. 2 and 3. No attempt was made to optimize the value of any particular parameters, but arbitrary parameters cannot be used to implement this algorithm in order to produce physically realizable volume fractions.

Figure 4:
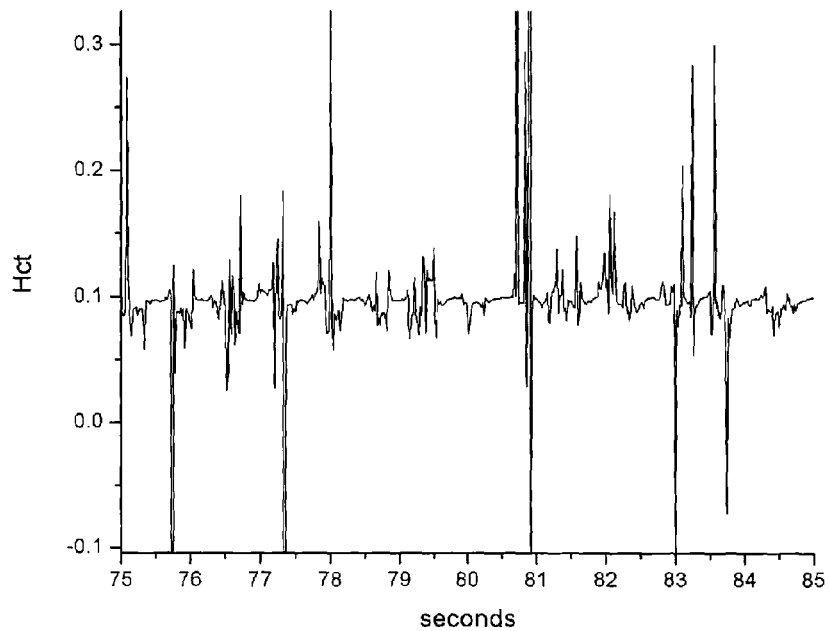
FIG. 4 depicts the calculated Hct value using volume fractions in FIGS. 2 and 3.

Even for the parameters employed, the volume fractions sometimes take negative values, and for these times the volume fraction of skin is greater than 1. As can be seen in FIG. 4, the hematocrit is only affected near a time when one or both volume fractions crosses 0. This occurs when nearly dividing by zero but averaging over the entire time series without dropping any points, the standard errors of the mean values, i.e. $\phi_{rbc}$=0.004 and $\phi_{plasma}$=0.036 over time were 6% or less for the fractions and 17% for the Hct value, 0.08268.

Given that the RTE model may give inadequate results to allow calculation of internally consistent $\aleph_{1-6}$ the following is an example of how to calibrate the algorithm empirically. For this purpose [8] and [9] can be written as below.

$$\phi_r = a + \left(b\frac{EE}{EE_0}\right) + \left(c\frac{IE}{IE_0}\right) \quad [10]$$

$$\phi_p = d + \left(e\frac{EE}{EE_0}\right) + \left(f\frac{IE}{IE_0}\right) \quad [11]$$

There are now 6 parameters, a, b, c, d, e and f for which one must obtain numerical values in order to produce a time record for the phase volume fractions and ultimately the hematocrit using [3]. This can be done by obtaining constraints based on the empirical data or by assumptions in some cases. First, it is assumed that $\phi_{rbc}$=0.004 and $\phi_p$=0.036 on average so that $EE_{ave}$=$EE_0$ and $IE_{ave}$=$IE_0$. So on average a+b+c=0.040 and d+e+f=0.036. These equations constitute 2 constraints meaning that either d or e can be expressed (calculated) in terms of f, and either a or b can be expressed (calculated) in terms of c. When we can calculate all of a, b, d and e in terms of c and f, we will have enough constraints, i.e. equations, to calculate all parameters in [10] and [11]. Then by varying c and f in such manner as to minimize the difference between the calculated hematocrit at later time t and its value at t=0 one can obtain optimal values of c and f to allow calculation of volume fractions and thereby hematocrit at times going forward and for other test subjects.

Figure 5:
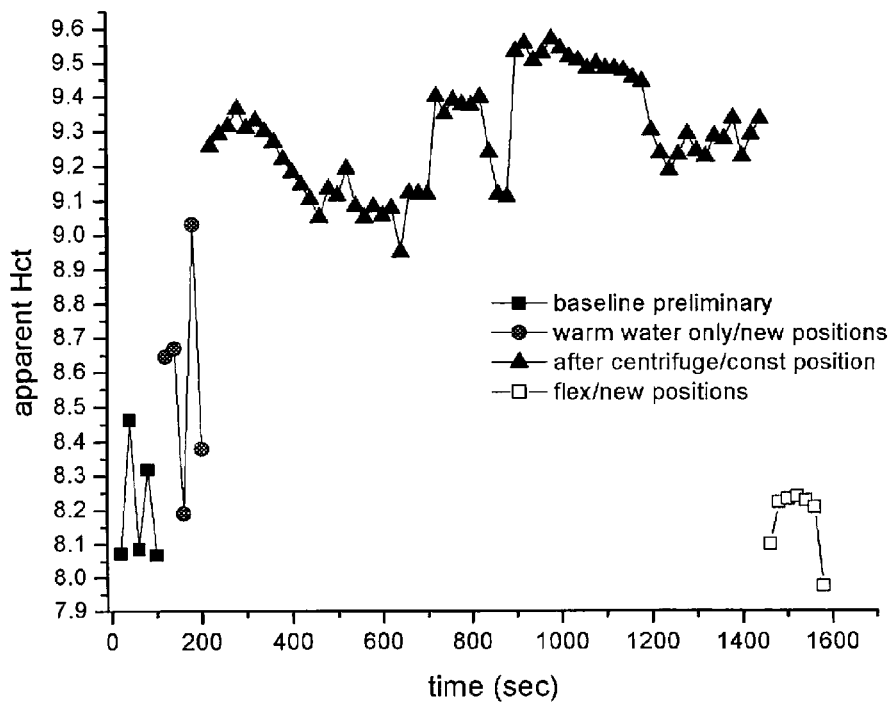
FIG. 5 shows IE and EE as a function time for two different modulation cycles. In one cycle the pressure went from 60 g-force/$cm^2$ to 200 g-force/$cm^2$ and in the other the opposite is true. The black and blue are one pair and the red and green are another. The black and blue sequence was used to provide the calibration in the text.
Figure 6:
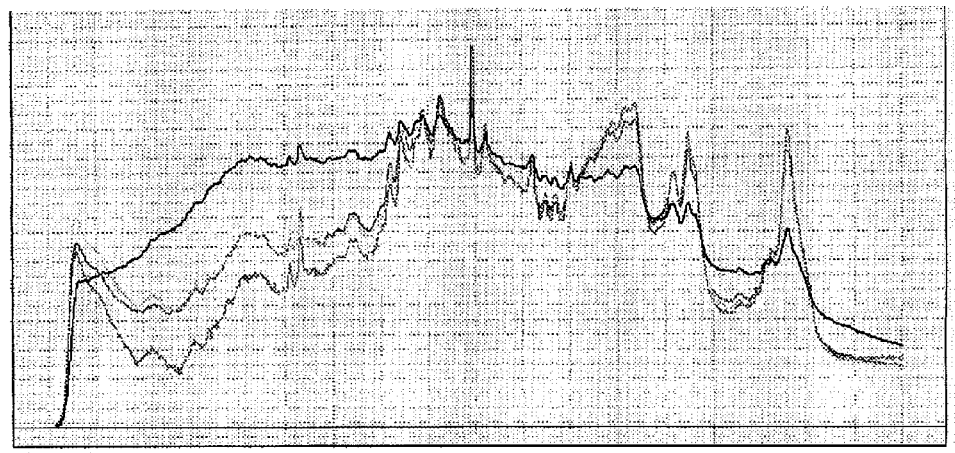
FIG. 6 is an image of a computer display screen depicting a series of tissue modulated difference spectra showing the effect of monotonically increasing the pressure in the pressed stage so as to produce different discharge hematocrit in each case for use in the calibration procedure. On the basis of the appearance of these spectra and the ratio of the integrated emission from 400 cm$-1$ to 1700 cm$-1$ for the higher pressure data to the lower pressure data one can guess the change in $\phi_{rbc}$ and $\phi_p$ needed for the calibration procedure.

Second, FIG. 5 shows the behavior of IE and EE when a skin sample in vivo is subjected to a tissue modulation cycle. Although other pressure based tissue modulation sequences are possible, FIG. 5 was obtained by having the fingertip engaged with a minimum of pressure, i.e. as "unpressed" as possible, and then at a later time a pressed condition was applied in order to move blood. The IE and EE shows what the RTE model also mimics—an increase of EE from ≈65000 counts to ≈67000 and a decrease of IE from ≈32000 counts to ≈29000 counts. Based on the appearance of the tissue modulated spectra obtained from this data as shown in FIG. 6 below, the modulation produced a decrease in $\phi_{rbc}$ fraction by roughly 95% and a decrease in plasma fraction by roughly 90%. All of these observations constitute four constraints on the six parameters.

Third, assuming the hematocrit is constant during the calibration period, e.g. Hct=0.1 consistent with the initial estimate of $\phi_r$ and $\phi_p$, nonlinear least squares (Excel Solver, or Mathcad genfit or old Lotus software are all quite adequate for this purpose) are used to choose the remaining two free parameters to make the calculated hematocrit as constant as possible, i.e. minimize the standard deviation of the Hct over the calibration period, i.e. calculate the Hct for each pair of EE and IE obtaining $\phi_r$ and $\phi_p$. and from that calculate a set of HCT values from which a mean and standard deviation can be calculated. For this procedure to succeed, it is essential that at least one of the constraints correspond to circumstances for which the prevailing Hct is actually different from the assumed value. Without incorporating the empirically observed range of IE and EE variation for a case in which the Hct does change, there is no such information in the algorithm and the least squares procedure will always produce Hct of the assumed value regardless of the data.

Note that the data in FIGS. 5 and 6 do not correspond to the same data in FIG. 1. All that is required is to know the fractional changes in EE and IE that occur for a specific fractional change in $\phi_{rbc}$ and $\phi_p$. These changes can be guessed based on observation as in FIG. 6 or independent measurement by some other method altogether.

Figure 7:
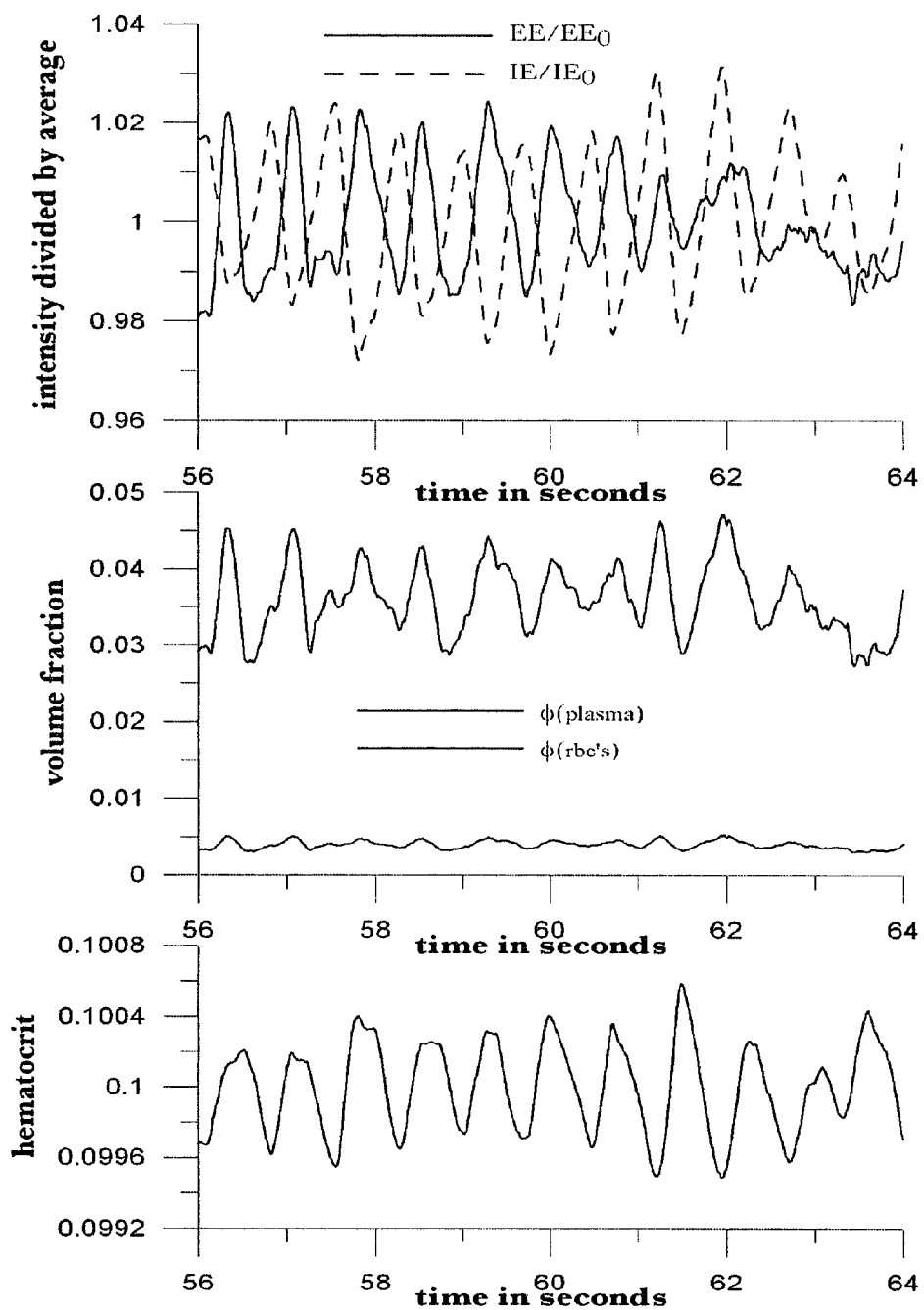
FIG. 7 is calculated Hct and phase volume fractions for data in FIG. 1 using procedure outlined in text and modulation results in FIGS. 6 and 7 to estimate parameters.
Figure 8:
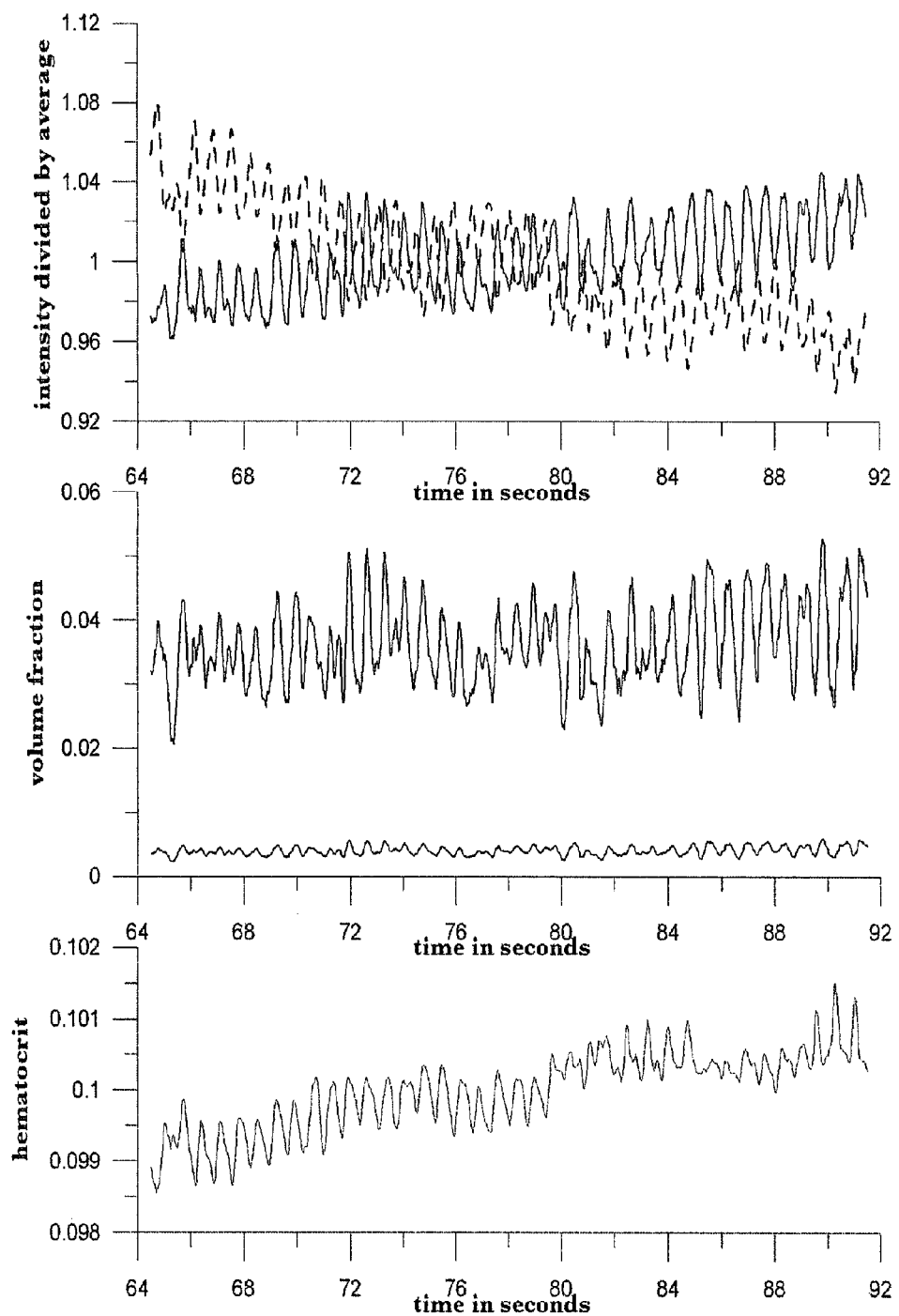
FIG. 8 calculated Hct for data 64.5<time<91.5 sec in FIG. 1 using all the same parameters obtained for 56<time<64 sec.

In order to apply this method to the data in FIG. 1, the data from 56 to 64 seconds were taken as the standard. Eleven-point smoothing, and calculation of $EE/EE_0$ and $IE/IE_0$ were then performed, where the $EE_0$ and $IE_0$ were taken as the averages over the whole time period. The parameters are then obtained as described in the text just after equations [10] and [11] to give: a=−0.075996057, b=0.058891307, c=0.02110475, d=−0.693564747, e=0.531613683, and f=0.197951064. Using these parameters gives the top plot in FIG. 7 for the 56-64 second data set. It gives an idea of the deviations one gets: just a couple of per cent. Then the same set of parameters can be used going forward for 64.5-91.5 seconds as shown in FIG. 8.

EXAMPLES

The following examples are presented to illustrate the present invention and to assist one of ordinary skill in making and using the same. The examples are not intended in any way to otherwise limit the scope of the invention.

Example 1

Simultaneous, Noninvasive Observation of Elastic Scattering, Fluorescence and Inelastic Scattering as a Monitor of Blood Flow and Hematocrit in Human Volar Side Fingertip Capillary Beds This Example describes simultaneous observation of elastic scattering, fluorescence and inelastic scattering from in vivo near infrared probing of human skin. Careful control of the mechanical force needed to obtain reliable registration of in vivo tissue with an appropriate optical system allows reproducible observation of blood flow in capillary beds of human volar side fingertips. Under continuous near infrared excitation, the time dependence of the elastically scattered light is highly correlated with that of the combined fluorescence and Raman scattered light. This is interpreted in terms of turbidity; i.e. the impeding effect of red blood cells on optical propagation to and from the scattering centers and the changes in the volume percentages of the tissues in the irradiated volume with normal homeostatic processes. By fitting to a model, these measurements may be used to determine volume fractions of plasma and RBCs.

There is considerable practical and basic interest in spectroscopic probing of tissue in vivo noninvasively (*Tissue Optics*, Valery Tuchin, SPIE Press, Bellingham Wash., USA 2000). One interest is blood analysis for glucose and other analytes, e.g. bicarbonate, hematocrit (Chaiken, et al., *Proc. SPIE*, Vol. 3918, 135-143, 2000; Chaiken, et al., *J. Biomed. Opt.* 10, 031111, 2005). Technology aimed at noninvasive probing through skin must contend with the variation in tissue optical properties between individuals and for the same person at different times. Used here is an apparatus that allows accurate and reproducible registration of human volar side fingertips with a near infrared (NIR) laser Raman spectroscopic system (Chaiken, et al., Proc. SPIE. Vol. 6093, 609305-1, 2006). By "registration" this includes control of the essentially instantaneous pressure between the skin surface and the aperture or template defining the entrance into the optical collection system. This pressure and the shape of the aperture define a stress field that affects the flow of blood, i.e. plasma and red blood cells (RBCs) in the capillaries. This Example describes observations that are pertinent to the goal of obtaining separate and simultaneous measures of plasma and RBC content in the fingertip capillaries.

The optical properties of the tissues that the incident light encounters are summarized in Table 3. Despite the very low relative volume fraction of RBCs in the irradiated volume, i.e. 0.005-0.003, the values for the optical constants of plasma, red blood cells and other skin constituent materials are such that the net propagation of light is mostly determined by the RBCs. Skin, i.e. "static tissue" that does not move when pressed but instead deforms, has a ten-fold larger scattering coefficient than plasma. The elastic scattering coefficient of RBCs exceeds that of skin by at least a factor of 20 because of the match between the size of the RBCs themselves and the wavelength of incident light.

TABLE 3

Attenuation parameters of basic constituents of skin[1,2,3]

| | $\mu_s$ (mm$^{-1}$) | $\mu_a$ (mm$^{-1}$) |
|---|---|---|
| excitation wavelength 830 nm | | |
| plasma | 0.06 | 0.03 |
| red blood cells (RBCs) | 30.0 | 0.45 |
| static tissues | 1.20 | 0.5 |
| excitation wavelength 805 nm | | |
| plasma | 0.061 | 0.0305 |
| red blood cells (RBCs) | 31.0 | 0.45 |
| static tissues(average skin) | 1.25 | 0.55 |
| excitation wavelength 785 nm | | |
| plasma | 0.062 | 0.031 |
| red blood cells (RBCs) | 32.0 | 0.45 |
| static tissues(average skin) | 1.28 | 0.60 |

[1] Salamotino, et al., J. Biomed. Opt. 11(6) 064026 (November/December 2006)
[2] Jacques, OSA TOPS on Advances in Optical Imaging and Photon Migration, Vol. 2, pp. 364-369, eds. RR Alfano, JG Fujimoto, (Optical Society of America, 1996)
[3] Meinke, et al., J. Biomed. Opt. 12(1) 014024 (January/February 2007)

The inelastic light originates from two distinct processes, fluorescence and Raman scattering. The fluorescence is stronger and ubiquitous and there are overlapping components from all tissues in the irradiated volume, i.e. plasma, RBCs and static tissue. The fluorescence yield per unit volume is different for plasma, RBCs and skin and all yields slowly become weaker and more equal as the excitation wavelength increases from 785 to 830 nm. Associated with the variation in relative quantum yields, the net observed fluorescence yields from the various tissues is somewhat different from the respective behavior of the $\mu_a$ in Table 3. Because they result from fundamentally different physical processes, it is expected that the apparent fluorescence (and Raman) yields differ between RBCs, plasma and skin in a manner that is uncorrelated with the variation in elastic scattering yields across the same tissues. A model which takes these parameters into account should allow one to simultaneously estimate the volume fractions of these tissues, in vivo and non-invasively.

Experimental

Figure 9:
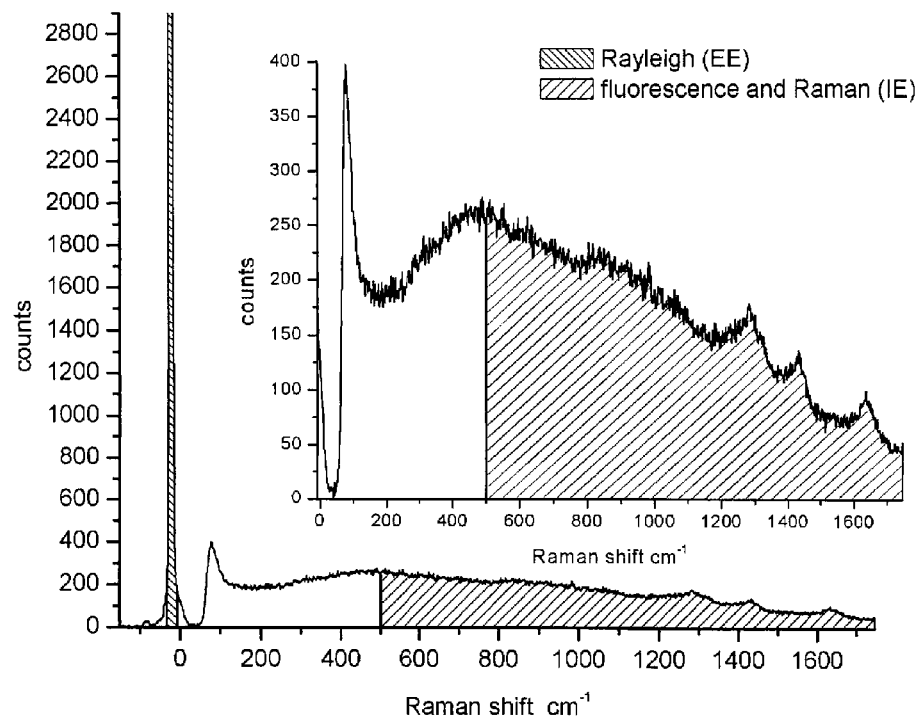
FIG. 9 shows intensity (in counts) versus frequency; in the upper portion: raw typical single 20 msec frame of Andor ccd output with system optimally aligned using 200 mW of 830 nm excitation. In the lower portion: sections of emission used to calculate IE ($\approx$500-1750 $cm^{-1}$) and EE ($-30$-$+10$ $cm^{-1}$).

The experimental apparatus and many experimental details have been previously published (Chaiken, et al., supra, and Proc. SPIE Vol. 6430, 643004, 2007). The upper portion of FIG. 9 shows a raw typical single 20 msec frame of Andor CCD output using 200 mW and 830 nm excitation. The lower portion of FIG. 9 shows the same frame but on an expanded scale to show the sections of emission integrated to obtain combined fluorescence and Raman emission (500-1750 $cm^{-1}$; hereafter referred to collectively as "inelastic emission" or IE) and elastic emission (−30-+10 $cm^{-1}$; hereafter referred to as "elastic emission" or EE). The IE spectral region was chosen to exclude as much as possible of the Rayleigh line and any off-axis reflected light from the outermost stratum corneum. The EE region contains only the elastically scattered light and care must be taken not to exceed the dynamic range or otherwise damage individual pixels of the CCD for this measurement.

To initiate a measurement sequence, a fingertip is brought into contact with a spring steel surface having a 2 mm diameter hole to define an aperture through which a 100 µm diameter laser beam contacts the fingertip, making an elliptical spot. The pressure at this point is 20±5 $g/cm^2$ and is almost imperceptible to some test subjects. Collection and storage of CCD frames is initiated coincident (t=0 sec) on application of a single very short and weak mechanical impulse applied to the back of the fingertip, contacting between the upper joint and cuticle with the end of a rounded smooth Teflon cylinder 5 mm in diameter. The pressure goes from ≈20 $g/cm^2$ to ≈50 $g/cm^2$ in 0.1 sec, equal to 5 CCD frames, defining time t=0 sec. Careful direct observation of the skin surface through the optical system during the entire process shows that the laser spot moves less than 10 µm throughout. The optical system allows the applied force and contact area to be continuously monitored, so that the resulting pressure between the fingertip and the spring steel surface is actively maintained. To a greater or lesser extent, depending on the turgor of the particular test subject, the tissue squashes and flattens, and the contact area increases throughout the experiment thus requiring a proportional increase in force to continuously meet the pressure set point.

The observations are very general, having been obtainable for virtually every person observed. Subjects were from age 8 to 80, with many skin tones and ethnicities, healthy, diseased and of both sexes. Different test subjects require different pressure conditions to properly balance the blood and oncotic pressures. Depending on the tests subject's turgor, an applied pressure between the diastolic and systolic blood pressures is a good starting point for finding optimal conditions.

Results and Discussion

FIG. 10 shows typical data corresponding to the sequence described above. The IE and EE integrals are each plotted as a function of time. The data associated with the vertical axis of each plot was transformed to have a mean of 0 and standard deviation of 1 so as to facilitate their comparison. In the inset, the data for t<0.5 sec are shown. Initially the IE drops rapidly while the EE is nearly constant. FIG. 1B shows some of the same data as FIG. 10 but using an expanded temporal scale to show the complementary and very nearly proportional behavior of EE versus IE light.

The heart-driven pulses in both time records are obvious and can be easily confirmed as such using e.g. a common commercial blood pressure/pulse rate cuff and by doing successive experiments that change the test subject's pulse rate, i.e. varying levels of physical exertion or execution of the Valsalva maneuver. There are regular, longer timescale fluctuations observable in FIG. 10 that are also very reproducible and are at least partially due to known correlations between the heart pulse rhythms and breathing rhythms.

To understand the relative time dependence of the EE and IE data on the timescale of the pulses and faster, two facts are important. First, published in vitro data for 785 nm-excitation of methemoglobin (Hb) over the concentration range spanning the normal capillary blood range demonstrates that the integrated fluorescence, i.e. IE, increases linearly with increasing hemoglobin volume percent (Chaiken, et al., Proc. SPIE, Vol. 4254, 216-227, 2001). At higher concentrations there is a significant photobleaching effect. The analogous dependence for in vitro plasma fluorescence was measured, and it also increases linearly from infinite dilution in Normocarb to pure plasma. Thus fluorescence measured in vivo is a measure of both plasma volume and hemoglobin volume in the irradiated volume.

The second important observation is that, in these experiments, the amount of elastically scattered light collected decreases as the volume percent of RBCs increases. In the dynamic environment of the perfused skin, the volume percentages of the plasma, RBC and static tissues are changing. Radiative transfer theory suggests propagation through a volume containing only static tissue and plasma would not change appreciably because the scattering coefficients are relatively small.

But propagation through a perfused volume may experience much larger changes: the shape and size of the irradiated volume change because of changed RBC volume fraction, since RBC scattering coefficients are so large, and the available light decreases. If, for a heart-driven pressure wave, i.e. pulse, the volume percentage of plasma decreases, then the volume percent of RBCs must increase, even if none actually moved, and the net elastically scattered light collected will decrease.

At the shortest times, when the actuator is establishing control over the pressure applied to the tissue, the behavior of the two plots (substantial decrease in IE with a small relative change in the EE signal) suggests that mostly plasma motion occurs. Since plasma motion out of the irradiated volume without actual movement of RBCs increases the RBC volume percent and causes a decrease in elastically scattered light collected, one can infer that the observed change in IE is due mostly to plasma removal. Apparently the small observed change in EE signal is due to a small movement of RBCs out of the irradiated volume, which keeps the net change in volume percent of RBCs in the irradiated volume very small.

This seems reasonable since in the depth range (see FIG. 10), plasma and erythrocytes are mostly confined to narrow capillaries (<25 μm) and the discharge and tube hematocrit are very nearly equal (i.e. within ≈10%) due to gridlock. Apparently, the effect of a relatively large change in IE due to plasma motion is compensated for by a very small modulation of RBCs so the RBC volume fraction is nearly constant.

Once mechanical equilibrium at the desired preset pressure value has been established, the pulses and other regular temporal oscillations in both the IE and EE data can be easily observed. The IE temporal behavior corresponds to the increasing and decreasing local blood volume as blood pressure pulses propagate through the capillaries in the irradiated volume. The capillaries become slightly distended as an increased volume of plasma and RBCs occupies the capillary lumen during the increasing pressure pulse. Since the fluorescence is more efficiently generated than the Raman signal, fluorescence dominates the IE integral in the experiment. The observed variation in the elastically produced light is explained by the relative magnitudes of the scattering coefficients in Table 3. Since the RBCs have by far the largest scattering coefficient, determined by the physical optics of erythrocytes, the net change of elastically scattered light collected is most strongly associated with RBC movement. Although most of the observed Rayleigh/Mie light originates from static tissue because that tissue has the highest volume fraction, the efficiency of propagation of the excitation light to the static tissue and the efficiency of propagation of the elastically scattered light from the static tissue to the collection zone is decreases as RBC volume percent increases.

The constructed model for the propagation and scattering of radiation through skin is based on radiative transfer theory that includes the attenuation of incoming radiation by scattering and absorption, the scattering of the radiation from all tissues, the propagation of scattered radiation from scattering centers to the detector and RBC and plasma volume fractions. Calculations based on the model successfully predict the optimum values for geometrical and other parameters of the apparatus. Using the parameters given in Table 3 and assumed values for volume fractions, it accounts for the effects described above, and gives their interpretation.

The data in FIG. 10 are interpreted as showing that, when the IE is maximal, the combined volume of RBCs and plasma is maximal. The attenuation by the RBCs increases because the pulse injects RBCs into the irradiated volume. Simultaneous observation of the IE and EE gives two independent measurements, the IE, associated with the combined plasma and RBC volume fractions, and the EE, associated exclusively with the RBC volume fraction. By fitting results for the fingertip capillaries to the model with the two independent volume fractions as parameters, one can obtain a quantitative measure of hematocrit noninvasively.

Simultaneous observation of elastic scattering, fluorescence and inelastic scattering from in vivo near infrared probing of human skin allows discrimination of the movement and presence of RBCs independently from plasma. Careful control of the mechanical force needed to obtain reliable optical registration of in vivo tissue with the optical system allows reproducible observation of blood flow in capillary beds of human volar side fingertips. The time dependence of the elastically scattered light is complementary to that of the combined fluorescence and Raman scattered light. Since fluorescence increases monotonically for increasing hemoglobin and/or plasma volume fractions, this can be interpreted in terms of dynamic volume fractions of the tissues in the irradiated volume with normal homeostatic processes, i.e. heart-driven pulses and the impeding effect of red blood cells on optical propagation to and from the tissue in the irradiated volume.

Example 2

Probing Human Fingertips In Vivo Using Near Infrared Light: Model Calculations

The volar side fingertip capillary beds are probed with near infrared laser light and Raman, Rayleigh and Mie scattered light and fluorescence are collected. The results are interpreted using radiation transfer theory in the single-scattering approximation. The surface topography of the skin is modeled using the Fresnel Equations. The skin is treated as a three-layer material, with a mean-field treatment of tissue composition and related optical properties. The model, with a reasonable choice of tissue parameters, gives a remarkably accurate account of the features of actual measurements. It predicts the optimal values for the incident angle of the laser beam and the distance between beam and detector. It explains the correlated temporal changes in the intensities of elastically (EE) and inelastically (IE) scattered light caused by heart driven pulses, and why they are out of phase. With appropriate boundary conditions, the model can be used to discuss the scattering from ridged skin extruded conformally into an aperture in a metal surface under constant light pressure. The probing results suggest an inherent regularity and similarity in the anatomy and composition of surface and subsurface tissues of a wide range of skin types.

In order to measure blood and tissue analytes noninvasively in vivo, volar side fingertips are probed with near infrared radiation (NIR). The elastically scattered light and the undifferentiated inelastically scattered light, containing both Raman scattered light and fluorescence, are simultaneously measured. Whereas vibrational spectroscopy, specifically Raman scattering with NIR excitation, provides chemically specific and quantitative information concerning molecules in complex mixtures such as blood in vivo, the elastically scattered light, a probe based on physical optics, provides information relating to the presence and disposition of red blood cells (RBCs) in the probed volume.

This Example presents and discusses the present model for analysis and interpretation of the measurements. The model considers the scattering and absorption, inside the skin, of a beam of NIR, and the propagation of the scattered radiation to a detector outside. (It is assumed that the scattering is isotropic, i.e. no preferred scattering angle.) It is used to discuss the effects of skin surface topography, i.e. doming and ridges, as well as the layer structure of skin.

Ridged skin such as is found on volar side fingertips provides an important thermoregulation function and so is highly vascularized, presenting a blood-rich tissue to probe. However, the surface ridges can be commensurate with the diameter of the laser beam, making results depend on the placement of the laser beam on the skin surface. The sample being measured, e.g. the tissue, must be brought into reproducible registration with an optical system. In the apparatus used here, an external servo-driven actuator presses the fingertip against a circular aperture in a thin spring steel sheet and a NIR laser beam penetrates the skin through the exposed surface (Chaiken, et al., 2010, Rev. Sci. Instrum. 81, 034301). The various forms of emitted light are measured simultaneously with a CCD detector.

The blood transmits a local pressure field into the probed volume, the diastolic and systolic pressure, in addition to the local hydrostatic and oncotic pressures. Pressure on the fingertip, even very light constant pressure, has several effects. To the degree that the skin can deform, the pressure causes "doming" or extrusion of tissues into an aperture. Secondly, over time, constant pressure results in movement of fluid, e.g. blood, out of the irradiated region. Also, as fluid moves in response to the applied pressure, the contact area between the tissue and the surface containing the aperture changes, requiring an external servo system to obtain reproducible results.

Regardless of how the subsurface propagation is calculated, the amounts of inelastically scattered light and fluorescence collected are proportional to the intensity of incident light. The Fresnel's Equations are appropriate for calculating the effect of spatial inhomogeneity on light propagation when the path contains features (such as fingerprint ridges) which are large compared with near infrared (NIR) wavelengths. The scattering coefficients account for interactions with interfaces and objects having index of refraction boundaries that are equal to or smaller than the NIR wavelength. Given the well defined anatomy of highly organized skin tissues, in vivo probing encounters a multitude of randomly arranged refractive index boundaries that are properly represented by the tabulated scattering coefficients.

One goal is to construct a model that provides a conceptual framework that accounts for all the experimental observations and if desired could allow a best fit to quantitative measurements by adjusting a small number of parameters. Although it is possible to conceive of detailed models of skin structure with as many as five layers and many parameters, the possibilities for obtaining enough observables to properly test such a model are limited. Zhang suggests that a three-layer model is reasonable in the light of available empirical data, and such a model is used here (Tuchin, 2007, Tissue Optics, SPIE Press, Bellingham Wash., USA). The three layers, designated as a, b, and c from top to bottom, are the stratum corneum and the superficial epidermis, the "capillary bed" that is mostly epidermis but extends inward to the superficial dermal plexus, and the dermis, respectively. Considered first is a planar geometry (in the model layers a and b are defined by parallel planes) and a calculation of the dependence of measured intensities on experimental geometric parameters. Then the effect of extrusion into the aperture of the uppermost layer, i.e. "doming" of the top surface of layer a, is considered. The effect on scattered intensities of known changes like net blood flow into/out of the probed volume is considered. Finally, included is the effect of fingerprint ridges, which are assumed to differ from the effect of subsurface scattering.

The optical properties of the constituents of vascularized skin, i.e. plasma, RBCs, dermis and epidermis have been measured many times, giving mean-field values for the region probed. Jacques has estimated that in the most vascularized "layer", the superficial dermal plexus 200-300 µm below the skin surface, the blood (plasma and RBCs) volume percent is 3-5% (1996, OSA TOPS on Advances in Optical Imaging and Photon Migration, Vol. 2, pp. 364-369, eds. R. R. Alfano, J G Fujimoto, Optical Society of America). Using independently measured scattering and absorption coefficients, one can explicitly calculate only the elastic scattering (EE), but, as one can calculate the path of the incoming light, in principle it is possible to calculate the Raman and fluorescence (IE) produced. To calculate Raman and fluorescence emission in these experiments, the relevant Raman cross-sections, volume percents for all phases giving distinct Raman signals, and quantum yields for fluorescence, are required in addition to the absorption coefficients that are already possessed. In principle these parameters relate the model to chemometric analyses of in vivo Raman spectra and those of turbid media.

Perhaps the most important approximation in the model is the neglect of multiple scattering. Although appreciable fluorescence emanates from all the tissues in the probed volume, the RBCs are the strongest source, followed by the plasma and then the static tissues. An estimate of the volume fraction of blood in the probed volume is 5%. In clinical practice the measured hematocrit (volume fraction of blood which is RBC) depends on the size of the vessel from which the blood is sampled. The hematocrit of blood from a large vessel like the brachial vein is about 45%, but the hematocrit of capillary blood is about 10% or less on average. Using the scattering coefficients tabulated below, one can calculate the scattering length of photons in skin for a range of total blood volumes and hematocrits, with the results shown in FIG. 11. Scattering lengths are almost always much larger than 300 µm. Since the capillary bed itself is only about 200 µm thick, it is clear that a single-scattering model of light propagation should suffice. The scattering length in all the other tissues is even longer than in the capillary bed.

Sufficient detail to allow reproduction of these results has been published elsewhere so the next Section is intended to provide sufficient detail to allow comparison of these modeling results with the practical and experimental facts (Proc. SPIE, Vol. 3918, 135-143 (2000); J. Biomed. Opt. 10, 031111 (2005); Rev. Sci. Instrum. 81, 034301 (2010); Proc. SPIE 6093, 609305 (2006)). Some distinctive experimental observations associated with probing volar side fingertip capillary beds are presented, followed by a presentation of the model. Ultimately the calculated results are compared with the experimental data, in order to demonstrate the validity of this model and the assumptions.

Experimental

The volar side of a fingertip is placed in contact with a rigid flat stiff (0.025" thick spring steel) surface having a ≈2 mm hole, chamfered) (10°) on the side facing the incident light. The incident light is free-space coupled to the skin with a 15 cm focal length plano convex lens. The size of this hole and the chamfering are chosen to minimize extrusion of tissue and to minimize the scattered light produced by interaction of the laser with the edges of the hole. The hole and surrounding surface cause a pressure-dependent stress field within the tissues in direct and indirect contact with the edges of the hole, which leads to motion of subsurface tissues.

Data is obtained using highly polarized, external cavity diode lasers (depending on specific purposes, either Process Instruments, Salt Lake, Utah, USA or Sacher Lasertechnik Tiger Model, Marburg, Germany) with clean-up and edge filters (Semrock, Rochester, N.Y., USA). Data shown below corresponds to 830 nm and 200 mW excitation. Because the laser light is propagated with an angle of incidence of 53±1° (the uncertainty is the practical limit and not a precisely known number) to the normal to the plane of the aperture, the laser cross-section on the finger is observed to be elliptical. Using knife edge scanning experiments and Zap-it paper, it is estimated that the elliptical spot has a 100 µm minor axis and a 237 µm major axis. The spectrograph (Process Instruments, Salt Lake, Utah, USA) is fiber-coupled to a collection train consisting of a custom triplet collection lens, followed by a (Semrock Razor Edge) filter to remove the laser line, and then a refocusing lens. The 59-fiber bundle presents an AR coated circular target to the refocusing lens and a line configuration at the spectrograph entrance slit. The effective slit width is 70 µm and the net collection and spectrograph system is approximately f/2. The wavelength-dispersed light is imaged onto either an Andor DU420-BR-DD CCD camera operating at −65° C. or a Critical Link MityCCD-E3011-BI CCD camera, cooled to −45° C.

In order to view the skin surface through the modulating aperture in real time a 5% reflectance pellicle can be introduced at 45° between the custom triplet and the refocusing lens. Illumination can be provided by a white light source from the collection side. The aperture (finger) can be imaged in real time through the triplet directly and reflected onto a separate NIR enhanced CCD camera. Images were captured using a Snappy™ frame grabber. White light illumination easily saturates the viewing CCD camera. On the other hand, under even low power laser illumination, e.g. 25 mW, the dynamic range of the CCD is challenged in attempting to use the Raleigh/Mie scattered light for spectral probing and imaging. Therefore, judicious use of neutral density filters is required to deal with illumination levels and saturation blooming to obtain good images.

The pressure-induced motion is referred to as "tissue modulation". In order to reproducibly execute these and even static pressure experiments, one must utilize a system that allows accurate and precise placement and pressure maintenance, as described in U.S. Pat. Nos. 6,223,063 and 6,289,230. It is also possible to employ wavelength selective filters to image the skin and thereby deduce perfusion patterns but for the current purposes, scanning the laser across the aperture while simultaneously collecting both the IE and the EE is found to be more useful. For this, the entire assembly containing the aperture is mounted on a stage that can be driven electromechanically relative to the stationary laser and collection system using a Newport NSA12 micropositioner.

In order to understand the behaviors of the IE and the EE the background produced by the specular reflection off the skin surface is examined, which is indistinguishable from the EE scattered background. To characterize how the collection system records specular reflection from the probed skin in the absence of any subsurface or any IE contribution, experiments were performed using stainless steel ball bearings of various diameters in place of the finger in the optical aperture. Some results of experiments using ball bearings that relate directly to the production of highly off-axis light in the collection system has been described, since this can also contribute to the apparent background at all Raman shifts (*Proc. SPIE* 6093, 609805, 2006). The ball bearings must be new and clean, and saturation of the CCD must be avoided, perhaps using an additional laser rejection filter, to avoid measurement artifacts and to prevent damage to the CCD array.

Experimental Results

Measured scattered intensity as a function of wavelength, from a single CCD frame, not corrected for instrument response, is shown in FIG. 9. The regions used to calculate the integrated inelastic signal (IE) and the integrated elastically emitted radiation (EE) are indicated. The EE is dominated by elastically scattered light from all the tissues in the irradiated volume, but also contains light reflected from the skin surface. The inelastic signal includes fluorescence and Raman-scattered light. The IE is necessarily much smaller than the EE.

The optical system is initially aligned so that the light is incident at the middle of the aperture if the sample is flat and in the plane of the aperture as can be seen in FIG. 12A for a thick flat piece of light grey Delrin™. When a finger is registered into the aperture in an unpressed state as in FIG. 12B, the ellipse of contact is slightly shifted to the side of the tissue towards the incoming laser light. If additional pressure is applied the point of contact moves further towards the side of the incoming laser as in FIG. 12C. This motion, as discussed in detail below, is down the side of the extruded dome of tissue. FIG. 12D shows the difference between images B and C, and demonstrates that the total displacement, even for a very hard applied pressure is only 10-30 µm.

In order to probe skin topography, one translates the skin relative to the laser beam, either by moving the finger relative to the aperture with the aperture stationary relative to the excitation and collection optics, or by moving the aperture relative to the excitation and collection optics with the skin stationary relative to the aperture. In the latter case, the amount of off-axis elastic light production depends on the location of the edges of the aperture relative to the laser. FIG. 13 shows data obtained by the former approach. Here a part of the fingertip was scanned where the ridges run perpendicular to the direction of motion, the fingertip being moved through a known distance in a known amount of time with relatively constant applied pressure. The IE and EE integrals shown in FIG. 9 are plotted versus distance translated. Both fluctuate by roughly 20% with a spacing of about 250 µm, characteristic of fingerprint ridges. Interestingly, the spatial fluctuations in the EE integral and the IE integral are complementary: one increases when the other decreases.

Similar out-of-phase oscillations are observed in pulse-modulated time-dependent measurements, in which the pulse causes a periodic increase in RBC volume fraction. Increased volume fraction of RBC necessarily causes an increase in the IE, but this is accompanied by a decrease in the EE. As shown below, although the explanations are different, the temporal fluctuations due to heart pulsing and the spatial fluctuations caused by fingerprint ridges are both predicted by the model. As noted, if the aperture is large enough to include a few fingerprint ridges, extrusion of the fingertip into the aperture, i.e. doming, occurs.

With the present apparatus, a skilled test subject can scan his/her finger across the aperture, with known pressure and acceptable spatial precision and accuracy, using visual feedback from the apparatus. This involvement of the test subject limits the reproducibility, precision and accuracy of the results. Therefore most of the data presented was obtained using the second approach, in which the fingertip moves with the moving aperture. Direct observation through the collection system shows that nearly all test subjects can remain stationary to within ±10 µm relative to the aperture for hundreds of seconds, in spite of inevitable involuntary tremors and similar random motions.

FIG. 14 shows data obtained using the second approach for four test subjects: petite Asian female (28 yrs old), large (6'4" 255 lbs) Caucasian male (19 yrs old), average size Caucasian male (54 yrs old) and average size Middle Eastern male (78 yrs old). In each case, the pressure used to maintain optical registration between the fingertip and the aperture was the average of the diastolic and systolic pressures measured with a commercial automatic blood pressure cuff (Omron). The data consist of 50 consecutive 20 msec CCD frames acquired at fixed positions spaced at 20 □m intervals. A large increase in EE at the extreme right due to reflection as the laser beam strikes the outside of the aperture has been cropped. Oscillations apparently due to fingerprint ridges are evident, but so is a steady decrease or increase in intensity as one goes from left to right. As shown below, this is associated with the "doming" of the fingertip pressed on the aperture. Careful experimentation revealed that for stainless steel ball bearings having curvature similar to fingertips, some reflected light from the bearings propagates through the entrance aperture of the first collection triplet. The smaller the ball, the larger the height of the simulated dome and the smaller the displacement of the aperture needed to scan the reflected light across the entire collection system entrance aperture.

Model Used for Calculations

In the "simple" model a beam of NIR laser light is incident on the top surface of skin at an angle θ' relative to the vertical as shown in FIG. 15, which assumes planar geometry, i.e. smooth skin with no extrusion into the aperture. The apparatus is aligned so that the angle of incidence of the light, i.e. θ', is near Brewster's Angle for an index of refraction for layer a equal to that of water. The actual index of refraction of "tissue" is somewhat higher, but observations reflect modulation of the optical signals due to the motions of subsurface fluids and deformation of static tissues, which do not reflect exactly the anatomical divisions for which individual indices have been measured, i.e. stratum corneum, epidermis, dermis. Thus water is used for reference.

In this case most of the radiation penetrates (because the angle of incidence is constant the transmission coefficient is constant for any point of entry and is close to unity), but light reflected to the detector is not negligible, particularly when the EE is being observed. The amount of light reflected from the skin is estimated as a function of the relative position of the incoming laser and the aperture in a separate calculation. Inside the skin, the radiation is attenuated by scattering and absorption, with the scattering assumed to be spherically symmetrical. This assumption has been used by others and seems reasonable in this case given the known interdigitation of tissues at subsurface layer boundaries with size large compared with the incident and scattered light wavelengths.

Assuming planar geometry, some of the scattered radiation is propagated upward and crosses the flat skin-air interface, where it is refracted, and eventually is collected and detected. The detector is represented as a circular area parallel to the skin surface, with its center, C in FIG. 15, a distance d from the center of the incoming laser beam. The diameter is consistent with the net f-number of the first collection lens. Radiation passing through this "collection circle" from below is considered detected. The amount of radiation entering the collection circle is calculated, given the intensity and direction of incoming radiation and the parameters characterizing the skin. The main assumption made is single scattering, i.e. each photon entering the detector is produced by a single scattering event.

To introduce the effect of "doming" into the model, i.e. the observed extrusion of tissue into the aperture, the planar interface is replaced by a spherical cap. In this case, the incoming or outgoing transmission coefficient depends on the points at which incoming or outgoing radiation enters and leaves the skin. In either planar or dome geometry, radiation passing through this "collection circle" from below is considered detected.

The subsurface skin is modeled as a three-layer planar system. The top layer (layer a, stratum corneum plus the upper nonviable part of epidermis starting at the distal ends of the capillaries) has thickness $t_a$, the middle layer (layer b, epidermis including capillary bed ending with projection of vessel to superficial dermal plexus) has thickness $t_b$, and the third layer (layer c, dermis) is assumed to be infinitely thick. The last assumption is not a source of error because only a small fraction of the collected light comes from layer c, due to the attenuation of both the incident and the scattered light. Typically, $t_a=0.02$ cm and $t_b=0.04$ cm. Three phases are present: r=red blood cells, p=plasma, and t=static tissue. The volume fractions of the three phases in the three layers are denoted by $\phi_{ra}$, $\phi_{pa}$, $\phi_{ta}$, $\phi_{rb}$, etc. Of course, $\phi_{ra}+\phi_{pa}+\phi_{ta}=1$ and so on. The volume fractions used typically in the present calculations are given in Table 1.

Each phase has characteristic absorption and scattering coefficients, denoted by α and μ respectively. Typically, the values shown in Table 2 (first two columns) are used. For present purposes, one can assume that the phases are distributed randomly in each layer. This allows one to calculate an average absorption coefficient and an average scattering coefficient for each layer, and a total attenuation coefficient that is the sum of the absorption and scattering coefficients. For instance, $\alpha_b=\phi_{rb}\alpha_r+\phi_{pb}\alpha_a+\phi_{tb}\alpha_t$ and $\mu_c=\phi_{rc}\mu_r+\phi_{pc}\mu_p+\phi_{tc}\mu_t$.

The incident radiation is assumed to enter the skin from the space above as a beam centered at the origin, O, and making an angle θ' with the normal to the skin layers (FIG. 15). Inside the skin, the angle between the normal and the direction of propagation is θ, where θ is related to the external angle θ' by Snell's law, $\sin(\theta)=\sin(\theta')/n_s$ assuming index of refraction $n_s=1.3$ in the skin. Since all three layers have about the same value of n, the beam is assumed to undergo no further change of direction inside the skin. The transmission coefficient for radiation entering the top layer is calculated from the reflection coefficients for s- and p-polarized radiation, $$R_s = \left[\frac{\cos(\theta') - n_r\cos(\theta)}{\cos(\theta') + n_r\cos(\theta)}\right]^2 \quad R_p = \left[\frac{\cos(\theta) - n_r\cos(\theta')}{\cos(\theta) + n_r\cos(\theta')}\right]^2 \quad [1]$$

The transmission coefficient T is $1-(R_s+R_p)/2$. With $n_r=1.3$ and θ'=0.63, this gives θ=0.47 and T=0.981. The Fresnel equations are used as if the light were unpolarized to attempt to simulate three dimensional variation in the skin surface since to the extent that there is three dimensional tortuosity, both polarizations would contribute to the reflected light and the reflection loss for penetration into the skin. This assumption is made to justify the choice to calculate the trajectory at the interface in two dimensions only. Although the reflected light is only one to two percent of the incident light, its intensity is much greater than the elastically scattered light from plasma and RBCs (see below); it is much smaller than that from static tissue.

As shown in FIG. 16A, the vertical axis is taken as the z-axis, the positive direction being down, i.e. into the skin. The incident beam is in the x-z plane. The direction of propagation of the incident beam in the skin is shown in the Figure by the line OP and its continuation. If B is the x-value of point P, $\sin\theta=B/l$. The angle α is defined as $(\pi/2)-\theta$.

First calculated is the intensity of the beam at each point along its trajectory. If $I_0$ is the beam intensity for z<0 and I is the length of the beam within the skin, the beam intensity at point P is $$I = I_o \exp\left[-\int_0^l (\alpha + \mu)\,dt\right] \quad [2]$$

Here, α+μ is the attenuation coefficient, which depends on $z=t\cos(\theta)$ because α and μ are different in layers a b and c. The probability of scattering by phase x (x=r, p, or t) at the point P is proportional to the scattering coefficient $\mu_x$ and to the volume fraction of phase x in the layer in which point P is located. The scattering probability must be multiplied by the probability that the scattered radiation enters the collection circle, $P_c$.

Since scattering is assumed isotropic, $P_c$ is equal to the ratio of the solid angle subtended by the collection circle to 4π. To calculate this solid angle, note that, in the plane passing through point C and perpendicular to the line PC, the collection circle projects to an ellipse with semi-axes r (in the y-direction) and r/(cos β) (in the direction perpendicular to y), where β is the angle between the line PC and the z-direction (see FIG. 15B). The solid angle subtended by the ellipse is the solid angle sought. Consider a system of polar coordinates with PC being the polar axis, θ the polar angle, and φ the azimuthal angle, and let x' y' and z' be the Cartesian axes with y'≡y and z' along PC. Let ρ be the distance from P to a point on the ellipse so that x'=ρcos φ and y'=ρsin φ. The maximum value of the polar angle is $\tan^{-1}(\rho/c)$. From the equation of the ellipse, $$\frac{(x')^2}{\cos^2\beta} + (y')^2 = r^2$$

one obtains $$\rho = \frac{r}{\sqrt{\frac{\cos^2\varphi}{\cos^2\beta} + \sin^2\varphi}} \quad [3]$$

Thus the solid angle subtended by the ellipse is $$\int_0^{2\pi} d\varphi \int_0^{\tan^{-1}(\rho/c)} \sin\theta\, d\theta = \int_0^{2\pi} d\varphi \left[1 - \frac{1}{\sqrt{1+(\rho/c)^2}}\right]$$

Substituting for ρ and dividing by 4π, the probability that radiation scattered isotropically from point P enters the collection circle is found to be $$P_c = \frac{1}{2} - \frac{c}{\pi} \int_0^{\pi/2} d\varphi \left[c^2 + \frac{r^2}{\frac{\cos^2\varphi}{\cos^2\beta} + \sin^2\varphi}\right]^{-1/2} \quad [4]$$

This factor multiplies the intensity of scattering from the point P.

One must also consider the attenuation of the scattered radiation on its way to the detector. This factor may be written as $$\exp\left[-\int_0^m (\alpha+\mu)\, dt\right]$$

where m is the length of the line PC and α+μ depends on z=t cos β because the attenuation coefficient is different in each layer. Taking all the above into account, the total detected radiation scattered from phase x is written as $$I_{net} = \quad [5]$$
$$I_o T \int_0^\infty dl \exp\left[-\int_0^l dt(\alpha+\mu)\right] \times \mu_x \phi_x(z) \times P_c \times \exp\left[-\int_0^m dt(\alpha+\mu)\right]$$

where z=l cos θ in the first integral overt and z=t cos β in the second integral over t. The integral over l sums contributions from all points along the line OP (extended to a depth so that further contributions are negligible).

The quantity $I_{net}$ represents the scattering from an infinitely narrow beam. To account for the circular cross-section of the beam, calculate $I_{net}$ is calculated for four entry points along the x-direction and average. That is, if d denotes the entry point for the center of the beam, and db the beam diameter (here 0.01 cm), one repeats the calculation for d−0.40451 db, d 0.15451 db, d+0.15451 db, and d+0.40451 db and multiply the four results by 0.13820, 0.31680, 0.31680, and 0.13820 respectively. These are the 4-point Gaussian quadrature points and weights for integrating over a circular area. The sum of the four terms is the scattered intensity averaged over a circle of diameter db.

Predictions of Geometrical Parameters

Calculations using this model were used to establish the optimal values of geometrical parameters of the experimental apparatus. For all calculations, the volume fractions and other parameters given in the Tables are used. One can calculate collected intensities for scattering from each of the three phases and these will be shown. In an actual experiment, one can distinguish between scattering from different phases by Raman shifts and the behavior of the signals under modulation. In any case, the IE is dominated by scattering (fluorescence) from RBCs.

First determined is the optimum angle θ' for a fixed value of d, the distance between the center of the beam and the center of the collection circle. Corresponding to the actual geometry of the apparatus in use, the results presented here are for d=0.014 cm, diameter of the collection circle=0.01 cm, and diameter of the input beam=0.01 cm. The angle θ' is varied between the beam axis and the normal to the outside of the top skin layer and the collected scattered intensities for each of the three phases is calculated, adding together intensities for all three layers.

The results are shown in FIG. 17. From top to bottom, the curves correspond to static tissue, red blood cells, and plasma. For clarity, polynomial fits are drawn (cubic, quadratic, and cubic respectively). The maxima in the three plots, calculated from the data itself, are at θ'=1.192, 0.677, and 0.677 respectively. Since the scattering from static tissue is dominated by the contribution of the top layer, the optimum beam direction is further from the normal. For blood and plasma scattering, a beam direction closer to the normal gives a deeper penetration and more signal, i.e. more of layers b and c, for a fixed distance between beam and detector.

Calculations were conducted in which the value of θ' is fixed and the value of d (distance between the center of the beam and the center of the collection circle) was varied. The detected scattered light originating from static tissue, red blood cells, and plasma were calculated, each the sum of contributions from the three layers.

The value of θ' was fixed at 53.2° or 0.929 radians, which is the value used in the apparatus. (It was determined to be the best choice empirically, and the choice was confirmed by calculations of pressure-modulated intensities using the program, as explained below.) The optimal value of d for tissue scattering is very small, since this scattering is dominated by the contribution of the top layer. From parabolic fits, the optimum value of d for scattering from red blood cells is 0.02030 cm, and that for plasma is 0.02030 cm. Getting more signal from greater depth requires larger values of d for a given angle, since this maximizes the path length in layer b.

Effects of Motion of Subsurface Tissues

In many measurements, one does not obtain the separate contributions of the three phases to the scattering, but only the total intensity, which is dominated by the scattering of the top layer, consisting solely of static tissue. Information about the blood phases is obtained from modulated scattering intensities, i.e. subtracting the intensity measured for a pressed fingertip from the intensity measured for an unpressed fingertip. Pressure forces some blood and plasma out of layers b and c, but has little effect on layer a. Therefore, the modulation or subtraction cancels off much of the large contribution of the static tissue. (However, as discussed below, because of the way pressure is applied in these experiments, the geometry of the skin surface is changed—see FIG. 12—and the cancellation is not complete.) Since the scattering from red blood cells and plasma is of interest, the optimum geometric parameters for modulated scattering is presented.

It is assumed that the pressure removes a fraction f of the plasma and red blood cells in layers b and c, and does not change the static tissue. Layer a is unaffected, but the volume of layer b is decreased and, assuming no change in cross-section, the thickness of layer b is decreased. (Since layer c is infinitely thick, no correction is required.) Considering unit volume, the volume of red blood cells is reduced by $f\phi_{rb}$ and the volume of plasma by $f\phi_{pb}$. The volume is multiplied by $1-f(\phi_{rb}+100_{pb})$, so the new thickness is $t_b \times [1-f(\phi_{rb}+\phi_{pb})]$. Although static tissue is assumed not to be changed by pressure, its scattering will be changed because the screening of the incoming and outgoing light by blood is decreased, so the tissue scattering is not completely canceled off by the modulation or subtraction.

FIG. 18 shows the subtracted intensities plotted against the angle $\theta'$. For these calculations, d was fixed at 0.02 cm and f was 0.1. The curve in the figure is a cubic fit, for clarity. From the data, the optimum value of $\theta'$ is calculated to be 0.9783 radians or 56.5°. This is very close to the value established experimentally earlier, 53°. A series of calculations to establish the optimum value of d for modulated intensities was also conducted. Here, the angle $\theta'$ was fixed at 0.98 radians=56.1° and d was varied. For each value of d, intensities for unpressed and pressed tissue were calculated; these were subtracted to get the modulated intensities. The maximum occurs for d=0.0203 cm. Calculations like those described here were used to establish the optimum angle for modulated scattering, with d fixed at 0.020 cm; an angle close to 53° was predicted.

Another way to cancel out much of the scattering from static tissue is pulse modulation, in which the EE and IE are monitored over time. Each pulse gives an increase and then a decrease in both $\phi_b$ and $\phi_p$, the volume fractions of RBCs and plasma. Since the fluorescence per unit volume is relatively large for the RBCs, the IE increases when $\phi_b$ increases regardless of what happens to $\phi_p$. This leads to only a small change in the EE originating from the RBCs themselves. However, their large scattering coefficient means that RBCs impede propagation of all light in the volume, so that an increase in $\phi_b$ increases the attenuation of the incoming and outgoing beams. Since static tissues have the largest volume fraction, increased $\phi_b$ decreases the total EE, which explains why the IE and EE are found to be out of phase in pulse-modulated measurements. The present model can be used to calculate the effect.

A series of calculations in planar geometry was performed, with $\phi_{rb}+\phi_{pb}$ fixed at 0.008, but $\phi_{rb}$ varying; $\phi_{rc}$ was always equal to $\phi_{rb}/6$ and $\phi_{pc}$ equal to $\phi_{pb}/6$. Note that $\phi_{rb}/(\phi_{rb}+\phi_{pb})$ is the hematocrit in layer b. The results (collected scattering intensity vs. $\phi_{rb}$) are shown in FIG. 19. From top to bottom, the plots are for static tissue, RBCs, and plasma. The scattering from RBCs increase with $\phi_{rb}$, but not linearly, since the scattering attenuates both incoming and outgoing light. The scattering from the other two phases decreases linearly with $\phi_{rb}$. This explains why the IE and the EE change in opposite directions with pulse.

Effect of Changes in Surface Topography: Doming and Ridges

In these measurements, pressure modulation is done by pressing the fingertip against a metal plate in which a circular hole of diameter D has been made, with the incoming laser beam and the detector on the other side of the plate. While pressing the fingertip in this way does remove fluids from the irradiated volume, it also extrudes tissue into the hole, resulting in formation of a dome. This changes the geometry of the experiment, in particular the external angle $\theta'$, which changes the internal angle $\theta$ and, possibly, the path lengths of the incoming and scattered radiation. The resulting change in the detected scattered radiation depends, obviously, on where the beam enters relative to the circumference of the hole. The importance of this "doming" is calculated using the single-scattering model.

Figure 20A:
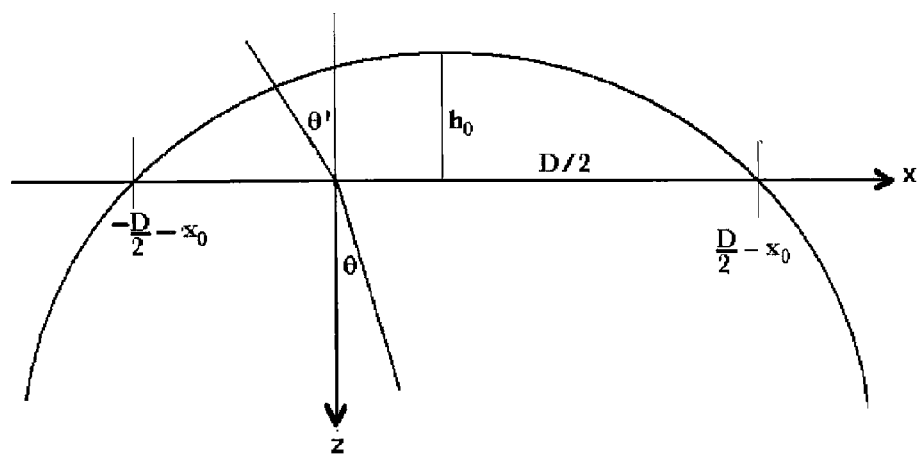

FIG. 20 shows the geometry of the situation in the x-z plane. The x-y plane (x-axis in the 2-dimensional diagram) is the top surface of the skin with no doming, and the z-axis is in the downward direction, into the skin. The circular segment in FIG. 20A represents the dome formed by the fingertip's pressure on the plate; since it is defined by the hole in the plate, it has diameter D. The dome is assumed to be spherical and the maximum height above the x-y plane, at the dome center, is called $h_0$. In the x-z plane, the dome extends from $x=-x_0$ to $x=D-x_0$. The geometrical parameter to be varied is $x_0$, which corresponds to moving the measurement apparatus (laser beam and detector in unison, separated by a distance d) across the hole in the plate.

In the absence of doming, the incoming beam would cross the top surface of the skin (the x-y plane) at the origin, and make an angle $\theta'$ with the external normal (negative z-axis), as shown in the diagram. The angle it makes with the internal normal would be $\theta$. Clearly, the angle the incoming beam makes with the external normal to the dome differs from $\theta'$ (in FIG. 20A, it is very close to 0), so its direction inside the skin differs from $\theta$; the difference is greater, the farther one gets from the center of the dome.

The radius of the dome, $R_m$, is first calculated in terms of D and $h_0$. Considering the continuation of $h_0$ to the center of the circle (sphere) of the dome, and a line from the center to the point $x=D/2-x_0$, gives $$R_m = \left(h_0^2 + \frac{D^2}{4}\right)(2h_0)^{-1}$$

The equation of the circle is $$\left(x - \frac{D}{2} + x_0\right)^2 + (z - R_m + h_0)^2 = R_m^2$$

Combining this with the equation for the incoming beam, $x=z \tan \theta'$, gives the coordinates of the intersection point, and the slope of the outward normal to the circle (spherical surface) at that point. Then one can calculate the angle the incoming beam makes with this normal and, using the Snell's-law equation, $\theta$ is obtained, the angle between the refracted beam inside the skin and the normal, as well as the transmission coefficient at the skin surface.

Figure 20B:
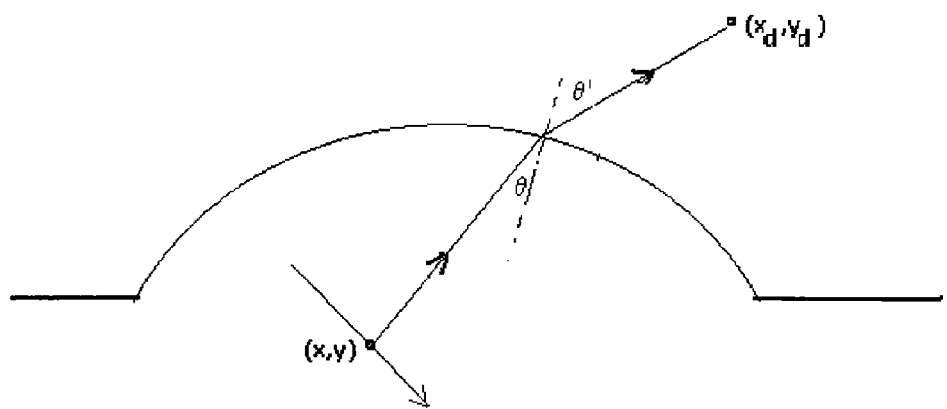

Then, as previously, scattered intensity from every point along the trajectory of the beam in the skin is considered. The intensity of scattering is proportional to the intensity of the beam, attenuated according to the path length from the entry point to the point of scattering. In FIG. 20B, (x,y) is a point along the beam trajectory and $(x_d, y_d)$ is the center of the detector. The normal to the sphere at the point where the scattered radiation crosses it is shown as a dashed line. The path the scattered radiation takes to the detector is also altered because of the dome geometry, since refraction occurs at the skin surface (angles θ and θ' relative to the normal to the surface). The point of intersection of the scattered beam with the surface must be calculated so that θ and θ' obey Snell's Law, and the transmission coefficient for the beam leaving the skin must be calculated.

Calculations of detected intensity were performed with D=0.200 cm, $h_0$=0.01 cm (100μ), d=0.020 cm, and θ'=0.980. (angle of incoming beam relative to z-axis). The values of D and $h_0$ are typical for the present experimental apparatus and a finger with an unpressed diameter of 1 cm. The beam source and the detector were assumed to be at 0.013 cm above the z=0 plane, with the center of the detector at $x_d$ and the center of the source beam at $x_s$ where $x_d-x_s$=0.022 cm. The range of meaningful $x_s$ values is from −0.12 to +0.08; the geometry makes $x_0$ (coordinate of the intersection of the beam center with the skin) greater by about 0.02. For $x_0 \cong$ D/2, 0, and D/2=0.100, the angles the beam inside the skin makes with the z-axis are 0.819, 0.771, and 0.706 respectively; the corresponding transmission coefficients are 0.981, 0.976, and 0.963. For $x_0$ approaching −D/2 or +D/2, one has to correct for the masking of the beam or the detector by the plate, since one or the other passes outside the aperture. Because of the non-zero widths of both the detector and the beam, the masking is gradual at each end. The contribution of reflected light from the aperture to either total EE or IE signal is discussed later.

FIG. 21 shows how the calculated EE scattering intensities from static tissue (panel A), red blood cells (panel B), and plasma (panel C) change with $x_s$. Note that increasing $x_s$ corresponds to moving the aperture from right to left, or to moving the incoming beam and the detector from left to right, with the distance between the two fixed at 0.022 cm. The masking of the beam is responsible for the drop of intensities to zero for $x_s \sim$−0.12 and the masking of the detector is responsible for the drop for $x_s \sim$+0.08.

Interestingly, the calculated EE intensity from static tissue first decreases (by almost 20%) as $x_s$ increases until just before the centerline and then increases to slightly less than the original value at the other side of the aperture. In contrast the intensities from red blood cells and from plasma both go through maxima (each by about 10% total), as $x_s$ increases. Although the parameters used in the calculation are for the propagation and production of EE, this is exactly what is seen in the experimental results of FIG. 14 for the IE. Since these calculations deal with the tissue optics of the probing, any light that is produced in the same location as EE will have the same scanning behavior as EE. The opposite behaviors of scattering intensity from static tissue, which contributes to IE, and scattering intensity from blood, which contributes to EE, are also seen in FIG. 13. Here, the small intensity oscillations may be due to fingertip ridges, as discussed in more detail below; but their origin is the change in the incident angle of the beam.

Although the parameters associated with the production of EE are very different from those for the production of IE, the total IE production is dominated by the static tissue because of its dominant, >95%, volume fraction in any layer. In this connection, the preceding Example has shown how the well-known "autofluorescence" of static tissue can be bleached by the excitation laser; this effect can be seen in the results in FIG. 14. The IE decays with time at each of the scan locations unlike with the EE. Thus the calculated variation in production of EE reveals the location of the exciting light, which is available to be absorbed by whatever species cause the autofluorescence in static tissues thereby also accounting for variation in the production of IE.

Unlike the measured IE, the measured EE contains a significant direct contribution from the light reflected specularly from the skin surface. The results of the calculations for the reflection from 1 cm diameter skin are shown in FIG. 21, panel A, as empty squares. (The intensities are zero for $x_s$>−0.03 because the reflected light can not enter the detector.) When added to the calculated EE, they produce the points labeled with x's in FIG. 21A. Visually scaled and offset, the results with and without the reflectance contribution are also shown as thick black lines in the EE and IE results in FIG. 14 respectively.

The actual shape of the dome relates to the size and turgor of the fingertip. Variation in the dome height, and non-spherical dome shapes, consistent with a reasonable amount of turgor, shift, shape and modulate the intensity of the specular contribution, accounting for the variation observed between individuals in FIG. 14. This can be seen in the decrease in EE as the displacement increases above $x_s$=0, i.e. 800 microns, compared to the calculations which show a decrease after $x_s$=0.8, i.e. 1500 microns. In actual fingertips, the height decreases to zero more rapidly, approaching the aperture edge, than in a spherical cap. Also, the reflected light from the aperture itself (with associated chamfer since the aperture is not infinitely thin) seen in the Delrin EE, also contributes to the excess IE observed in vivo. Note that in general the net IE signal is only ≈10% of the EE signal and this excess fluorescence is much smaller for the Delrin which has dome height 0 so it cannot be easily seen in FIG. 14. This is considered an indirect effect of specularly reflected light.

It should be emphasized that the change in scattered intensity with $x_s$ (10-30%, see FIG. 14) is much larger than the change in transmission coefficient (2%). This confirms that the effect is mostly due to the changed beam direction inside the skin, which is shown to lead to very large changes in scattered intensity. Of course, a small change in transmission coefficient near unity implies a large relative change in reflection coefficient, so that the specularly reflected light makes a substantial contribution to the observed EE. The different behaviors of static tissue scattering and blood scattering arise because the former dominates the top layer, which does not contribute to the blood scattering. These observations are the basis for the present discussion of the effect of fingertip ridges.

For a planar surface, the angle of incidence does not change with the placement of the beam. For a dome, it varies systematically with the position of the beam entry point. The actual surface of the skin is neither flat nor a dome because of the fingerprint ridges, which have a spacing of about 600μ. Since the beam diameter is of the order 200 μm the beam could illuminate mostly one ridge top, or straddle a ridge top and bottom. If the beam is incident near a ridge boundary, the angle of incidence of some of the incoming photons will be much larger or smaller than 53°, and the scattering intensity can change significantly with a small change in the incident angle. Thus, moving the aperture across the fingertip produces not only a monotonic variation of intensity due to doming, but also oscillations commensurate with the spacing of the fingerprint ridges.

Figure 22:
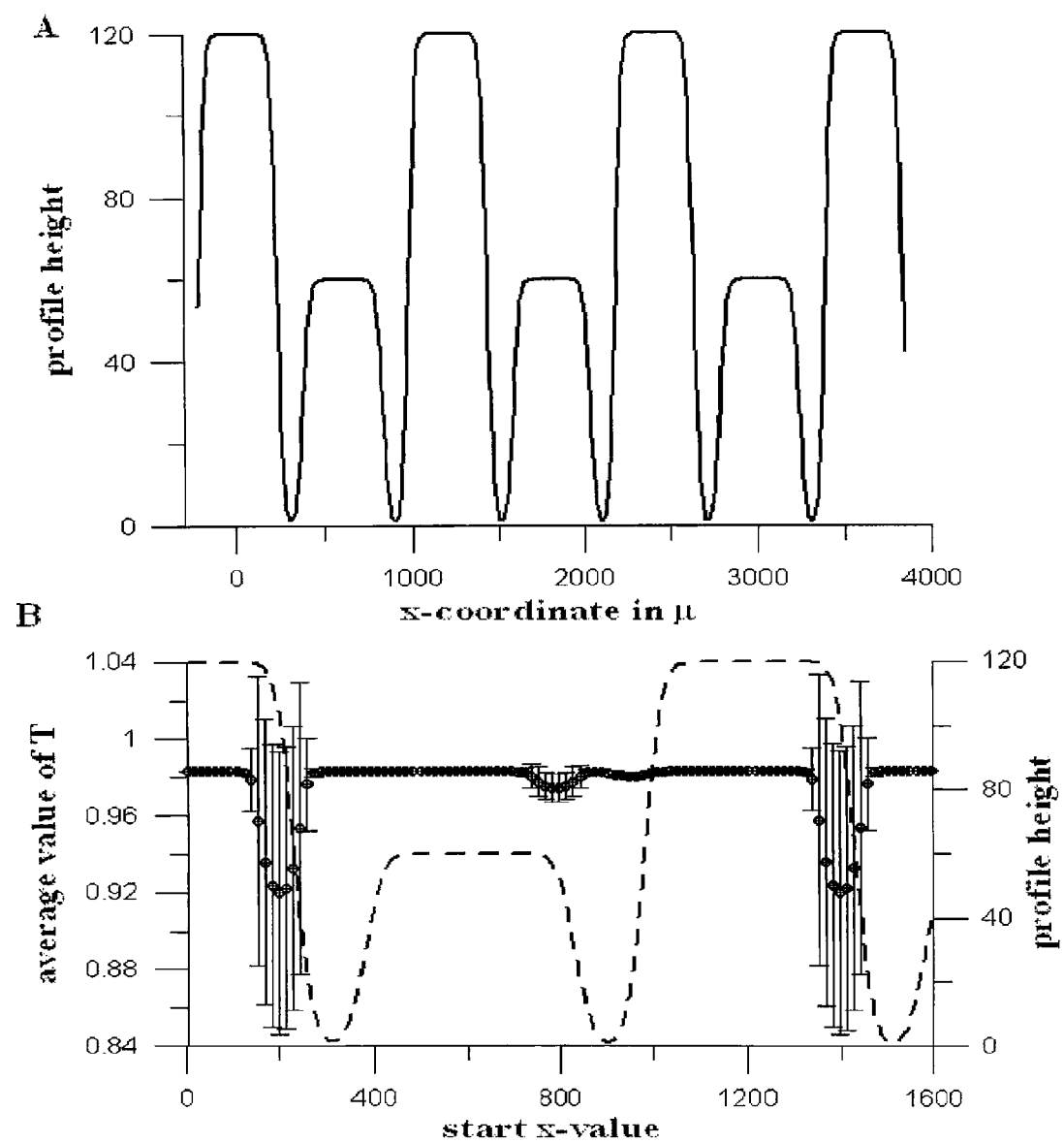

The profile shown in panel A of FIG. 22 is used to discuss this effect. The ridges are assumed to have a spacing of 600 μm; alternate ridges are assumed to have heights of 120 μm and 60 μm (the alternation in height is an observed feature of actual fingerprint ridges). Each ridge is represented by the double-Gaussian function $$y = \frac{h}{4}\left[1 + \text{erf}\left(\frac{x - x_0 + \frac{w}{2}}{s\sqrt{2}}\right)\right]\left[1 - \text{erf}\left(\frac{x - x_0 - \frac{w}{2}}{s\sqrt{2}}\right)\right]$$

where h is 120 μm or 60 μm, $x_0$ is the center (=7 μm, 607 μm, 1207 μm, etc.), w is the width (450 μm), and s is the shape parameter, equal to 30 μm. The values of the parameters are chosen to give the ridges and the valleys between them a shape close to what is actually observed. Starting at equally spaced values of x (−222 μm, −207 μm, −192 μm, etc.), and height 164 μm, the trajectory of the incoming ray is calculated at 53° to the vertical and where it intersects the profile and the angle θ' it makes with the external normal to the profile at the point of intersection is determined. From θ' one obtains θ and calculates the transmission coefficient T, using [1].

Calculated transmittance (T) varies wildly as the entry point passes through a valley between ridges. Such large variations would be observed for infinitely narrow beams, but the beam has a width of 100 μm. Panel B shows the weighted average of transmittance over 7 points (symbol ⊕) and the population standard deviation (vertical bars), plotted against starting x-position. (Because the beam starts from above and is directed at 53° from the vertical, the x-value of the entry point of the center of the beam is about 50 μ to the right of the start value of x, the offset being different for different $x_{start}$.) The profile is shown as a dashed line in panel B. The averaging reduces the variation in transmittance to a few percent but a small variation in transmittance is associated with a large variation in detected scattered intensity.

These calculated results explain what is observed in the IE and EE plots obtained by intentionally translating the fingertip while collecting CCD frames (FIG. 13). The IE and EE plots are complementary because the optimum angle of incidence is different for radiation scattered from static tissue, dominated by layer a, and for radiation scattered by blood, found only in layers b and c. If one layer produces greater IE per unit volume than another, passing through the angle that optimizes signal from that layer will produce an increase in the observed. IE. The layer thicknesses were chosen to reflect the fact that the blood is mostly localized in a region between two others that barely contribute to the modulated signal when blood moves.

The possibility that the oscillations in FIG. 13 are due to the variation in reflectance accompanying the variation in T was considered. Using clean stainless steel ball bearings of different diameters to represent surfaces of different curvatures, the effect on IE and EE of reflection from metal surfaces of various curvatures was measured. The IE result is a small featureless baseline shift over the entire collected spectrum. There is also an "inelastic" artifact because very highly off-axis light can be generated using a ball bearing with very small radius of curvature and such highly anti-parallel off-axis light can be dispersed in the spectrograph across the entire CCD surface. However, opposite to what is observed in FIG. 13, the purely reflective elastic and "inelastic" artifacts are in the same direction, i.e. collected light of both kinds is reduced.

Discussion

A series of calculations has been performed to help understand and represent (1) how incident and scattered light propagate in skin during an actual experiment and (2) how the IE and EE signals from the irradiated volume are affected by the measurement procedure. Even if one does not intend to perform a modulation experiment, the measurement process involves pressing the fingertip against an aperture in order to obtain reproducible registration with respect to the optical system, and the anatomical and physiological characteristics of skin in vivo require consideration of the effect of movement of subsurface materials, i.e. blood, on the measured signals.

The situation in which ridged skin is probed by free-space coupled light has been discussed, but many of the results are also relevant to experiments in which the incident light is coupled to a skin surface with different topography, e.g forearm, using optical fiber. Although there might be no doming effect in this case, bringing fiber into registration with the skin surface inevitably indents the tissue with a concomitant movement of subsurface tissues. Also, all tissues have spatial texture on the scale of optical fiber diameters. Probing the nailbed vascular system that is accessible through the fingernail, as is done in commercial pulse oximetry, removes some soft tissue effects, but any pressure on the nail itself relative to the bone inside causes motion of subsurface tissues.

With the assumptions and approximations of the model, optimal values of the geometrical parameters of the instrument have been predicted, i.e. incident angle and distance between the point of contact of the incident light with the skin surface and the collection circle. In fact the signal was optimized using a procedure presented in detail elsewhere, and the exact values of these and other parameters are close to those produced by the model. Probably, for best results, one should employ a real-time optical servo system to maintain certain optical metrics during the measurement process, as already done to maintain mechanical consistency. Overall, the fact that reasonable values are calculated for the geometrical characteristics of the observed signals lends credibility to the entire modeling process The present model allows us to understand the effects of pressure modulation and ridged skin on the scattered intensity. The path of the laser light transmitted into the probed tissue is distorted by the surface topography, changing the angle of incidence and thereby the depth probed for a given experimental geometry. In an earlier small clinical study of non-invasive glucose measurement in vivo using combined fluorescence and Raman spectroscopy relation of prediction errors to the measurement process was attempted. Production of fluorescence is much more efficient than production of Raman-scattered light and so reflects the conditions from a greater depth. Rayleigh/Mie scattered light originates from as deep as 2 millimeters per calculations, so observed fluorescence may actually approach that depth. Since fluorescence enters the algorithm for calculating glucose concentrations, the present study suggests that some of the prediction error may be associated with variation in the location of the incident laser relative to the fingerprint ridges. The results in FIGS. 13 and 14 suggest a way to perform finger placement so as to achieve reproducible ridge placement with respect to the optical aperture and the incident laser.

Presented here is a first principles-based model that is true to the experimental realities as well as the anatomy and physiology of the tissue. The skin is modeled as three-layer and the requisite three phases are present: red blood cells, plasma, and static tissue, with the first two absent from the top layer. Values from the literature are used for the scattering and absorption coefficients and the volume fractions of the three phases. It is assumed that the phases are distributed randomly in the second and third layers, allowing calculation of average scattering and absorption coefficients of these layers. These determine the attenuation of incoming and scattered radiation, as well as the scattering probability at each point. By following the path of the light from the source outside the skin to the detector, one can calculate the intensity of detected radiation coming from each of the three phases (Equation 5). The expression involves an integration over all points along the beam from which scattering may occur. To take into account that the laser beam is not infinitely thin, the average is taken over an appropriate circular cross-section.

The calculations show that only a very small fraction of the collected light comes from layer c, due to the attenuation of both the incident and the scattered light. Because the production of wavelength-shifted light (IE) and the production of elastically produced light (EE) depend differently on the phases, the different behaviors of the actual observed IE and EE are reproduced. The optimum beam angle for EE from static tissue is much larger than for blood phases because the scattering from static tissue is dominated by the contribution of the top layer, which contains neither RBCs nor plasma. For blood and plasma scattering, a penetration into layers b and c is required; for a fixed distance between beam and detector, this means a beam direction closer to the normal. Correspondingly, to observe more signal from greater depth requires larger values of d for a given angle, since this maximizes the path length in layer b.

These experiments do not measure the separate contributions of the three phases to the scattering, but obtain only the total intensity, which is dominated by the scattering of static tissue. To get information about the blood phases, tissue modulation is employed, i.e. subtract the measured total scattering intensity of a pressed fingertip from that of an unpressed fingertip. Since pressure forces some blood and plasma out of layers b and c, but has little or no effect on layer a (as shown in FIG. 12), the modulation or subtraction cancels off much of the large contribution of the static tissue. Therefore, the optimum detector displacement is established for the modulated scattering, obtaining a value very close to the value found experimentally earlier, i.e. ≈53°, giving us confidence in the model used (the optical system cannot be aligned with greater precision than ≈2 degrees).

Attempt was made to cancel off the scattering from static tissue by pulse modulation, since a pulse changes the volume fractions of RBCs and a "pulse modulated" Raman spectrum of blood has been published. Since the modulated IE is dominated by the contribution of RBCs, the inelastic scattering integral increases when RBC volume fraction increases allowing us to use the integrated IE to select CCD frames of high RBC content and another equal set with low integrated fluorescence, i.e. IE, to subtract from each other. Using the IE to normalize these spectra as in previous studies, preliminary experiments show a correlation exists between glucose concentrations obtained from these spectra and externally measured finger stick blood glucose levels.

Most of the results show that elastic scattering intensities vary linearly with the various perturbations considered. A potentially important exception was found in a series of calculations in planar geometry, with $\phi_{rb}+\phi_{pb}$ fixed at 0.008, but $\phi_{rb}$ varying; $\phi_{rc}$ was always equal to $\phi_{rb}/6$ and $\phi_{pc}$ equal to $\phi_{pb}/6$. As expected and as shown in FIG. 12, the scattering from RBCs increases with $\phi_{rb}$, and the scattering from the other two phases decreases linearly with $\phi_{rb}$. But the increase in scattering from RBCs is not a linear function of $\phi_{rb}$ because the elastic scattering by RBCs attenuates the scattered (outgoing) light, including that from the RBCs. These results explain why the observed inelastic and the elastic scattering integrals, IE and EE, change in opposite directions with the pulse.

In most experiments, there is not a planar geometry because pressure applied to the fingertip for registration causes skin to extrude into the aperture, forming a dome. When the fingertip and the hole are moved relative to the laser beam and the detector, the scattering integrals IE and EE vary because in the non-planar geometry the angle of incidence varies. When only the fingertip is moved, the point of incidence is at the same point of the dome, as long as the applied pressure is constant, and the angle of incidence is constant. However, there are oscillations corresponding to the fingerprint ridges (FIG. 13), with the inelastic and elastic scattering integrals changing in opposite directions. Calculations based on the model explain these effects.

In planar symmetry, the angle θ' between the incoming beam and the external normal to the skin is independent of the point of entry of the beam. With a dome, the angle θ' depends on the point of entry. The angle between the incoming beam and the external normal to the dome is calculated as a function of the position of the entry point of the beam and, using Snell's Law, the angle between the refracted beam inside the skin and the internal normal, as well as the transmission coefficient at the skin surface. The transmission coefficient varies very little with the point of entry, but the variation in the reflection coefficient, itself about 0.02, is important because reflected radiation may contribute to the collected elastic scattering. The variation in detected scattered light intensity, however, is most important.

FIG. 21 shows how the calculated elastic scattering intensities from static tissue, RBCs, and plasma change with beam entry position $x_0$ when the skin is stationary with respect to the aperture. The same calculated results are superimposed on the observed variations of intensities in FIG. 14 and are very well reproduced, especially when the direct and indirect effects of all the specularly reflected light are included. The (actual) intensity from static tissue decreases (by about 30%) and then increases with $x_0$, while the intensities from red blood cells and from plasma increase (by about 10%). The observed total EE intensity, dominated by the scattering from static tissue, decreases in the scanned direction faster than calculated, consistent with the notion that for a given dome height, the dome edges approach the edges of the aperture faster than would a spherical cap. The IE is characterized by very different scattering parameters from the EE, which compensates to some extent for the very different volume percentages of the phases. Nevertheless, the IE yield in FIG. 14 is close to that predicted for the EE suggesting that the IE from the plasma and RBCs is small compared to that from the static tissues. This is consistent with the observed net modulation of the time dependent IE signal with the cardiac driven pulse, ≈5-10%.

Opposite variations in scattering intensity from static tissue, which dominates IE, and scattering intensity from blood, which dominates EE, are also seen in FIG. 13. In this case, the intensity oscillations are due to the changing incident angle of the beam as it passes across fingertip ridges. Since the spacing of the fingerprint ridges is about 600 μm, and the beam diameter is only 200 μm, the beam illuminates only a portion of a ridge, and the incident angle depends strongly on where on the ridge the beam impinges. The oscillations are in opposite directions because, as shown in FIG. 17, the optimum incident angles for static tissue and for blood are very different.

One need calculate only transmission coefficients for ridges, since the calculations for domed skin show that a small (2%) change in transmission coefficient is associated with a large (10-30%) change in scattered intensity. However, the observed variation is even greater, showing that more than one factor is in effect. By adjusting the parameters defining the surface geometry to get best fit to experimental results, one could gain information about skin surface topography. In the best case, a digital representation of the skin surface could be obtained by deconvolution of experimentally measured scattering intensity profiles.

The model shows the difference between the IE data obtained by moving the finger relative to the stationary aperture and optical system, and the data obtained by scanning the aperture and the finger together across the optical system. The former, FIG. 13, corresponds to scanning a subsurface probe at constant depth whereas in FIG. 14 the dome is probed at variable depth as the aperture is scanned across the optical system or, equivalently, the optical system scanned across the dome. Even with enough pressure to produce easily observed doming, the photographic study (FIG. 12) shows that the entry point of the laser moves less than ≈20 □m. The major axis of the elliptical spot is much wider than the motion of the spot induced by the increased dome height. The laser power for obtaining FIG. 12 was much reduced to obtain images with a minimum of CCD blooming. Thus the model supports the idea that in a modulated experiment a nearly identical volume is probed for the pressed and unpressed states. According to FIG. 23 the signal collected during the unpressed measurement originates from deeper tissues. Because these are richer in blood than the more superficial tissues, the tissue-modulated, i.e. unpressed minus pressed spectrum, is enriched in Raman features originating with blood as originally claimed.

This can be seen more clearly by reference to FIG. 14 in the light of FIG. 21. During the unpressed phase of a tissue modulation cycle, the incident laser impinges on the skin surface near point "U" as marked on the IE graph. This is slightly to the side of the aperture center, indicated with "C", due to the slight doming caused by the small pressure used for registration. Applying more pressure has two effects. First, the doming increases and the point of contact of the laser moves farther from the centerline in the direction of the point labeled "P". This decreases the IE and decreases the contribution of the static tissue to the net observed EE. Second, if a subsurface fluid, e.g. blood moves out of the irradiated volume, the IE decreases even more.

The tissue-modulated spectrum obtained by subtracting the pressed from the unpressed spectrum therefore is enriched in Raman features and fluorescence originating from blood, in agreement with earlier observations of correlation between the modulated Raman spectra and blood glucose levels measured independently. Based on FIG. 12, the separation of the lines indicated by U and P are greatly exaggerated in FIG. 14 and in reality they are >95% superimposed on each other.

Although there are certainly other sources of variation in glucose concentrations calculated from in vivo Raman spectroscopy of volar side fingertip capillaries, this study shows that one source is variation in the form of the dome, which could be mitigated by careful control of the measurement process. The calculations of FIG. 11 demonstrate that a single-scattering model should represent all qualitative aspects of probing real tissue in vivo by NIR radiation well. This was found to be true and, with proper choice of the parameters, one could achieve quantitative agreement with observations. The radiation transfer approach is rigorous and very flexible and, since single scattering is assumed, requires only seconds, much less than multiple scattering models.

Shown here is that tissue modulation should produce spectral features originating with subsurface blood in the capillary network, making it possible to measure glucose and other blood analytes non-invasively using Raman spectroscopy. This approach has evolved so that, in addition to considering essential human factors of the measurement process, it strives to at least partially mitigate the effect of turbidity and inter-subject skin differences, by managing RBC content and movement across test subjects and for one test subject across time.

Published data is available from two other Raman studies of noninvasive in vivo glucose measurement (Barman, et al., 2009, *Anal. Chem.* 81, 4233-4240; Lipson, et al., 2009, J. Diabetes Sci. and Technol. 3, 233). It may be possible to further correct for turbidity effects using a data pretreatment based on an analytical treatment of multiple scattering effects. The proposed pretreatment would incorporate information from a reflectance spectrum, perhaps acquired simultaneously with the Raman data, to provide improved calibration across individuals. All of these measures must be explored to finally succeed in producing commercially viable devices that can meet the immense need for continuous noninvasive in vivo blood and tissue analysis.

The model presented herein for transmission and scattering of a laser beam through three layers of skin is able to interpret all of the experimental observations. The model allows determination of the optimal configuration of laser beam and detector for collecting scattering from static tissue and blood phases. It can take into account the effect of pressure-induced deviations from a flat skin surface. It explains the origin of the alternation between IE and EE observed in both temporally modulated and spatially modulated experiments. The ability of this model to predict all of these aspects of the measurement process suggests that a single-scattering, isotropic model is adequate to describe the information derived from probing of skin using NIR radiation. Since the fingertip skin is highly vascularized and RBCs have by far the largest scattering coefficients of all the tissues involved, the single-scattering isotropic model should also suffice for modeling the probing of other skin locations with lower blood content, such as forearms. By affording an accurate interpretation of experimental observations as well as measurement artifacts, this model provides a firm theoretical basis for using the measured spectra of scattered light to determine, noninvasively and in vivo, blood properties like glucose concentration and hematocrit, as well as skin properties like turgor.

Example 3

Direct Noninvasive Observation of Near Infrared Photobleaching of Autofluorescence in Human Volar Side Fingertips In Vivo Human transdermal in vivo spectroscopic applications for tissue analysis involving near infrared (NIR) light often must contend with broadband NIR fluorescence that, depending on what kind of spectroscopy is being employed, can degrade signal to noise ratios and dynamic range. Such NIR fluorescence, i.e. "autofluorescence" is well known to originate in blood tissues and various other endogenous materials associated with the static tissues. Results of recent experiments on human volar side fingertips in vivo are beginning to provide a relative ordering of the contributions from various sources. Preliminary results involving the variation in the bleaching effect across different individuals suggest that for 830 nm excitation well over half of the total fluorescence comes from the static tissues and remainder originates with the blood tissues, i.e. the plasma and the hematocrit. Of the NIR fluorescence associated with the static tissue, over half originates with products of well-known post-enzymatic glycation reactions, i.e. Maillard chemistry, in the skin involving glucose and other carbohydrates and skin proteins like collagen and cytosol proteins.

Noninvasive in vivo tissue and blood analysis is a long-standing goal of the biomedical spectroscopy community. The work here is primarily focused on the use of near infrared (NIR) spontaneous Raman and fluorescence spectroscopy to monitor blood analytes including glucose. The presence of ubiquitous NIR fluorescence is well-known although poorly understood despite the fact that it is a more or less serious impediment to most approaches to NIR noninvasive in vivo tissue and blood analysis. This Example describes recent work directed at clarifying the origin and nature of such fluorescence. The technological ramifications of this knowledge may be important with respect to noninvasive blood glucose monitoring using NIR Raman spectroscopy.

Although fluorescence in the UV-visible is extremely well characterized for a vast multitude of chemical species that are found in vivo, there is far less known about emission excited by NIR absorption. But for in vivo applications the NIR is the only relevant spectral range because light must first traverse at least 200-300 μm of non-vascularized tissue to obtain vibrational spectra of blood noninvasively in subcutaneous tissue in vivo. The scattering and absorption coefficients of all relevant tissues are well known and are most favorable in the NIR spectral region, and the propagation of light can be treated in the single scattering limit due to the relatively low volume percent of red blood cells, i.e. hematocrit in capillaries. So although the propagation of NIR light in vivo can be described reasonably well and in detail, the production of fluorescence cannot.

In earlier work with noninvasive glucose determination, fluorescence was used as a measure of the probed volume generally and, in a modulated approach, the blood volume that should be used to calculate the concentration of a substance based on the strength of a particular Raman feature (U.S. Pat. Nos. 6,223,063 and 6,289,230). The so-called "autofluorescence" has a broad emission spectrum that is believed to have no peak at least to 925 nm. Based on the response of the emission to temperature and mechanical pressure tissue modulation, every volume fraction of the irradiated volume i.e. static tissue, red blood cells and plasma produces emission. Interstitial volume and associated fluids are included with "static tissue" because these materials deform spatially but do not translate appreciably with application of external pressure.

From a chemical substance point of view a significant amount of fluorescence can be associated with hemoglobin and other endogenous and exogenous porphyrins as porphyrins are well known to produce copious fluorescence under NIR excitation. For example cytochrome species that are found exclusively in the static tissue are fluorescent but they exist in very small quantities relative to the other porphyrins and so are probably a minor contributor to the net porphyrin based emission. Bacteria are known to produce porphyrins on the skin that for a given test subject could be significant. In fact there are probably a number of minor contributors, porphyrins and non-porphyrin, and this makes a complete description of the net fluorescence more difficult. From the experimental side one difficulty in attempting to associate a specific amount of fluorescence with a particular volume of tissue in vivo is that the sample is perfused and so cannot be studied in the absence of blood, the single largest contributor to the net fluorescence on a per unit volume basis. Moreover the blood content is dynamic and easily perturbed without special apparatus and procedures.

First some in vivo results on volar side fingertips are presented that demonstrate the presence and nature of the fluorescence and demonstrate the photobleaching of that fluorescence by the NIR excitation itself. Later, results are presented from in vitro experiments that narrow the list of possible in vivo NIR fluorophores and also provide a basis for some of the observed photobleaching behavior in vivo.

Experimental

A schematic diagram of the instrumentation, i.e. a LighTouch™ measurement device, is shown in FIG. 23. Incident light 10 emitted by the laser 12 passes through a clean-up filter 14 and plano-convex focusing lens 16 through an aperture in a steel sheet 18 against which the fingertip 20 to be probed is positioned. Collected light 22 passes through a compound collection lens 24, "razor edge" filter 26, and a refocusing lens 28, to a fiber optic bundle 30 that leads to the spectrograph 32. Not shown are a set of two electronic shutters (Vincent Associates) that are inserted between the clean up filter 14 (Semrock) and the input coupling lens 16 allowing application of various pulse sequences to the fingertip 20 using the CW external cavity diode laser 12 (either Sacher or Process Instruments). The collected light 22 is imaged using a nominally f/2.1 spectrograph 32 onto a (Critical Link or Andor) CCD camera. For in vitro samples a fused silica cuvette is employed for liquid samples and the light is detected by a Roper Scientific/PAR CCD camera after dispersion by a Kaiser f/1.4 Holospec spectrograph.

For in vivo probing of fingertips 20 the optical aperture is machined into a spring steel sheet 18 so that the movement of the aperture is less than 25 μm even for the largest applied pressures, i.e. force. The finger is reproducibly positioned relative to the optical aperture and at a well-defined pressure using a specially configured load cell (Omega LCKD) and a set of conductive gold spots. The 34 spots are placed in a pattern relative to the optical aperture such that when skin makes simultaneous contact with a set of dots and a thin gold annulus enclosing the optical aperture, the decrease in electrical resistance allows the software to estimate the total contact area between the skin and the spring steel surface. Knowing the contact area and the total applied force one can calculate the applied pressure. Because it is not possible to insure mechanically stable placement without the skin contacting the material around the aperture, i.e. the spring steel, and any pressure causes movement of the subcutaneous blood, it is necessary to know the applied pressure and to reference it to the independently measured blood pressure in order to obtain consistent results across test subjects and even to obtain consistent results for a particular test subject at different times.

For the in vitro studies of blood, RBCs were lysed in deionized water, and the resulting aqueous hemoglobin solution was filtered prior to dilution. The concentration of hemoglobin was determined using a HemoCue Hb monitor. The free base lysine used for producing the early Maillard products contains a fluorescent impurity as provided by the supplier (Sigma-Aldrich) that should be removed prior to experimentation although the ribose and arginine were used as received. Commercial melanin (Sigma-Aldrich) was first allowed to dissolve in water before being filtered in a 200 nm Whatman syringe filter.

Results

A typical raw 20 ms CCD frame from a fingertip (200 mW, 830 nm excitation, no instrumentation function correction applied) is shown in FIG. 9. The applied pressure is the average of the diastolic and systolic pressures, in this case ≈60 g/cm². The integrated fluorescence and Raman emission is referred to as inelastic emission, i.e. IE, and the Rayleigh line as elastic emission, EE. The amide I, $CH_2$ deformation, and amide III modes are clearly visible at ≈1660, ≈1450 and ≈1270 cm$^{-1}$ respectively as is the underlying broadband fluorescence. A series of experiments were performed to test the dynamic behavior of the fluorescence because subcutaneous materials that may move spatially may have different characteristics than that originating from stationary sources.

The IE and EE integrals for each frame are shown in FIG. 9 as BV and RBC respectively because the IE contains the dynamic fluorescence of the plasma and the RBCs in addition to a component from the static tissue whereas the EE signal has been shown to decrease as RBC volume percent increases due entirely to physical optical effect of the dominant scattering coefficient in the tissues, the $\mu_s$ of the RBCs. There is an IE, EE pair for each sequence of CCD frames constituting each segment of the experiment. For the "A" pair, as the pressure is applied to the fingertip and the light is turned on, the initial value of the IE is large followed by a fast roughly $10^0$-$10^{-1}$ second decay and a slower exponential decay over the next several $10^1$ of seconds.

To execute the next part of the measurement sequence after the condition A data is collected, the finger is maintained motionless with the laser blocked and the pressure at the set-up level i.e. ≈15 g/cm² for about 10 s before the laser is unblocked and the pressure is restored to 60 g/cm². This pressure is again maintained while the B pair is collected. In this case the initial IE of the B data nearly the same as the end of the A data and any initial drop in IE emission in the first few seconds is small compared to the initial drop observed for the A data. The EE emission for A and B data are very nearly the same and all the data show evidence of pulsing for their entire time courses.

After removing the finger from the device and executing enough movement to re-equilibrate the blood in the arm and hand area so that it felt normal, the same set-up procedure was executed placing the skin in a slightly different position with respect to the fingerprint ridges. In this case, before the C pair data were collected, the arm and hand were kept motionless and in contact with the actuator and the aperture as before the A run but not irradiated for a period of time equal to the A data collection period so that any fluid redistribution due to the changing hydrostatic pressure associated with assuming different body postures, i.e. sitting versus standing, would have time to occur but without laser irradiation. The dynamics of the C pair data is nearly identical to that of the A pair data although the average value of the EE of C data is less than that for either of the A or B data while the IE of C data is greater than that of the A data. Obvious heart pulsing is observable throughout all the data. The drop in IE is associated with the presence of the laser and not due to any change in hydrostatic pressure.

In addition to the observation of the photobleaching of fingertip skin, such process is related with laser power. The decay definitely increase, i.e. the photobleaching is faster with increasing laser power. The individual decay or photobleaching curves can be well fit by a single exponential equation. FIG. 25 shows the relationship between the averaged decay constant for two individuals using either index or middle fingers under four different excitation laser powers. The negative correlation with r=−0.96 validates the empirical observation reasonably well.

In order to further probe the effect of the laser the experiments depicted in FIG. 26 were executed. In this case the fingertip is set-up and brought to 60 g/cm² with the laser blocked. The laser is unblocked at around t=2 s with pressure already equilibrated and the IE is observed to fall exponentially again in the first 27 s. At this point the laser is blocked for 8 s in order for a dozen or more pulses to bring new blood into the irradiated volume without previous laser exposure. On reopening the shutters, the fluorescence returns to nearly the previous but not to a significantly greater level. The IE or BV data were never observed to exceed the pre-shuttered level by more than 10-15%.

Since it is clear that the laser has an effect on the probed volume that causes the fluorescence to decrease roughly exponentially, a series of experiments were undertaken to more clearly observe this apparent bleaching effect and possibly to determine the recovery time if any. In this case after the finger was positioned and brought into optical registration with the aperture, the finger was held motionless and isobaric with respect to the aperture while the aperture was translated in 20 μm per step (Newport NSA12 motorized miniature linear actuator driven by a NSC200 controller) with respect to the incoming laser thereby scanning the laser across the skin surface from tip to joint for the length of the entire aperture (diameter=2 mm). Because the laser is suspected to be bleaching the tissues, the shutters are used to only allow 60 ms slices of the CW laser to contact the skin during the scanning so that the actual duty cycle is only 6%.

A typical scan obtained in this manner is shown in FIG. 27. After the low duty cycle pre-scan is obtained the laser is allowed to contact and thereby "photobleach" the motionless skin near the center of the aperture for 50 s at 200 mW and 100% duty cycle. Afterwards another low duty cycle scan is conducted to reveal the effect of the photobleaching step. The fluorescence in the irradiated region is decreased by about 15-20% in the case of the non-diabetic test subject shown, and for all test subjects the bleaching effect has been observed to persist for as long as 45 min with the finger stationary and without any observed recovery of fluorescence. However, although more test subjects need to be included to establish this as a general empirical fact, so far test subjects with diabetes photobleach roughly twice as deeply as the non-diabetic test subjects, regardless of age.

In vitro experiments were conducted in order to determine the fluorescence properties of at least some of the more ubiquitous cutaneous and subcutaneous substances that could contribute to the observed fluorescence and photobleaching under 785 nm excitation. Table 4 shows several substances that were tested and did not exhibit fluorescence as well as a few that actually did have substantial fluorescence. Of those examined, it was surprising to find that carotene, which has a strong resonance Raman spectrum, does not fluoresce appreciably. The other candidates comprise anti-oxidants and vitamins that could conceivable have low lying electronic states that could mediate radiative decay.

TABLE 4

In-vitro investigation of fluorescence and photobleaching properties
of some cutaneous and subcutaneous constituents of human skin tissue

| Name | Solvent | Concentration Experimental | Physiological*[12] | Fluorescence/ Photo-bleach ability | Source Manufacture | Cat. # |
|---|---|---|---|---|---|---|
| L-Glutathione | DI water | ×5**, ×25 | ≈1.09 mM | N/N | Sigma-Aldrich | G4251 |
| Uric Acid | DI water | ×2, ×4 | 234-456 µM | N/N | Aldrich | 16,118-7 |
| β-Carotene | Cyclohexane | /2**, /4, /25 | 1.23-1.75 µM | N/N | Sigma | C9750 |
| Cholecalciferol | Cyclohexane | ×5, ×125, ×3125, ×78125 | 40-80 nM | N/N | Sigma | C9756 |
| L-Ascorbic acid | DI water | ×5, ×75, ×125, ×3125 | 50-60 µM | N/N | Sigma | A5960 |
| (±)-α-Tocopherol | Cyclohexane | Stock**, /4, /25 | ≈24 µM | N/N | Sigma | T3251 |
| Gelatin | DI water | 0.5-7.5 g/dL | N/A | Y/Y | Aldrich | 27,160-8 |
| Melanin | DI water | Stock, /2, /4 | Various | Y/Y | Sigma | M8631 |
| D-(−)-Ribose | DI water | 166 mM | ≈13.2 µM | N/N | Sigma | R7500 |
| L-Lysine | DI water | 171 mM | ≈153 µM | N/N | Aldrich | 16,971-4 |
| L-Arginine | DI water | 143 mM | ≈57 µM | N/N | Sigma-Aldrich | A5006 |
| Hemoglobin | DI water | 1.3-14.5 g/dL | 12-17 g/dL | Y/Y | Freshly harvested | |
| Plasma | PBS | Stock, /2, /3, /4 | N/A | Y/N | Freshly harvested | |

*Physiological concentrations of constituents shown above are in blood, interstitial fluid or in skin.
**Stock means saturated solution; ×5 means 5 times the physiological concentration; similarly, /2 means half the physiological or stock solution concentration.

The few substances that contribute appreciable fluorescence above the water background were hemoglobin, plasma, melanin, gelatin and early Maillard products of ribose, lysine and arginine mixture. The photobleaching of hemoglobin is shown in FIG. 28A as is the recovery when the bleached solution is allowed to recover in the dark for 1.5 hrs before retesting. Similarly the bleaching of melanin can be seen in FIG. 28B but the recovery is much less complete even when the solutions are allowed to recover for 2 hrs. Similar experiments on melanin which allow more than 12 hrs overnight recovery show comparable results with no noticeable fluorescence recovery.

Following Monnier (Sell and Monnier, 1989, *J. Biol. Chem.*, 264(36):21597-602), FIG. 29 was obtained from a mixture of Maillard reaction intermediate products by mixing ribose, lysine and arginine in a PBS buffered solution under constant 80° C. incubation. This reaction is much faster for pentoses than hexoses but the interconversion of these sugars in vivo is well-known and this reaction mixture is intended to mimic the glycation of collagen and other proteins, in the cytosol, interstitial fluids, plasma and extracellular matrix. Although Monnier monitored the reaction using UV-visible absorption and fluorescence, this is the first recognition that the early and probably late Maillard products are fluorescent in the NIR spectral range.

Although it is believed that these results have significant implications for in vivo and ex vivo NIR Raman spectroscopic probing in general, the discussion here is directed to their technological consequences with respect to on-going research in noninvasive glucose monitoring. The use of fluorescence as a measure of tissue volume, e.g. blood volume but perhaps in other applications static tissue volume also, seems to be well justified. The observed emission originates from all the tissues in the probed volume but some tissues are much more emissive than others. From within each particular tissue, e.g. static tissue, the emission is almost uniformly produced but within some tissues, i.e. RBCs and plasma, emission is produced to a much greater degree per unit volume than other tissues, i.e. static tissue. The bleaching and recovery behavior of these tissues must also be compared in order to assess the technological effects of these observations.

There is a combined Raman and fluorescence emission from water. Water occupies a very high volume fraction of all in vivo tissues and given the small number of emission counts produced per unit volume it would seem to be acceptable as a contributor to a net volume normalization. Most other fluorophores are much more efficient emitters and so small fluctuations in their net concentration and spatial/temporal distribution may lead to more errors and inconsistencies in volume normalization than similar fluctuations in hydration state and hematocrit. In actual fact changes in hydration state may be more important because of the effect on the tissue optics and light propagation than the changes in IE photons produced. It is also important that no indication that water-based IE signal photobleaches was observed.

The observed photobleaching effect in vivo and the recovery dynamics in vitro are favorable for the application of fluorescence as a volume normalizer. The observed photobleaching effect in vivo is nearly complete after about 20 s of NIR irradiation at ≈150 mW and it is suspected to be even faster at higher power illumination. Furthermore, the tissues of a least 12 test subjects, once bleached, do not recover appreciably for many tens of minutes so once a monitoring site on the skin is selected, the artifact to a volume normalization using IE becomes unimportant after the initial bleaching. A NIR Raman measurement protocol should contain a prebleaching segment, perhaps using wide area illumination at higher power than was employed herein. Furthermore, other wavelengths may also be more efficient at bleaching and this will have to be determined with continued experimentation.

Since efficient bleaching and significant recovery was observed in the hemoglobin experiments, the emission from blood, strictly speaking RBCs, may reach a steady state in practice when the laser induced emission is balanced against the laser induced bleaching process. Heart driven pulses are always observable and so a steady state is apparently reached very quickly, relative to heart beat frequency and blood flow rate in vivo.

Melanin is at best a difficult material to assess because it has a unique environment in vivo that is difficult to mimic in vitro. Nevertheless, although UV-visible emission has been reported, this is believed to be the first report of NIR excited emission from melanin. The oxidation state of melanin has been shown to be important in its UV-visible emission and may also be important in vivo. There are various endogenous and exogenous sources of porphyrins beyond hemoglobin that are expected to contribute their own emission. In addition, these materials are known singlet oxygen sensitizers that can be expected to (1) contribute some emission from the singlet oxygen itself, and (2) interact with other substances, e.g. melanin to alter their emission properties. Some skin, e.g. palmer skin and volar side fingertip skin contains much less melanin than other tissues and these effects will be reduced for the monitoring sites.

The UV-visible fluorescence of glycation products has already been proposed as a measure of long-term diabetic compliance of individuals with physician directed treatment regimens but this observation of NIR emission is new. That there may be increased fluorescence and photobleaching behavior for people with diabetes would be very significant and also in line with the previous observations. The suggestion of using a pre-bleaching step as an improved protocol for volume normalization for noninvasive glucose monitoring of this group of people would definitely be required. Indeed with sufficient pre-bleaching it would seem that all test subjects, regardless of age could be put on equal footing with regard to volume normalization. Since glucose itself reacts very slowly with lysine and arginine, glycation of extracellular materials directly from glucose would be very slow. However, the cytosol of any cell that can support glycolysis also has the enzyme complement to support the pentose phosphate shunt that produces ribose from glucose. Ribose participates in the Maillard reaction roughly 30 times faster than does glucose and so intracellular glycation is likely to be extensive for diabetics compared to non diabetic people, regardless of age. The glycation of non-diabetics is likely dominated by extracellular chemistry whereas that of diabetics is intracellular in nature. Thus the apparent increase in fluorescence and bleaching of diabetics could result from this effect.

Observing the degree of photobleaching and the apparent recovery dynamics aids in a rough ordering and portioning of the observed emission to the various possible contributors. Since the observed photobleaching reduces the net fluorescence by at least 10-15%, and that fluorescence does not recover appreciably when the bleaching is interrupted in order to allow perfusion with non-bleached blood, at least 15% of the net fluorescence originates with the static tissues. But for people who have diabetes, the total contribution to bleaching is nearly twice that percentage, and that additional bleaching capacity cannot be associated with blood due to its temporal modulation properties. So in a given individual, static tissue could contribute as much as twice that amount, with some additional fraction not being bleachable. For example, accounting for a water contribution from the static tissue roughly in proportion to its overwhelming volume percent of the probed volume and it is crudely estimated that over half of the total fluorescence comes from the static tissues.

While the foregoing has not completely accounted for all of the possible sources of NIR emission for in vivo fingertips, it is possible to roughly order the amount of fluorescence that originates with static tissues versus blood, i.e. plasma and RBCs taken together. A robust pre-bleaching step will enable more effective use of fluorescence as a volume normalizer when using NIR Raman in developing technology for noninvasive blood glucose monitoring. People with diabetes may require more prebleaching than the remaining segments of the general population due to the presence of early and possibly advanced Maillard products in the skin and blood itself.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. A method of obtaining a hematocrit from a sample of in vivo tissue comprising:
   (a) irradiating the sample with a single incident wavelength on a sample of tissue;
   (b) simultaneously measuring wavelength shifted (IE) and unshifted (EE) light emitted from the tissue; and
   (c) determining a relative volume of light emitted from two phases, wherein the two phases comprise a first Rayleigh and Mie scattering and fluorescent phase associated with red blood cells, and a second, non-scattering phase associated with plasma, wherein the hematocrit is calculated from the volume of light emitted by the first phase ($\phi_r$) relative to the total volume of light emitted from the first and second phases ($\phi_r + \phi_p$), wherein the determining comprises calculating:

$$\phi_r / (\phi_r + \phi_p) \qquad [5]$$

$$\text{wherein } \phi_r = a + \left(b \frac{EE}{EE_0}\right) + \left(c \frac{IE}{IE_0}\right) \qquad [8]$$

$$\phi_p = d + \left(e \frac{EE}{EE_0}\right) + \left(f \frac{IE}{IE_0}\right) \qquad [9]$$

$$EE = \aleph_1 + \aleph_2 \phi_p + \aleph_3 \phi_r \qquad [6]$$

$$IE = \aleph_4 + \aleph_5 \phi_p + \aleph_6 \phi_r \qquad [7]$$

wherein EE is total elastically (unshifted) emitted light, IE is total inelastically (shifted) emitted light, $\aleph_1$ and $\aleph_4$ are the fractions of EE and IE, respectively, from static tissue; $\aleph_2$ and $\aleph_5$ are the fractions of EE and IE, respectively, from plasma; $\aleph_3$, and $\aleph_6$ are the fractions of EE and IE, respectively, from red blood cells; and $\aleph_{1-6}$ are calculated numerically using the radiative transport equation (RTE) to determine EE and IE as a function of $\phi_r$ and $\phi_p$; wherein $EE_0$ and $IE_0$ are average values of EE and IE over a calibration time period; and wherein a-f are obtained by inverting equations [6] and [7] to express $\phi_r$ and $\phi_p$ in terms of EE and IE.

2. The method of claim 1, wherein the incident wavelength is 580-2500 nm.

3. The method of claim 2, wherein the incident wavelength is 785, 805 or 830 nm.

4. The method of claim 1, wherein the measuring of step (b) is at 500-1800 cm$^{-1}$ for shifted light, and at $-30$-$+10$ cm$^{-1}$ for unshifted light.

5. The method of claim 1, wherein the tissue is fingertip, a+b+c=0.004 and d+e+f=0.036.

6. A method of obtaining a hematocrit from a sample of in vivo tissue comprising:
   (a) irradiating the sample with a single incident wavelength on a sample of tissue;
   (b) simultaneously measuring wavelength shifted (IE) and unshifted (EE) light emitted from the tissue; and
   (c) determining a relative volume of light emitted from two phases, wherein the two phases comprise a first Rayleigh and Mie scattering and fluorescent phase associated with red blood cells, and a second, non-scattering phase associated with plasma, wherein the hematocrit is calculated from the volume of light emitted by the first phase ($\phi_r$) relative to the total volume of light emitted from the first and second phases ($\phi_r+\phi_p$), wherein the determining comprises calculating:

$$\phi_r/(\phi_r+\phi_p) \quad [5]$$

$$\text{wherein } \phi_r = a + \left(b\frac{EE}{EE_0}\right) + \left(c\frac{IE}{IE_0}\right) \quad [8]$$

$$\phi_p = d + \left(e\frac{EE}{EE_0}\right) + \left(f\frac{IE}{IE_0}\right) \quad [9]$$

wherein EE is total elastically (unshifted) emitted light, IE is total inelastically (shifted) emitted light; and wherein a-f are obtained from estimated values for $\phi_r$ and $\phi_p$ derived from a calibration condition during which $EE=EE_0$ and $IE=IE_0$ and/or another calibration condition in which IE and EE can be associated with the cardiac pulse.

7. The method of claim 6, wherein the calibration condition comprises application of pressure to the sample of tissue, wherein the pressure is greater than systolic pressure.

8. The method of claim 1, wherein the tissue is human.

9. The method of claim 1, wherein the tissue is a fingertip.

10. The method of claim 9, wherein the fingertip is pressed against an aperture of an apparatus that emits light directed at the fingertip through the aperture.

11. The method of claim 10, wherein the pressure at which the fingertip is pressed is approximately the average of the prevailing systolic and diastolic blood pressures of the subject.

12. The method of claim 1, wherein EE and IE are the AC components of the time dependent EE and IE signals.

13. The method of claim 1, wherein EE and IE are the AC components of the time dependent EE and IE signals in the bandpass of 2.5 Hz to 0.25 Hz.

14. The method of claim 1, wherein EE and IE are the DC components of the time dependent EE and IE signals.

15. The method of claim 1, wherein EE and IE are the DC components of the time dependent EE and IE signals in the bandpass of 0±10 Hz.

16. An apparatus for obtaining a hematocrit from a sample of tissue comprising:
   (a) means for irradiating the sample with a single incident wavelength on a sample of tissue;
   (b) means for simultaneously measuring wavelength shifted and unshifted light emitted from the tissue;
   (c) means for determining a relative volume of light emitted from two phases, wherein the two phases comprise a first predominantly Rayleigh and Mie scattering and fluorescent phase associated with red blood cells, and a second, non-scattering phase associated with plasma; and
   (d) means for calculating a volume fraction of red blood cells ($\phi_r$) relative to the total volume of red blood cells and plasma ($\phi_r+\phi_p$), wherein the determining comprises calculating:

$$\phi_r/(\phi_r+\phi_p) \quad [5]$$

$$\text{wherein } \phi_r = a + \left(b\frac{EE}{EE_0}\right) + \left(c\frac{IE}{IE_0}\right) \quad [8]$$

$$\phi_p = d + \left(e\frac{EE}{EE_0}\right) + \left(f\frac{IE}{IE_0}\right) \quad [9]$$

$$EE = \aleph_1 + \aleph_2 \phi_p + \aleph_3 \phi_r \quad [6]$$

$$IE = \aleph_4 + \aleph_5 \phi_p + \aleph_6 \phi_r \quad [7]$$

and wherein EE is total elastically (unshifted) emitted light, IE is total inelastically (shifted) emitted light, $\aleph_1$ and $\aleph_4$ are the fractions of EE and IE, respectively, from static tissue; $\aleph_2$ and $\aleph_5$ are the fractions of EE and IE, respectively, from plasma; $\aleph_3$ and $\aleph_6$ are the fractions of EE and IE, respectively, from red blood cells; and $\aleph_{1-6}$ are calculated numerically using the radiative transport equation (RTE) to determine EE and IE as a function of $\phi_r$ and $\phi_p$; wherein $EE_0$ and $IE_0$ are average values of EE and IE over a calibration time period; and wherein a-f are obtained by inverting equations [6] and [7] to express $\phi_r$ and $\phi_p$ in terms of EE and IE.

17. The apparatus of claim 16, wherein the incident wavelength is 580-2500 nm.

18. The apparatus of claim 17, wherein the incident wavelength is 785, 805 or 830 nm.

19. The apparatus of claim 16, wherein the measuring of step (b) is at 500-1800 cm$^{-1}$ for shifted light, and at −30-+10 cm$^{-1}$ for unshifted light.

20. An apparatus for obtaining a hematocrit from a sample of tissue comprising:
   (a) means for irradiating the sample with a single incident wavelength on a sample of tissue;
   (b) means for simultaneously measuring wavelength shifted and unshifted light emitted from the tissue;
   (c) means for determining a relative volume of light emitted from two phases, wherein the two phases comprise a first predominantly Rayleigh and Mie scattering and fluorescent phase associated with red blood cells, and a second, non-scattering phase associated with plasma; and
   (d) means for calculating a volume fraction of red blood cells ($\phi_r$) relative to the total volume of red blood cells and plasma ($\phi_r+\phi_p$), wherein the determining comprises calculating:

$$\phi_r/(\phi_r+\phi_p) \quad [5]$$

$$\text{wherein } \phi_r = a + \left(b\frac{EE}{EE_0}\right) + \left(c\frac{IE}{IE_0}\right) \quad [8]$$

$$\phi_p = d + \left(e\frac{EE}{EE_0}\right) + \left(f\frac{IE}{IE_0}\right) \quad [9]$$

wherein EE is total elastically (unshifted) emitted light, IE is total inelastically (shifted) emitted light; and wherein a-f are obtained from estimated values for $\phi_r$ and $\phi_p$ derived from a calibration condition during which $EE=EE_0$ and $IE=IE_0$ and/or another calibration condition in which IE and EE can be associated with the cardiac pulse.

21. The method of claim 6, wherein the incident wavelength is 580-2500 nm.

22. The method of claim 21, wherein the incident wavelength is 785, 805 or 830 nm.

23. The method of claim 6, wherein the measuring of step (b) is at 500-1800 cm$^{-1}$ for shifted light, and at $-30-+10$ cm$^{-1}$ for unshifted light.

24. The method of claim 6, wherein the tissue is human.

25. The method of claim 7, wherein the tissue is a fingertip.

26. The method of claim 25, wherein the fingertip is pressed against an aperture of an apparatus that emits light directed at the fingertip through the aperture.

27. The method of claim 26, wherein the pressure at which the fingertip is pressed is approximately the average of the prevailing systolic and diastolic blood pressures of the subject.

* * * * *